United States Patent [19]

Chan et al.

[11] Patent Number: 5,571,821
[45] Date of Patent: Nov. 5, 1996

[54] SULFONAMIDES AND DERIVATIVES THEREOF THAT MODULATE THE ACTIVITY OF ENDOTHELIN

[75] Inventors: Ming Fai Chan; Bore G. Raju; Adam Kois; Erik J. Verner; Chengde Wu; Rosario S. Castillo; Venkatachalapathi Yalamoori; Vitukudi N. Balaji; Kalyanaraman Ramnarayan, all of San Diego, Calif.

[73] Assignee: Texas Biotechnology Corporation, Del.

[21] Appl. No.: 247,072

[22] Filed: May 20, 1994

Related U.S. Application Data

[63] Continuation-in-part of Ser. No. 222,287, Apr. 5, 1994, Ser. No. 142,552, Oct. 21, 1993, Pat. No. 5,514,691, Ser. No. 142,159, Oct. 21, 1993, Pat. No. 5,464,853, Ser. No. 142,631, Oct. 21, 1993, abandoned, Ser. No. 100,565, Jul. 30, 1993, abandoned, Ser. No. 100,125, Jul. 30, 1993, abandoned, and Ser. No. 65,202, May 20, 1993, abandoned, said Ser. No. 222,287, is a continuation-in-part of Ser. No. 142,159, Ser. No. 142,559, Oct. 25, 1993, Pat. No. 5,378,463, Ser. No. 142,631, Ser. No. 100,565, Ser. No. 100,125, and Ser. No. 65,202, said Ser. No. 142,159, Ser. No. 142,559, and Ser. No. 142,631, each is a continuation-in-part of Ser. No.100,565, Ser. No. 100,125, and Ser. No. 65,202, said Ser. No. 100,565, and Ser. No. 100,125, each is a continuation-in-part of Ser. No.65,202.

[51] Int. Cl.[6] .......................... A61K 31/47; C07D 413/12
[52] U.S. Cl. .......................... 514/312; 514/307; 514/309; 514/310; 514/311; 514/313; 514/314; 514/337; 514/338; 514/340; 514/361; 514/362; 514/363; 514/365; 514/369; 514/370; 514/372; 514/378; 514/379; 514/38; 546/139; 546/141; 546/142; 546/143; 546/144; 546/146; 546/147; 546/153; 546/155; 546/159; 546/162; 546/167; 546/172; 546/272.1; 546/198; 546/209; 548/127; 548/146; 548/182; 548/190; 548/202; 548/203; 548/205; 548/206; 548/213; 548/214; 548/241; 548/243; 548/244; 548/245; 548/247
[58] Field of Search .......................... 548/241, 243, 548/244, 245, 247, 127, 146, 182, 190, 202, 203, 205, 206, 213, 214; 514/378, 379, 380, 361, 362, 363, 365, 369, 370, 372, 311, 312, 313, 314, 340, 337, 338; 546/153, 155, 159, 162, 167, 172

[56] References Cited

U.S. PATENT DOCUMENTS

| | | | |
|---|---|---|---|
| 3,300,488 | 1/1967 | Onoue et al. | 260/239.9 |
| 3,660,383 | 5/1972 | Sumimoto et al. | 260/239.9 |
| 4,752,613 | 6/1988 | Floyd et al. | 514/438 |
| 4,997,836 | 5/1991 | Sugihara et al. | 514/253 |
| 5,114,918 | 5/1992 | Ishikawa et al. | 514/11 |
| 5,208,243 | 5/1993 | Peglion et al. | 514/309 |
| 5,270,313 | 12/1993 | Burri et al. | 514/253 |
| 5,292,740 | 3/1994 | Burri et al. | 514/256 |
| 5,378,715 | 1/1995 | Stein et al. | 514/329 |
| 5,389,620 | 2/1995 | Ishikawa et al. | 514/80 |
| 5,389,633 | 2/1995 | Miyake et al. | 514/233.2 |
| 5,407,941 | 4/1995 | Carceller et al. | 514/290 |
| 5,420,123 | 5/1995 | Murugesan | 514/220 |
| 5,420,129 | 5/1995 | Breu et al. | 514/252 |
| 5,420,131 | 5/1995 | Carceller et al. | 514/253 |
| 5,420,133 | 5/1995 | Dhanoa et al. | 514/256 |
| 5,420,138 | 5/1995 | Corbier et al. | 514/300 |
| 5,420,275 | 5/1995 | Masuya et al. | 544/236 |

FOREIGN PATENT DOCUMENTS

| | | |
|---|---|---|
| 5461286 | 3/1985 | Australia . |
| 2067288 | 10/1992 | Canada . |
| 2071193 | 12/1992 | Canada . |
| 0404525 | 12/1990 | European Pat. Off. . |
| 0405421 | 1/1991 | European Pat. Off. . |
| 0411150 | 2/1991 | European Pat. Off. . |
| 0436189 | 7/1991 | European Pat. Off. . |
| 0457195 | 11/1991 | European Pat. Off. . |
| 0460679 | 12/1991 | European Pat. Off. . |
| 0496452 | 7/1992 | European Pat. Off. . |
| 0558258 | 9/1993 | European Pat. Off. . |
| 0569193 | 11/1993 | European Pat. Off. . |
| 0640596 | 3/1995 | European Pat. Off. . |
| 60-188088 | 9/1985 | Japan . |
| 4134048 | 5/1992 | Japan . |
| 2259450 | 3/1993 | United Kingdom . |
| 9308799 | 5/1993 | WIPO . |

OTHER PUBLICATIONS

Ihara et al., "An endothelin receptor ($ET_a$) antagonist isolated From *Streptomyces Misakiensis*," *Biochem. and Biophys. Research Commun.*, 178(1):132–137 (1991).

(List continued on next page.)

*Primary Examiner*—Joseph McKane
*Attorney, Agent, or Firm*—Stephanie L. Seidman; Brown, Martin, Haller & McClain

[57] ABSTRACT

Sulfonamides and methods using these sulfonamides for inhibiting the binding of an endothelin peptide to an endothelin receptor by contacting the receptor with the sulfonamide are provided. Methods for treating endothelin-mediated disorders by administering effective amounts of one or more of these sulfonamides or prodrugs thereof that inhibit or increase the activity of endothelin are also provided. The sulfonamides have formula I:

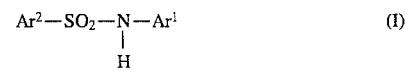

in which $Ar^1$ is a 3- or 5-isoxazolyl and $Ar^2$ is selected from among alkyl, including straight and branched chains, aromatic rings, fused aromatic rings and heterocyclic rings, including 5-membered heterocycles with one, two or more heteroatoms and fused ring analogs thereof and 6-membered rings with one, two or more heteroatoms and fused ring analogs thereof. $Ar^2$ is preferably thiophenyl, furyl, pyrrolyl, naphthyl, and phenyl. Compounds in which $Ar^1$ is a 4-halo-substituted isoxazole are more active than the corresponding alkyl-substituted compound and compounds in which $Ar^1$ is substituted at this position with a higher alkyl tend to exhibit greater affinity for $ET_B$ receptors than the corresponding lower alkyl-substituted compound.

91 Claims, No Drawings

OTHER PUBLICATIONS

Spinella et al., "Design and synthesis of a specific endothelin 1 antagonist: Effects on pulmonary vasoconstriction," *Proc. Natl. Acad. Sci. USA*, 88p:7443–7446 (1991).

Saeki et al., "[Ala$^{1,3,11,15}$]endothelin–1 analogs with ET$_B$ agonistic activity," *Biochem. and Biophys. Research Commun.*, 179(1):286–292 (1991).

Gu et al., "The inhibitory effect of [D–Arg$^1$, D–Phe, D–Try$^{7,9}$, Leu$^{11}$] substance P on endothelin–1 binding sites in rat cardiac membranes," *Biochem. and Biophys. Research Commun.*, 179(1):130–133 (1991).

Panek et al., "Endothelin and structurally related analogs distinguish between endothelin receptor subtypes," *Biochem. and Biophys. Research Commun.*, 183(2):566–571 (1992).

Ihara et al., "Biological profiles of highly potent novel endothelin antagonists selective for the ET$_A$ receptor," *Life Sciences*, 50:247–255 (1991).

Hirata et al., "Receptor binding activity and cytosolic free calcium response by synthetic endothelin analogs in culture rat vascular smooth muscle cells," *Biochem. and Biophys. Research Commun.*, 160:228–234 (1989).

Nakajima et al., "Synthesis of endothelin–1 analogues, endothelin–3, and sarafotoxin S6b: Structure–activity relationships," *J. of Cardiovascular Pharm.*, 13(Suppl. 5):S8–S12 (1989).

Yanagisawa et al., "A novel potent vasoconstrictor peptide produced by vascular endothelial cells," *Nature*, 332:411–415 (1988).

Kashiwabara et al., "Putative precursors of endothelin have less vasoconstrictor activity in vitro but a potent pressor effect in vivo," *FEBS Letters*, 247(1):73–76 (1989).

von Geldren et al., "A fluorogenic assay for endothelin–converting enzyme," *Peptide Research*, 4(1):32–35 (1991).

Inoue et al., "The human endothelin family: Three structurally and pharmacologically distinct isopeptides predicted by three separate genes," *Proc. Natl. Acad. Sci. USA*, 86:2863–2867 (1989).

Saida et al., "A novel peptide, vasoactive intestinal contractor, of a new (endothelin) peptide family," *J. Biol. Chem.*, 264(25):14613–14616 (1989).

Brooks et al., "Effect of nifedipine on cyclosporine A–induced nephrotoxicity, urinary endothelin excretion and renal endothelin receptor number," *Eur. J. of Pharmacology*, 194:115–117 (1991).

Bolger et al., "Vascular reactivity, tissue levels, and binding sites for endothelin: A comparison in the spontaneously hypertensive and Wistar–Kyoto rats," *Can. J. Physiol. Pharm.*, 69:406–413 (1990).

Simonson et al., "Endothelin–1 stimulates contraction of rat glomerular mesangial cells and potentiates β–Adrenergic-–mediated cyclic adenosine monophosphate accumulation," *J. Clin. Invest.*, 85:790–797 (1990).

Stewart et al., "Increased plasma endothelin–1 in pulmonary hypertension: Marker or mediator of disease?" *Annals of Internal Medicine*, 114(6):464–469 (1991).

Takayanagi et al., "Presence of non–selective type of endothelin receptor on vascular endothelium and its linkage to vasodilation," *FEBS Letters*, 282(1):103–106 (1991).

Nishikori et al., "Receptor binding affinity and biological activity of C–terminal elongated forms of endothelin–1," *Neurochem. Int.*, 18(4):535–539 (1991).

Castiglione et al., "Alanine scan of endothelin," Peptides: Chemistry and Biology, Proc. Amer. Rept. Symp. (Twelfth), J. A. Smith and J. E. Rivier, Eds., ESCOM, Leiden, 1992, pp. 402–403.

Galantino et al., "D–Amino acid scan of endothelin," Peptides: Chemistry & Biology, Proc. Amer. Report. Symp. (Twelfth), J. A. Smith and J. E. Rivier, Eds., ESCOM, Leiden, 1992, pp. 404–405.

Filep et al., "Endothelin–1 induces prostacyclin release from bovine aortic endothelial cells," *Biochem. and Biophys. Research Comm.*, 177(1):171–176 (1991).

Spokes et al., "Studies with endothelin–3 and endothelin–1 on rat blood pressure and isolated tissues: Evidence for multiple endothelin receptor subtypes," *J. of Cardiovascular Pharmacology*, 13(Suppl. 5):S191–S192 (1989).

Cardell et al., "Two functional endothelin receptors in guinea–pig pulmonary arteries," *Neurochem. Int.*, 18(4):571–574 (1991).

Borges et al., "Tissue selectivity of endothelin," *Eur. J. Pharmacology*, 165:223–230 (1989).

Ogawa et al., "Molecular cloning of a non–isopeptide–selective human endothelin receptor," *Biochem. and Biophys. Research Comm.*, 178(1):248–255 (1991).

Schvartz et al., "Bovine cerebellum endothelin receptor: Solubilization and identification," *Endocrinology*, 126(6):3218–3222 (1990).

Saudek et al., "Solution conformation of endothelin–1 by $^1$H NMR, CD, and molecular modeling," *Int. J. Peptide Protein Res.*, 37:174–179 (1991).

Aumelas et al., "Determination of the structure of [Nle$^7$]–endothelin by $^1$H NMR," *Int. J. Peptide Protein Res.*, 37:315–324 (1991).

Perkins et al., "Proposed solution structure of endothelin," *Int. J. Peptide Protein Res.*, 36:128–133 (1990).

Spinella et al., "A proposed structural model of endothelin," *Peptide Research*, 2(4):286–291 (1989).

Saudek et al., "$^1$H–NMR study of endothelin, sequence–specific assignment of the spectrum and a solution structure," *FEBS Letters*, 257(1):145–148 (1989).

Ramachandran et al., "Conformation of polypeptides and proteins," *Adv. Prot. Chem.*, 23:283–437 (1968).

Szelke et al., "Novel transition–state analogue inhibitors of renin," In Peptides: Structure and Function, Proceeding of the Eighth American peptide symposium, (Hruby and Rich, Eds.); pp. 579–582, Pierce Chemical Co., Rockford, Illinois (1983).

Allen et al., "The Cambridge crystallographic data centre: Computer–based search, retrieval, analysis and display of Information," *Acta Crystallogr.*, B35:2331–2339 (1979).

Weiner et al., "A new force field for molecular mechanical simulation of nucleic acids and proteins," *J. Am. Chem. Soc.*, 106(3):765–784 (Eng.) (1984).

Cooper et al., "A novel approach to molecular similarity," *J. Comput.–Aided Mol. Design*, 3:253–259 (1989).

Brint et al., "Upperbound procedures for the identification of similar three–dimensional chemical structures," *J. Comput.–Aided Mol. Design*, 2:311–310 (1988).

Weiner et al., "An all atom force field for simulations of proteins and nucleic acids," *J. Comput. Chem.*, 7(2):230–252 (1986).

Karplus, M., "Molecular Dynamics: Applications to Proteins," in Computer Simulation of Chemical and Biomolecular Systems, (Bevendge and Jorfensen, Eds.) Annals of the New York Acad. Science, 482:255–266 (1986).

Balasubramanian, R., "New type of representation for mapping chain folding in protein molecules," *Nature*, 266:856–857 (1977).

Kemp, D. S., "Peptidomimetics and the template approach to nucleation of β–sheets and α–helices in peptides," *Tibtech*, 8:249–255 (1990).

Arai et al., "Cloning and expression of a cDNA encoding an endothelin receptor," *Nature* 348:730–732 (1990).

De Nucci et al., "Pressor effects of circulating endothelin are limited by its removal in the pulmonary circulation and by the release of prostacyclin and endothelium–derived relaxing factor," *Proc. Natl. Acad. Sci.* 85:9797 (1988).

Hiley et al., "Functional studies on endothelin catch up with molecular biology," *Trends Pharmacol. Sci.* 10:47–49 (1989).

Kaltenbronn et al., "Renin inhibitors containing isosteric replacements of the amide bond connecting the $P_3$ and $P_2$ sites," *J. Med. Chem.* 33:838–845 (1990).

Kloog et al., "Similarities in mode and sites of action of sarafotoxins and endothelins," *Trends Pharmacol. Sci.* 10:212–214 (1989).

Maggi et al., "Potent contractile effect of endothelin in isolated guinea–pig airways," *Eur. J. Pharmacol.* 160:179–182 (1989).

Martin et al., "Identification and characterization of endothelin binding sites in rat renal papillary and glomerular membranes," *Biochem. Biophys. Res. Commun.* 162:130–137 (1989).

Morel et al., "Increased plasma and pulmonary lymph levels of endothelin during endotoxin shock," *Eur. J. Pharm.* 167:427–428 (1989).

Palmer et al., "Nitric oxide release accounts for the biological activity of endothelium–derived relaxing factor," *Nature* 327:524–526 (1987).

Saito et al., "Application of monoclonal antibodies for endothelin to hypertensive research," *Hypertension* 15:734–738 (1990).

Sakurai et al., "Cloning of a cDNA encoding a non–isopeptide–selective subtype of the endothelin receptor," *Nature* 348:732–735 (1990).

Takayanagi et al., "Multiple subtypes of endothelin receptors in porcine tissues: characterization by ligand binding, affinity labeling and regional distribution," *Reg. Pep.* 32:23–37 (1991).

Tomita et al., "Plasma endothelin levels in patients with acute renal failure," *N. Engl. J. Med.* 321:1127 (1989).

Anagnostou et al., "Erythropoietin has mitogenic and positive chemotactic effects on endothelial cells," *P.N.A.S.* 87:5987–5982 (1990).

Buemi et al., "Influence of recombinant erythropoietin on the production of endothelin–1 from human umbilical artery," *Nephron* 64(1):165–166 (1993).

Carlini et al., "Intravenous erythropoietin (rHuEPO) administration increases plasma endothelin and blood pressure in hemodialysis patients," *Am. J. Hyper.* 6:103–107 (1993).

Clarke et al., "Endothelin is a potent long–lasting vasconstrictor in men," *Am. J. Physiol.* 257(6 pt 2):H2033–H2035 (1989).

Eschbach et al., "Recombinant human erythropoietin in anemic patients with end stage renal disease; results of a phase III multicenter clinical trial," *Ann. Intern. Med.* 111:992–1000 (1989).

Heidenreich et al., "Erythropoietin induces contraction of isolated renal small resistance vessels," *Nephrol. Dial. Transplant* 5:739–740 (1990).

Hori et al., "Hemodynamics and volume changes by recombinant human erythropoietin (rHuEPO) in the treatment of anemic hemodialysis patients," *Clin. Nephrol.* 33:293–298 (1990).

Koyama et al., "Plasma endothelin levels in patients with uremia," *Lancet* 1(8645):991–992 (1989).

Nonnast–Daniel et al., "Atrial natriuretic peptide and central hemodynamics during correction of renal anemia by recombinant human erythropoietin treatment in regular dialysis treatment patients," *Nephrol Dial Transplant* 4:478 (1989).

Raine er al., Effect of erythropoietin on blood pressure," *Am. J. Kid. Dis.* 18(Suppl):76–83 (1991).

Samtleben et al., "Blood pressure change during treatment with recombinant human erythropoietin," *Contrib. Nephrol.* 66:114–122 (1988).

Schafer et al., "Treatment of renal anemia with recombinant human erythropoietin," *Am. J. Nephrol.* 8:352–362 (1989).

Sundal et al., "Correction of anemia of chronic renal failure with recombinant human erythropoietin:Safety and efficacy of one year's treatment in a European multicenter study of 150 hemodialysis–dependant patients," *Nephrol Dial Transplant* 4:979–987 (1989).

Tkayama et al., "Effects of recombinant human eryghropoietin on blood coagulation, fibrinolysis and endothelium in hemodialysis patients," *Blood Purif.* 1:53–54 (1991).

Yamashita et al., "Recombinant human erythropoietin (rHuEPO) induces high plasma endothelin (ET) levels in hemodialysis patients," *J. Am. Soc. Nephrol.* 1:409 (1990).

Ohashi et al., "Asterric acid, a new endothelin binding inhibitor," *J. Antibiotics* 45(10):1684–1685 (1992).

Williams et al., "Sarafotoxin S6c: An agonist which distinguishes between endothelin receptor subtypes," *Biochem. and Biophys. Research Commun.*, 175(2):556–561 (1991).

Fujimoto, et al., "Isoxazole derivatives. II. Synthesis and structure of N–acylsufodiazoles and their homologs", *Chemical Abstracts*, vol. 65, No. 2, Jul. 18, 1966, Abstract No. 2241eq.

Stein, et al., "The Discovery of Sulfonamide Endothelin Antagonists and the Development of the Orally Active $ET_a$–Antagonist 5–(Dimethylamino)–N–(3, 4–dimethyl–5–isoxazolyl)–1–naphthalensulfonamide," *J. Med. Chem.* 37(3):329–331 (1994).

Doherty, "Endothelin: A new challenge," *J. Medicinal Chem.*, 35(9):1493–1508 (1992).

Bolger et al., "Characterization of binding of the $Ca^{++}$ channel antagonist [$^3$H] nitrendipine to guinea–pig ileal smooth muscle," *J. of Pharmacology and Experimental Therapeutics*, 225:291–309 (1983).

Shimazaki, et al., "Piperazine derivatives," *Chem. Abstracts* 106:558 (abst. no. 33114a) (1987).

Benigni, et al., "A specific endothelin subtype A receptor antagonist protects against injury in renal disease progression," *Kidney International* 44:440–444 (1993).

Cody, et al., "The rational design of a highly potent combined $ET_A$ and $ET_8$ receptor antagonist (PD145065) and related analogues," *Med. Chem. Res.* 3:154–162 (1993).

Fujimoto, et al., "A novel non–peptide endothelin antagonist isolated from bayberry," *FEBS* 305(1):4–44 (1992).

Ishikawa, et al., "Cyclic pentapeptide endothelin antagonists with high $ET_A$ selectivity. Potency– and solubility–enhancing modifications," *J. Med. Chem.* 35

Miyata, et al., "WSOO9 A and B, new endothelin receptor antagonists isolated from Streptomyces sp. No. 89009," *J. Antibiotics* 45(7):1029–1040 (1992).

Miyata, et al., "WS–7338, new endothelin receptor antagonists isolated from Streptomyces sp. No. 7338," *J. Antibiotics* 45(1):74–82 (1992).

Nakajima, et al., "Endothelin–binding inhibitors, BE–18257A and BE–18257B II. Structure determintation," *J. Antibiotics* 44(12):1348–1356 (1991).

Nishikibe, et al., "Antihypertensive effect of a newly synthesized endothelin antagonist, BQ–123, in a genetic hypertensive model," *Life Sci.* 52:717–724 (1993).

SULFONAMIDES AND DERIVATIVES THEREOF THAT MODULATE THE ACTIVITY OF ENDOTHELIN

RELATED APPLICATIONS

This application is a continuation-in-part of the following applications: U.S. application Ser. No. 08/222,287 to Chan et al., filed Apr. 5, 1994, entitled "THIOPHENYL-, FURYL- AND PYRROLYL-SULFONAMIDES AND DERIVATIVES THEREOF THAT MODULATE THE ACTIVITY OF ENDOTHELIN", U.S. application Ser. No. 08/142,552 to Chan et al., filed Oct. 21, 1993, now U.S. Pat. No. 5,514,691 entitled "N-(4-HALO-ISOXAZOLYL)-SULFONAMIDES AND DERIVATIVES THEREOF THAT MODULATE THE ACTIVITY OF ENDOTHELIN", U.S. application Ser. No. 08/142,159 to Chan et al., filed Oct. 21, 1993, now U.S. Pat. No. 5,464,853 entitled "N-(5-ISOXAZOLYL)BIPHENYLSULFONAMIDES, N-(3-ISOXAZOLYL)BIPHENYLSULFONAMIDES AND DERIVATIVES THEREOF THAT MODULATE THE ACTIVITY OF ENDOTHELIN"; U.S. application Ser. No. 08/142,631 to Chan et al., filed Oct. 21, 1993, now abandoned entitled "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN"; U.S. application Ser. No. 08/100,565 to Chan et al., filed Jul. 30, 1993, now abandoned entitled "N-(5-ISOXAZOLYL)-SULFONAMIDES AND DERIVATIVES THEREOF THAT MODULATE THE ACTIVITY OF ENDOTHELIN"; U.S. application Ser. No. 08/100,125 to Chan et al., filed Jul. 30, 1993, now abandoned entitled "N-(3-ISOXAZOLYL)SULFONAMIDES AND DERIVATIVES THEREOF THAT MODULATE THE ACTIVITY OF ENDOTHELIN", and U.S. application Ser. No. 08/065,202, to Chan, filed May 20, 1993, now abandoned entitled "SULFONAMIDES AND DERIVATIVES THEREOF THAT MODULATE THE ACTIVITY OF ENDOTHELIN".

U.S. application Ser. No. 08/222,287 is a continuation-in-part of U.S. application Ser. Nos. 08/142,159, 08/142,559, filed Oct. 25, 1993, now U.S. Pat. No. 5,378,463 08/142,631, filed Oct. 25, 1993, now U.S. Pat. No. 5,373,463, 08/100,565, 08/100,125 and 08/065,202. U.S. application Ser. Nos. 08/142,159, 08/142,559, 08/142,631 are continuation-in-part applications of U.S. application Ser. Nos. 08/100,565, 08/100,125 and 08/065,202, and U.S. application Ser. Nos. 08/100,565 and 08/100,125 are continuation-in-part applications of U.S. application Ser. No. 08/065,202.

The subject matter of each of U.S. application Ser. Nos. 08/222,287, 08/142,159, 08/142,559, 08/142,631, 08/100,565, 08/100,125 and 08/065,202 is each incorporated herein in its entirety.

FIELD OF THE INVENTION

The present invention relates to the compounds that modulate the activity of the endothelin family of peptides. In particular, sulfonamides and derivatives thereof that modulate the activity of at least member of the endothelin family of peptides are provided. The formulation of these compounds as pharmaceuticals and use thereof as endothelin agonists and antagonists are also provided herein. The compounds herein may also be used in vitro in methods for distinguishing among the endothelin peptides, among endothelin receptor types and for affinity isolation of endothelin receptors.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332:411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$, $Leu^7$) endothelin-1 and endothelin-3 is ($Thr^2$, $Phe^4$, $Thr^5$, $Tyr^6$, $Lys^7$, $Tyr^{14}$) endothelin-1. These peptides are, thus, highly conserved at the C-terminal ends.

Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69:406–413). In isolated vascular strips, for example, endothelin-1 is a potent ($EC_{50}$= $4\times10^{-10}$M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists, The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2$–$6\times10^{-10}$M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis einqadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10:212–214).

Two distinct endothelin receptors, designated $ET_A$ and $ET_B$, have been identified and there is evidence that other subtypes exist (see, e.g., Emori et al. (1990) *FEBS Lett.* 263:261–264; and Sokolovsky et al. (1992) *J. Biol. Chem.* 267:20551–20554). DNA clones encoding the $ET_A$ and $ET_B$ receptors have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain.

The distribution of receptor subtypes is tissue specific (Martin et al. (1989) *Biochem. Biophys. Res. Commun.* 162: 130–137) and the affinity of each receptor for members of the endothelin family of peptides can be distinguished. $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lett.* 282: 103–106) and have been associated with bronchoconstrictive disorders. The $ET_A$ receptor appears to mediate the principal part of the vasoconstriction induced by ET-1 (Ihara et al. (1993) *Lif. Sci* 50:247–255) and the $ET_B$ subtype mediates endothelium-dependent vasodilation (Takayanagi et al. (1991) *FEBS Lett.* 282:103–106), Selective agonist-induced stimulation of $ET_B$, however, can induce vasoconstriction (see, e.g., MCMurdo et al. (1993) *Br. J. Pharmac.* 108:557–561; and Moreland et al. (1992) *Biochem. Biophys. Res. Commun.* 184:100–106).

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states. Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels are as high as 35 pg/ml have been observed (see, Stewart et al. (1991 ) *Annals Internal Med.* 114: 464–469). Because endothelin is likely to be a local, rather than a systemic, regulating factor, it is probable that the levels of endothelin at the endothelium/smooth muscle interface are much higher than circulating levels.

Endothelin agonists and antagonists

Because endothelin is associated with certain disease states and is implicated in numerous physiological effects, compounds that can interfere with or potentiate endothelin-associated activities, such as endothelin-receptor interaction and vasoconstrictor activity, are of interest. A number of compounds that exhibit endothelin antagonistic activity have been identified. These include cyclic pentapeptides, acyltripeptides, hexapeptide analogs, certain antraquinone derivatives, indanecarboxylic acids, certain N-pyriminyl-benzenesulfonamides, certain benzenesulfonamides, and certain naphthalenesulfonamides (Nakajima et al. (1991) *J. Antibiot.* 44:1348–1356; Miyata et al. (1992) *J, Antibiot.* 45:74–8; Ishikawa et al. (1992) *J. Med. Chem.* 35:2139–2142; U.S. Pat. No. 5,114,918 to Ishikawa et al.; EP A10 569 193; EP A10 558 258; EP A10 436 189 to BANYU PHARMACEUTICAL CO., LTD (Oct. 7, 1991); Canadian Patent Application 2,067,288; Canadian Patent Application 2,071,193; U.S. Pat. No. 5,208,243; U.S. Pat. No. 5,270,313; Cody et al. (1993) *Med. Chem. Res.* 3:154–162; Miyata et al. (1992) *J. Antiblot* 45:1041–1046; Miyata et al. (1992) *J. Antibiot* 45:1029–1040, Fujimoto et al. (1992) *FEBS Lett.* 305:41–44; Oshashi et al. (1002) *J. Antiblot* 45:1684–1685; EP A10 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444).

In particular, a fermentation product of *Streptomyces misakiensis,* designated BE-18257B, has been identified as an ET$_A$ receptor antagonist. BE- 18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner (IC$_{50}$ 1.4 μM in aortic smooth muscle, 0.8 μM in ventricle membranes and 0.5 μM in cultured aortic smooth muscle cells), but fails to inhibit binding to receptors in tissues in which ET$_B$ receptors predominate at concentrations up to 100 μM. Cyclic pentapeptides related to BE-18257B, such as cyclo(D-Asp-Pro-D-Val-Leu-D-Trp) (BQ-123), have been synthesized and shown to exhibit activity as ET$_A$ receptor antagonists (see, U.S. Pat. No. 5,114,918 to Ishikawa et al.; see, also, EP A10 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to ET$_A$ receptors.

Development of non-peptidic ET antagonists has also become an important objective. Screening of several thousands of compounds from a chemical library for the ability to inhibit ET-1 binding to a human placental membrane preparation, identified a class of pyrimidinyl sulfonamides that weakly inhibit ET-1 binding. Modifications of these compounds led to the identification of a pyrimidinyl sulfonamide that inhibits ET-1 binding to ET$_A$ receptors at IC$_{50}$ concentrations of about 0.2 μM and to ET$_B$ receptors at concentrations of about 1 μM (see, e.g., Canadian Patent Application 2,067,288; Canadian Patent Application 2,071,193; U.S. Pat. No. 5,208,243; and Clozel et al. (1993) *Nature* 365:759–761). The pyrimidinyl sulfonamide also exhibits in vivo activity in recognized animal models of vasoconstriction and has been deemed promising for the therapeutic treatment of vasoconstriction (Clozel et al. Clozel et al. (1993) *Nature* 365:759–761).

Screening of other compounds led to the identification of sulfathiazole as an inhibitor of the binding of endothelin to ET$_A$ (IC$_{50}$= 69 μm; see, Stein et al. (1994) *J. Med. Chem.* 37:329–331) and sulfisoxazole (IC$_{50}$<1 μM; see, Stein et al. (1994) *J. Med. Chem.* 37:329–331 but also see, co-owned U.S. application Ser. No. 08/065,202, which is herein incorporated by reference and to which this application claims priority). Particular N-(3,4-dimethyl- 5-isoxazolyl)naphthalene-1-sulfonamides were shown to have endothelin antagonist activity. One derivative 5-diemthylamino-N-(3,4-dimethyl- 5-isoxazolyl)naphthalene-1-sulfonamide is reported to have an IC$_{50}$ value of 150 nM for inhibiting endothelin binding to ET$_A$ receptors and appears to exhibit oral activity in a rat model (see, Stein et al., 1994) *J. Med. Chem.* 37:329–331).

Endothelin antagonists and agonists as therapeutic agents

In view of the numerous physiological effects of endothelin and its apparent association with certain diseases, endothelin is believed to play a critical role in pathophysiological conditions, including hypertension, atherosclerosis, other vascular disorders, gastrointestinal disorders, renal failure, asthma, pulmonary hypertension, ischemia, coronary vasospasm, cerebral vasospasm and others (see, e.g., Saito et al. (1990) *Hypertension* 15: 734–738; Tomita et al. (1989) *N. Engl. J. Med.* 321:1127; Doherty (1992) *J. Med. Chem.* 35:1493–1508; Morel et al. (1989) *Eur. J. Pharmacol.* 167: 427–428). Because endothelin is associated with these and other disease states, more detailed knowledge of the function and structure of the endothelin peptide family should provide insight in the progression and treatment of such conditions.

To aid in gaining this understanding and to exploit the potential of endothelin as a therapeutic target, there is a need to identify additional compounds that modulate or alter endothelin activity. Compounds that modulate endothelin activity, particularly compounds that act as specific antagonists or agonists, may not only aid in elucidating the function of endothelin, but may be therapeutically useful. In particular, compounds that specifically interfere with the interaction of endothelin peptides with the ET$_A$, ET$_B$ or other receptors should may aid in the design of therapeutic agents, and may be useful as disease specific therapeutic agents.

Therefore, it is an object herein to provide compounds that have the ability to modulate the biological activity of one or more of the endothelin isopeptides, It is another object to provide compounds that have use as specific endothelin antagonists. It is also an object to use compounds that specifically interact with or inhibit the interaction of endothelin peptides with ET$_A$ or ET$_B$ receptors as therapeutic agents for the treatment of endothelin-mediated diseases and disorders.

SUMMARY OF THE INVENTION

Sulfonamides and methods for modulating the interaction of an endothelin peptide with ET$_A$ and/or ET$_B$ receptors are provided. In particular, sulfonamides and methods for inhibiting the binding of an endothelin peptide to ET$_A$ or ET$_B$ receptors. Sulfonamides and methods using the sulfonamides that act as endothelin agonists with respect to ET$_A$ or ET$_B$ receptors are also provided.

The methods are effected by contacting the receptors with one or more sulfonamides prior to, simultaneously with, or subsequent to contacting the receptors with an endothelin peptide. The sulfonamides are substituted or unsubstituted, aliphatic, monocyclic or polycyclic aromatic or heteroaromatic sulfonamides, such as benzene sulfonamides and naphthalene sulfonamides, and thiophene sulfonamides.

The sulfonamides have formula I:

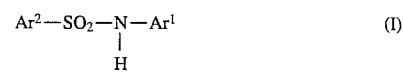

in which Ar$^1$ is a substituted or unsubstituted aryl group with one or more substituents, including an alkyl group, an aryl group, a substituted aryl group, a nitro group, an amino group or a halide or is an alkyl group. In particuarl, Ar$^1$ is alkly or is a five or six membered substituted or unsubstituted aromatic or heteroaromatic ring, including, 3- or 5-isoxazolyl, 2-thiazolyl, 2-pyrimidinyl, pyrazolyl, 3- or 5-isothiazolyl, pyrazinyl, or substituted benzene group, including aryloxy substituted benzene groups or is fused aliphatic or heteroaliphatic ring containing from 6 to about 21 carbons in the ring structure, such as bicyclic or tricyclic rings, including naphthyl groups, quinolyl groups, dibenzofuryl groups, dibenzopyrrolyl groups, dibenzothiophenyl groups, purines, and phenanthrenes.

Ar$^1$ is, in certain embodiments, selected from groups such as:

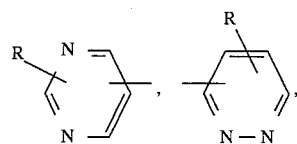

-continued

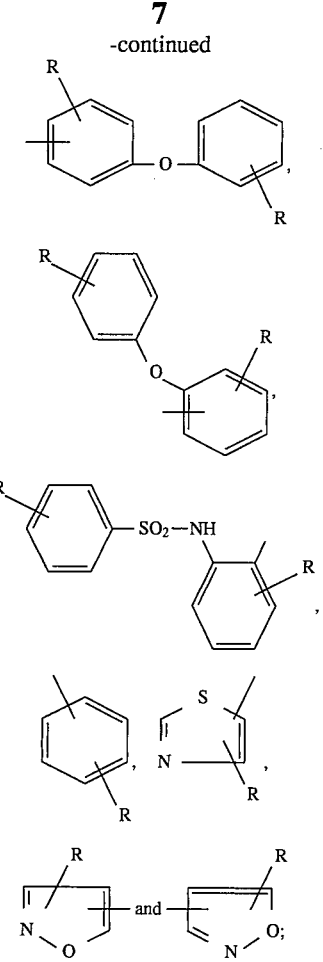

that is substituted with one or more substituents selected from R. R is selected from H, NH₂, halide, pseudohalide, alkyl alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions are unsubstituted or substituted with any of the preceding groups, and unsubstituted or substituted with any of the preceding groups, and straight or branched chains of from about 1 up to about 10–12 carbons, preferably, 1 to about 5 or 6 carbons. R is preferably H, NH₂, halide, CH₃, CH₃O or another aromatic group.

Ar² is any group such that the resulting sulfonamide inhibits binding by 50%, compared to binding in the absence of the sulfonamide, of an endothelin peptide to an endothelin receptor at a concentration of less than about 100 μM, except that Ar² is not phenyl or naphthyl when Ar¹ is N-(5-isoxazolyl) or N-(3-isoxazolyl) unless the isoxazole is a 4-halo-isoxazole or, if enhanced $ET_B$ affinity is desired, a 4-higher alkyl-isoxazole, and when Ar² is phenyl it is not substituted at the para position with NH₂, NO₂, CH₃, OH or a substituted amine.

Selected isoxazolyl-benzenesulfonamides and isoxzolyl-naphthalenesulfonamides in, which the isoxazole is other than a 4-halo-isoxazole are also provided. Such selected compounds, including N-isoxazolylbenzenesulfonamides and N-isoxazolylnaphthalenesulfonamides in which the substituent at the 4 position on the isoxazolyl group is higher alkyl, such as $C_9H_{19}$ to $C_{13}H_{27}$ are also provided. These compounds enhanced $ET_B$ affinity compared to corresponding compounds in which the substituent at the 4 position is lower alkyl or other groups, such as pseudohalide, halide, alkylaryl, aryl, lower alkyl, carboxamide, alkoxy, and others.

Thus, Ar² is selected from among alkyl, including straight and branched chains, aromatic rings, fused aromatic rings and heterocyclic rings, including. 5-membered heterocycles with one, two or more heteroatoms and fused ring analogs thereof and 6-membered rings with one, two or more heteroatoms and fused ring analogs thereof. Ar², thus, includes, but is not limited to, alkyl, norboranyl, admantyl, phenyl, naphthyl, quinolyl, isoquinolyl, acridinyl, styryl, biphenyl, isoxazolyl, thiazolyl, oxazolyl, imidazole, dibenzofuryl, indolyl (dibenzopyrrolyl), dibenzothiophenyl (thianaphthalene), carbazolyl, purinyl, and phenanthryl, anthracenyl, furyl, pyrrolyl, thiophenyl, imidazolyl, oxazolyl, pyrazolyl, pyrrolidinyl, pyrrolinyl, pyridinyl, pyrimidinyl, pyrazinyl, pyradazinyl, morpholinyl, thiomorpholinyl, quniolzoliny, quniolxazinyl, phthalazinyl, cinnolinyl, phenazinyl, phenoxzainyl, phenothiazinyl, benzoxazolyl, benzimidazolyl, benzothiazolyl, and the like. In preferred embodiments herein, Ar² is phenyl, naphthyl, furyl, pyrrolyl, thiophenyl, biphenyl, and thiadazolyl.

In the embodiments described in detail herein, Ar¹ is an isoxazole and the compounds are represented by the formulae II:

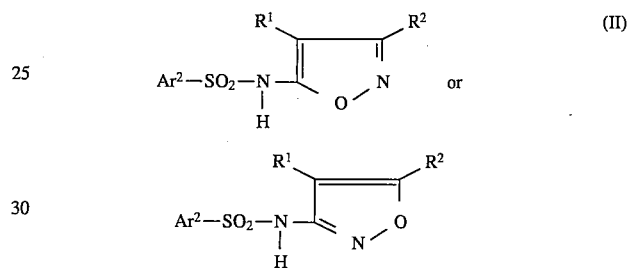

in which R¹ and R² are either (i), (ii) or (iii) as follows:

(i) R¹ and R² independently selected from H, NH₂, NO², halide, pseudohalide, alkyl, alkenyl, alkynyl, aryl, arylalkyl, heterolaryl, alkoxy, alkylamino, hydroxyalkyl, alkoxyalkyl, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, with the proviso that R² is not halide or pseudohalide; or, (ii) R¹ and R² together form $—(CH_2)_n$, where n is 3 to 6; or, (iii) R¹ and R² together form 1,3-butadienyl, and with the proviso that Ar² is not phenyl or naphthyl unless R¹ is a halide or a higher alkyl, particularly $C_9H_{19}$ to $C_{13}H_{27}$.

In preferred embodiments herein, R¹ is selected from alkyl, lower alkenyl, lower alkynl, lower haloalkyl, halide, and pseudohalide; and R² is selected among lower alkyl, lower alkenyl, lower alkynl and lower haloalkyl.

Ar² is any group such that the resulting sulfonamide inhibits binding by 50%, compared to binding in the absence of the sulfonamide, of an endothelin peptide to an endothelin receptor at a concentration of less than about 50 μM, except that Ar² is not phenyl or naphthyl unless the compound is an N-isoxazolylsulfonamide substituted at the 4-position on the isoxazolyl group with halide or higher alkyl, particularly $C_9H_{19}$ to $C_{13}H_{27}$.

In particular, Ar¹ is an isoxazolyl group, and Ar² is an aliphatic straight or branched carbon chain, including alkyl, alkenyl, and alkynyl groups, heterocycle, with one or more, generally one to three rings, or is a group or isomer group selected, with the proviso that $Ar^2$ is not phenyl or naphthyl, unless $R^1$ (the 4-substituent on the isoxazolyl group (AH)) is a halide or a higher alkyl, with greater than 8 carbons, preferably $C_9H_{19}$ to $C_{13}H_{27}$. $Ar^2$ is in certain embodiments selected from among groups including: alkyl,

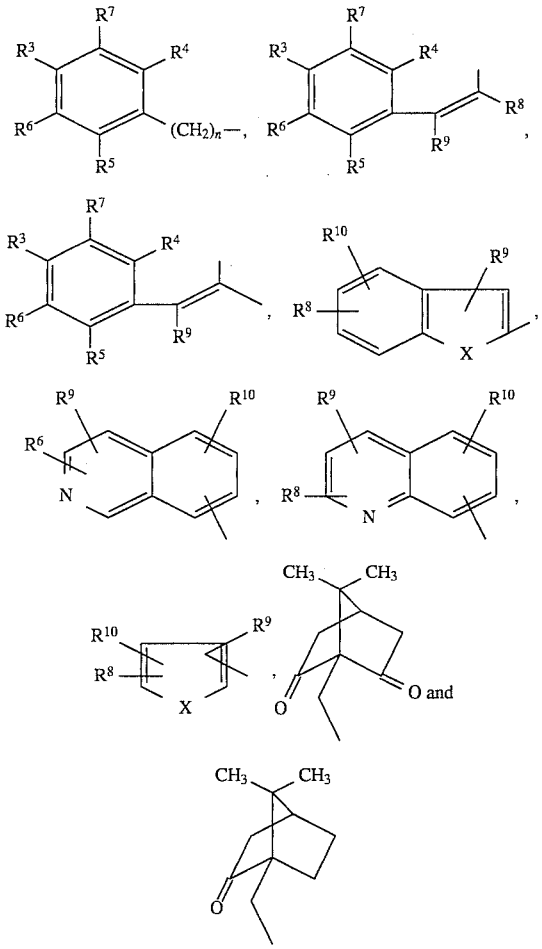

in which n is 0 to 10, preferably 0 to 6, more preferably 0 to 3, X is O, S or $NR^{11}$, where $R^{11}$, which is hydrogen or contains up to about 30 carbon atoms, generally 1 to 16 carbon atoms, and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which is halide, pseudoahlide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR_{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{11}$, $R^{12}$, $R^{15}$ and $R^{16}$ may be further substituted with the any of the groups set forth for Z;

$R^3$, $R^4$, $R^5$, $R^6$ and $R^7$ are each selected independently from (i)–(iv), with the proviso that, when $Ar^2$ is phenyl (a) at least one of $R^3$, $R^4$, $R^5$, $R^6$, and $R^7$ is not hydrogen and (b) when $Ar^1$ is 3-isoxazolyl, $R^3$ is not $NH_2$ or $CH_3$;

(i) $R^3$, $R^4$, $R^5$, $R^6$ and $R^7$ are each selected independently from among H, NHOH, $NH_2$, $NO_2$, $N_3$, aminoalkyl, alkylamino, dialkylamino, carboxyl, carbonyl, hydroxyl, halide, pseudohalide, alkyl, alkenyl, alkynyl, aryl, heterocycle, alkoxy, alkylthio, alkoxyalkyl, alkylsulfinyl, alkylsulfonyl, aryloxy, arylalkoxy, aryloxy, arylamino, arylthio, arylsulfinyl, arylsulfonyl, haloalkyl, haloaryl, haloalkoxy, alkoxycarbonyl, alkylcarbonyl, arylcarbonyl, formyl, substituted or unsubstituted amido, substituted or unsubstituted ureido in which each of the preceding groups may be unsubstituted or substituted with groups such as H, $NH_2$, $NO_2$, alkyl, halide, and pseudohalide; or, alternatively, (ii) $R^4$ and $R^7$ together are substituted or unsubstituted 1,3-butadienyl, 1-chloro-1,3-butadienyl, 4-dimethylamino-1,3-butadienyl, 1-aza-1,3-butadienyl or 2-aza-1,3-butadienyl groups; and $R^3$, $R^5$ and $R^6$ are as defined in (i) above; or alternatively, (iii) $R^7$ and $R^3$ together are substituted or unsubstituted 1,3-butadienyl, 4-dimethylamino-1,3 butadienyl, 1-chloro-1,3-butadienyl, 1-aza-1,3-butadienyl or 2-aza-1,3-butadienyl groups; and $R^4$, $R^5$ and $R^6$ are as defined in (i) above; or alternatively, (iv) $R^3$, $R^5$, and $R^7$ are H; and $R^4$ and $R^6$ are each independently selected from alkyl, alkoxy, halide, amino and aminoalkyl; and $R^8$, $R^9$, $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide pseudohalide, alkyl, alkoxy, alkenyl, alkynyl, aryl, aryloxy, heterocycle, aralkyl, aralkoxy, cycloalkyl, cycloalkenyl cycloalkynyl, OH, CN, $C(O)R^{18}$, $CO_2R^{18}$, SH $S(O)_nR^{18}$ in which n is 0–2, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for $R^8$, $R^9$ and $^{10}$ are unsubstituted or substituted with any substituents set forth for Z, which is halide, pseudoahlide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, allynyl, aryl, alkylaryl, heterocycle, aralkyl, alkoxy, aralkoxy, cycloalkyl, cycloakenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl; or (ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, preferably 3 to about 10 members, more preferably 5 to 7 members that is unsubstituted or substituted with one or more substituents in each each substituent is independently selected from Z; and the other of $R^8$, $R^9$ and $R^{10}$ is selected as in (i).

In the above embodiments, the alkyl, alkyny and alkenyl portions of each listed substituent are straight or branched chains, acyclic or cyclic, and preferably have from about 1 up to about 10 carbons; in more preferred embodiments they have from 1–6 carbons, and they can have fewer than 6 carbons. The aryl, alicyclic, aromatic rings and heterocyclic groups can have from 3 to 16, generally, 3–7, more often 5–7 members in the rings, and may be single or fused rings. The ring size and carbon chain length are selected up to an amount that the resulting molecule binds to retains activity as an endothelin antagonist or agonist, such that the resulting compound inhibits binding by 50%, compared to binding in the absence of the sulfonamide, of an endothelin peptide to an endothelin receptor at a concentration of less than about 50 µM, preferably less than about 10 µM.

Thus, $Ar^2$ is a substituted or unsubstituted group selected from among groups such as the following: naphthyl, phenyl, biphenyl, quinolyl, styryl, thiophenyl, furyl, isoquinolyl, pyrrolyl, benzofuranyl, benzothiophenyl, benzopyrrolyl, pyridinyl, thianaphthalyl, indolyl, dibenzofuranyl, dibenzopyrrolyl, dibenzothiophenyl, phenanthryl, thiazolyl, isoxazolyl, anthacenyl, alkenyl, alkynl and alkyl. It is understood that the positions indicated for substituents, including the sulfonamide groups, may be varied. Thus, for example, compounds herein encompass groups that include thiophene-3-sulfonamides and thiophene-2-sulfonamides.

In embodiments described in detail herein, $Ar^1$ is isoxazolyl. In all embodiments, 4-haloisoxazolyl or 4-methylisoxzaolyl are preferred, except when $Ar^2$ is phenyl or naphthyl, then 4-haloisoxazolyl and 4-higher alkylisoxzaolyl are preferred. In general, 4-haloisoxazolyl sulfonamides exhibit substantially enhanced activity with respect to at least one of the ET receptors (about two-fold to twenty-fold greater activity), as assessed by assays, such as those provided herein, that measure binding to $ET_A$ and/or $ET_B$ receptors, compared to corresponding sulfonamides in which the substituent at the 4 position in the isoxazolyl is other than halo, such as alkyl. For example: (1) the $IC_{50}$ for competitive of inhibition of binding of ET-1 to $ET_A$ receptors of 2,5-dimethyl-N-( 3,4-dimethyl-5-isoxazolyl)benzenesulfonamide to is 9.4 µM; whereas the $IC_{50}$ for 2,5-dimethyl-N-(4-chloro-3-methyl-5-isoxazolyl)benzenesulfonamide is 0.19 µM and for 2,5-dimethyl-N-(4-bromo-3-methyl-5-isoxazolyl)benzenesulfonamide is 0.044 µM (see, e.g., TABLE 1, below); (2) the $IC_{50}$ of N-(3,4-dimethyl- 5-isoxazolyl)-2-biphenylsulfonamide for $ET_A$ receptors is about 0.008 µM, whereas, the $IC_{50}$ of N-(4-bromo-3-methyl-5-isoxazolyl)-2-biphenylsulfonamide is about 0.0016 µM (see, Table 2); and (3) the $IC_{50}$ of N-(3,4-dimethyl- 5-isoxazolyl)-3-biphenylsulfonamide for $ET_B$; receptors is about 3.48 µM; whereas, the $IC_{50}$ of N-( 4-bromo-3-methyl-5-isoxazolyl)-3-biphenylsulfonamide for $ET_B$ receptors is about 0.76 µM and the $IC_{50}$ of N-(4-chloro-3-methyl-5-isoxazolyl)-3-biphenylsulfonamide for $ET_B$ receptors is about 0.793 µM (see, Table 2).

Other selected compounds include benzene and naphthalene isoxazole sulfonamides in which the 4 position on the isoxazole ring of $Ar^1$ is a methyl group and the 3 position is a relatively long chain (greater than about 8 carbons up to about 15 carbons, preferably about 13 carbons) alkyl group. Such compounds, although reportedly exhibiting a loss in affinity to $ET_A$ receptors (see, Stein et al. (1994) *J. Med. Chem.* 37:329–331), are herein shown to exhibit increased affinity to $ET_B$ receptors compared to compounds in which the group at the 3 position is a methyl group.

In certain preferred embodiments herein, $R^{11}$ is aryl, such as phenyl or alkyl phenyl, hydrogen or lower alkyl, and $R^8$, $R^9$, $R^{10}$ are independently selected from hydrogen, halide, lower alkyl, lower aryl, lower heterocycle, lower aralkyl, $C(O)_2R^{18}$, $CO_2R^{18}$, $NO_2$, $OR^{18}$ $SR^{18}$, $NR^{18}COR^{19}$ or $CONR^{19}R^{18}$; $R^{18}$ and $R^{19}$ are preferably hydrogen, lower alkyl, and lower aryl, and Z is hydrogen, halide, pseudohalide, lower alkyl, lower alkoxy or pseudohalo- or halo(lower)alkyl. In certain more preferred embodiments, $R^8$ and $R^{10}$ are hydrogen, halide or methyl, more preferably hydrogen or halide, and $R^9$ is selected independently from hydrogen, halide, aryl, pseudohalide and lower alkyl, preferably methyl or ethyl, $COR^{18}$, $CONR^{18}R^{19}$ and $NR^{18}COR^{19}$.

In the preferred compounds herein, $R^2$ is preferably, selected from among alkyl, lower alkenyl, lower alkynl, lower haloalkyl or H; and $R^1$ is halide, lower alkyl or lower haloalkyl, and more preferablly, $R^1$ is bromide, chloride, methyl or ethyl. In the most active compounds provided herein, as evidenced by in vitro binding assays, $R^1$ is bromide or chloride.

In preferred embodiments herein, the compounds have formula II in which $R^1$ is halide or methyl, $R^2$, $Ar^2$, $R^3$, $R^5$, $R^6$, $R^8$, $R^9$, $R^{10}$ and $R^{11}$ are as defined above. In most preferred embodiments, $R^1$ is bromide. Thus, in general, the most preferred compounds herein, particularly with respect to $ET_A$ affinity, are N-(4-bromoisoxazolyl)sulfonamides. Compounds in which $R^1$ is methyl and $Ar^2$ is other than phenyl or naphthyl are also preferred.

Preferred compounds also include compounds that are $ET_B$ receptor selective or that bind to $ET_B$ receptors with an $IC_{50}$ of less than about 1 µM. In these compounds, $Ar^2$ is 3-biphenyl, 4-biphenyl, certain compounds in which $Ar^2$ phenanthrene or is a 5-membered heterocycle, particularly thiophenyl, compounds in which $Ar^2$ is naphthyl and phenyl and $R^1$ is higher alkyl ($C_9H_{19}$ to $C_{13}H_{27}$), $R^2$ is selected from among alkyl, lower haloalkyl, H; and $R^1$ is halide, lower alkyl or lower haloalkyl, or, when $Ar^2$ is phenyl or naphthyl, $R^1$ is higher alkyl (nine or more carbon atoms, preferably 9 to 13 carbon atoms). The 5-membered heterocyclic compounds that exhibit $ET_B$ affinity or selectivity are those in which $R^9$ and $R^{10}$ are selected independently from hydrogen, lower alkyl, preferably methyl or ethyl, or halide, and $R^8$, which is the substituent at the 5-position (see, e.g., the formulae setting forth the numbering for the 5-membered heterocyclic ring compounds), is aryl or a heterocycle, particularly phenyl and isoxazolyl, which are unsubstituted or substituted with Z, which is preferably lower alkyl or halide.

Of the compounds described herein, those that inhibit or increase an endothelin-mediated activity by about 50% at concentrations of less than about 10 µM are preferred. More preferred are those that inhibit or increase an endothelin-mediated activity by about 50% at concentrations of less than about 1 µM, more preferably less than about 0.1 µM, even more preferably less than about 0.01 µM, and most preferably less than about 0.005 µM.

Also among the most preferred compounds for use in methods provided herein, are those that are $ET_A$ selective, i.e., they interact with $ET_A$ receptors at concentrations at substantially lower concentratons (at an $IC_{50}$ at least about 10-fold lower, preferably 100-fold lower) than they interact with $ET_B$ receptors. Other preferred compounds are $ET_B$ selective. These compounds interact with $ET_B$ receptors at $IC_{50}$ concentrations that are at least about 10-fold lower than the concentrations at which they interact with $ET_A$ receptors. In particular, compounds that interact with $ET_A$ with an $IC_{50}$ of less than about 10 µM, preferably less than 1 µM, more preferably less than 0.1 µM, but with $ET_B$ with an $IC_{50}$ of greater than about about 10 µM or compounds that interact with $ET_B$ with an $IC_{50}$ of less than about 10 µM, preferably less than 1 µM, more preferably less than 0.1 µM, but with $ET_A$ with an $IC_{50}$ of greater than about 10 µM are preferred.

Among others of the preferred compounds for use in the methods herein are any compounds that interact with $ET_A$ and/or $ET_B$ receptors with an $IC_{50}$ of less than about 10 µM, more preferably less than 1 µM, even more preferably less than about 0.1 µM, even more preferably less than about 0.01 µM and most preferably less than about 0.005 µM.

Pharmaceutical compositions formulated for administration by an appropriate route and means containing effective concentrations of one or more of the compounds provided :herein or pharmaceutically acceptable salts or acids thereof that deliver amounts effective for the treatment of hypertension, stroke, asthma, shock, ocular hypertension, glaucoma, renal failure, inadequate retinal perfusion and other conditions that are in some manner mediated by an endothelin peptide or that involve vasoconstriction or whose symptoms can be ameliorated by administration of an endothelin antagonist or agonist, are also provided. Particularly preferred compositions are those that deliver amounts effective for the treatment of hypertension or renal failure. The effective amounts and concentrations are effective for ameliorating any of the symptoms of any of the disorders.

Methods for treatment of endothelin-mediated disorders, including but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, ischemia, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided. Preferred methods of treatment are methods for treatment of hypertension and renal failure.

More preferred methods of treatment are those in which the compositions contain at least one compound that inhibits the interaction of endothelin-1 with $ET_A$ receptors at an $IC_{50}$ of less than about 10 µM, and preferably less than about 5 µM, more preferably less than about 1 µM, even more preferably less than 0.1 µM, and most preferably less than 0.05 µM Other preferred methods are those in which the compositions contain one or more compounds that is (are) $ET_A$ selective or one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of compositions containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, ischemia, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 µM, within the packaging material, and a label that indicates that the compound or salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, ischemia, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assess by the ability to interfere with endothelin-induced vasoconstriction.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (1989) *J. Cardiovasc. Pharmacol.* 13(Suppl. 5):S191S- 192; Spinella et al. (1991) *Proc. Natl. Acad. Sci. USA* 88: 7443–7446; Cardell et al. (1991 ) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 50–100-fold lower with respect to $ET_A$ receptors than $ET_B$ receptors.

As used herein, a suffonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388–392). For example, succinyl-sulfathiazole is a prodrug of 4-amino-N-(2-thiazoyl)benzenesulfonamide (sulfathiazole) that exhibits altered transport characteristics.

As used herein, "halogen" or "halide" refers to F, Cl, Br or I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate and azide.

As used herein, alkyl, alkenyl and alkynyl refer to straight or branched carbon chains, which may be unsubstituted or substituted, having from 1 to about 24 carbons, preferably 1 to about 10 carbons, more preferably, 1 to 7 carbons. Thus, for example, alkyl includes straight chains, branched chains, and substituted carbon chains, including as benzyl and camphor groups.

As used herein, lower alkyl, lower alkenyl, and lower alkynyl refer to carbon chains having less than about 6 carbons. In preferred embodiments of the compounds provided herein that include alkyl, alkenyl, or alkynyl portions include lower alkyl, lower alkenyl, and lower alkynyl portions.

As used herein, aryl refers to aromatic cyclic groups containing from 3 to 15 or 16 carbon atoms, preferably from 5 to 10. Aryl groups include, but are not limited to groups, such as phenyl, substituted phenyl, napthyl, substituted naphthyl, in which the substitunent is lower alkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic.

As used herein, alicyclic refers to alkyl groups that are cyclic.

As used herein, "haloalkyl" refers to a lower alkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO- in which R is a haloalkyl group.

As used herein, "aminocarbonyl" refers to —C(O)NH$_2$.

As used herein, "alkylaminocarbonyl" refers to —C(O)NHR in which R is hydrogen, alkyl, preferably lower alkyl or aryl, preferably lower aryl.

As used herein "dialkylaminocarbonyl" as used herein refers to —C(O)NR'R in which R' and R are independently selected from alkyl or aryl, preferably lower alkyl or lower aryl.

As used herein, "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO- and RS-, in which R is alkyl, preferably lower alkyl; and "aryloxy" and "arylthio", aryloxy or aryl, RO- and RS- in which R is aryl, preferably lower aryl.

As used herein, cycloalkyl refers to satured cyclic carbon chains; cycloalkyenyl and cycloalkynyl refer to cyclic carbon chains that include at least one unsaturated double or triple bond, respectively. The cyclic portions of the carbon chains may include one ring or two or more fused rings.

As used herein, heterocycle or heteroaryl refers to ring structures that include at least one carbon atom and one or more atoms, such as N, S and O. The rings may be single rings or two or more fused rings.

As used herein, the abbreviations for any protective groups, amino acids and other compounds, are, unless indicated otherwise, in accord with their common usage, recognized. abbreviations, or the IUPAC-IUB Commission on Biochemical Nomenclature (see, (1972) *Biochem.* 11:1726).

A. Compounds for use in treating endothelin-mediated diseases

Compounds and methods for treating endothelin-mediated diseases using the compounds of formula I are provided. In particular, the compounds provided herein have formulae II in which Ar$^2$ is selected from groups including, but not limited to: alkyl; phenyl; biphenyl; dibenzofuryl; dibenzothiophenyl; carbazolyl; naphthyl; thiophenyl; furyl; pyrrolyl; isoguinolyl; quinolyl; phenanthryl; styryl; pyridinyl; and heterocycle with two or more heteroatoms, including heterocycles with one ring or two or more fused rings containing up to about 30, generally 1 to 14, carbon atoms in the ring structure.

1. Isoxazolylsulfonamides in which Ar$^2$ is phenyl, biphenyl and fused aromatic rings Compounds in which Ar$^2$ is selected from phenyl, biphenyl, and aromatic fused rings, including naphthyl, anthracenyl, phenanthryl, indenyl, azulenyl, fluorenyl, and phenazinyl. When Ar$^2$ is phenyl, biphenyl or naphthyl, the compounds are preferably (4-halo-isoxazolyl)sulfonamides or are (4-higher alkylisoxazolyl)sulfonmides, in which the alkyl group contains more than about 8, preferably 9 to 15, more preferably 9 to 13, carbon atoms. These compounds have the formulae (III):

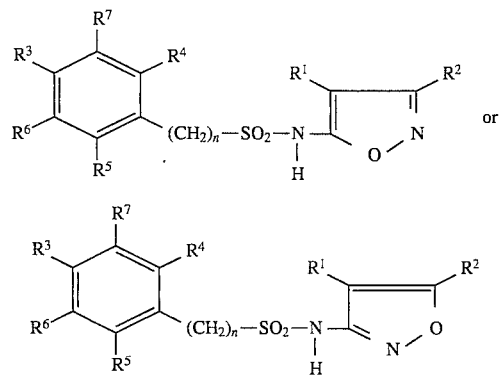

in which n is 0 to 1 0, preferably 0 to 6, more preferably 0 to 3; R$^3$, R$^4$, R$^5$, R$^6$, and R$^7$ are selected from (i), (ii), (iii) or (iv) with the proviso that: (a) when Ar$^2$ is phenyl, at least one of R$^3$, R$^4$, R$^5$, R$^6$, and R$^7$ is not hydrogen, (b) when Ar$^1$ is 4-halo- 5-methyl-3-isoxazolyl, R$^3$ is not NH$_2$ or CH$_3$, and (c) when Ar$^2$ is phenyl, napthyl or 2-biphenyl, R$^1$ is halide or higher alkyl:

(i) R$^3$, R$^4$, R$^5$, R$^6$, and R$^7$ are each selected independently from among H, NHOH, NH$_2$, NO$_2$, N$_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons and the aryl portions contain from 3 up to about 10 carbons, preferably 6 carbons; or, alternatively, (ii) R$^4$ and R$^7$ together are substituted or unsubstituted 1,3-butadienyl, 4-dimethylamino- 1,3 butadiene, 1-chloro-1,3-butadiene, 1-aza-1,3-butadienyl or 2-aza- 1,3-butadienyl groups; and R$^3$, R$^5$ and R$^6$ are as defined in (i) above; or alternatively, (iii) R$^7$ and R$^3$ together are substituted or unsubstituted 1, 3-butadienyl, 4-dimethylamino-1,3 butadiene, 1-chloro-1,3- butadiene, 1-aza-1,3-butadienyl or 2-aza-1,3-butadienyl groups; and n, X, $R^4$, $R^5$ and $R^6$ are as defined in (i) above; or (iv) $R^3$, $R^5$, and $R^7$ are H are as defined in (i); and $R^4$ and $R^6$ are each independently selected from alkyl, alkoxy, halide aminoalkyl, dialkylaminoalkyl, in which the alkyl and alkoxy groups contain from 1 to 10, preferably 1 to 6 carbons, and are straight or branched chains.

In more preferred embodiments, $R^2$ is H, $CH_3$, $C_2H_5$; $R^1$ is Cl, Br or $CH_3$; X is O or S; n is 0 or 1; and $R^3$, $R^4$, $R^5$, $R^6$, $R^7$, are selected from either (i), (ii), (iii) or (iv) as follows:

(i) $R^5$ and $R^6$ are H; $R^4$ and $R^7$ are each independently selected from H, halide, $NH_2$, $CF_3$, Ph, $CH_3$; and $R^3$ is selected from H, NHOH, $NH_2$, $EtNH_2$, $(CH_3)_2NH$, $Ph$-$CH_2NH$, $NO_2$, F, Cl, Br, I, CN, $CH_3$, $(CH_3)_3C$, $C_5H_{11}$, $CH_3O$, n-$C_4H_9O$, $CH_2$=CH, Ph- CH=CH, CH≡C, Ph-CH≡C, Ph, 3-(ethyoxycarbonylmethyl)ureido, and 3-cyclohexylureido; or (ii) $R^4$ and $R^7$ together form 1, 3-butadienyl, 4-chloro-1, 3-butadienyl, 4-dimethylamino-1,3-butadienyl or 1-aza-1,3-butadienyl; and $R^3$, $R^5$ and $R^6$ are defined as in (i) of this embodiment; or (iii) $R^7$ and $R^3$ together form 1,3-butadienyl, 3-chloro-1, 3-butadienyl 4-dimethylamino-1,3-butadienyl or 1-aza-1,3-butadienyl; and $R^4$, $R^5$ and $R^6$ are as defined in (i) of this embodiment; or (iv) $R^3$, $R^5$, and $R^7$ are H as defined in (i) ; and $R^4$ and $R^6$ are each independently selected from alkyl, alkoxy, halide, amino alkyl, alkylaminoalkyl or dialkylaminoalkyl, in which the alkyl and alkoxy groups contain from 1 to 10, preferably 1 to 6 carbons, and are straight or branched chains.

More preferred among the above compounds are those in which $Ar^2$ is a substituted or unsubstituted phenyl or naphthyl; $R^1$ is Br, Cl or I; $R^2$ is H, $CH_3$, $C_2H_5$, $CF_3$, $C_2F_5$, n-$C_3H_7$, cyclo$C_3H_5$, and $C_4H_8$; and $R^3$, $R^4$, $R^5$, $R^6$ and $R^7$ are either (i), (ii), (iii), (iv) or (v):

(i) $R^5$, $R^6$ and $R^7$ are H; n is 0 and $R^3$ is H, $NH_2$, $CH_3$ $CF_3$, halide, $C_2H_5NH$ or Ph, $R^4$ is H, $CF_3$, $NH_2$, $R^7$ is H or $CF_3$, and $R^5$ and $R^6$ are H; or (ii) $R^3$, $R^5$ and $R^6$ are H; n is 0 and $R^4$ and $R^7$ together form 1,3-butadienyl, 4-dimethylamino-1,3 butadienyl, 1-chloro- 1,3-butadiene, or 4-chloro-1,3-butadienyl; or (iii) $R^4$, $R^5$ and $R^6$ are H; n is 0; and $R^7$ and $R^3$ together form 1,3-butadienyl, 4-dimethylamino-1,3 butadienyl, 1-chloro- 1,3-butadiene, 1-aza-1,3-butadienyl; or (iv) $R^4$ is H or $NH_2$, $R^5$ and $R^6$ are H; n is 1 and $R^3$ is H, $NH_2$ and halide; $CH_3$, Br, Cl, F, $CF_3$, $NH_2$, $R^7$ is H, $CH_3$, Br, Cl, F, $NH_2$ or $CF_3$, and $R^5$ and $R^6$ are H; or (v) $R^3$, $R^5$, and $R^7$ are H are as defined in (i); and $R^4$ and $R^6$ are each independently selected from alkyl groups that contain from 1 to 6 carbons, and are straight or branched chains, lower alkoxy, and halide.

In more preferred embodiments, the benzenesulfonamides and naphthalenesulfonamdies are N-(4-halo)-substituted N-isoxazolylsulfonamides or are 4-higher alkyl-substituted N-isoxazolylsulfonamides, in which $R^2$ is H, $CH_3$, $C_2H_5$, $C_2F_5$ or $CF_3$; and $R^3$, $R^4$, $R^5$, $R^6$ and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5NH_2$, $(CH_3)_2NH$, Ph-CH$_2NH$, $NO_2$, F, Cl, Br, I, CN, $CH_3$, $(CH_3)_3C$, $C_5H_{11}$, $CH_3O$, n-$C_4H_9O$, $CH_2$=CH, Ph-CH=CH, CH≡C, Ph-CH≡C, Ph, 3-(ethyoxycarbonylmethyl)ureido, and 3-cyclohexylureido; or (ii) $R^3$, $R^5$ and $R^7$ are H; and $R^4$ and $R^6$ are each an alkyl group that contains from 1 to 3 carbons, which are straight or branched chains.

In yet more preferred embodiments, $R^1$ is most preferably Br; $R^2$ is $CH_3$, $C_2H_5$, or $CF_3$; and $R^3$, $R^4$, $R^6$ and $R^7$ are (i) or (ii) as follows:

(i) $R^3$ is H, $NH_2$, $CH_3$ $CF_3$, halide or $C_2H_5NH$; $R^4$, $R^5$ and $R^6$ are independently selected from H, $CF_3$, halide, particularly Br and Cl, $NH_2$; and $R^7$ is H, $CH_3$, $CH_2CH_5$, $(CH_3)CH$, F or $CF_3$; or (ii) $R^3$, $R^5$ and $R^7$ and $R^4$ and $R^6$ are each an methyl or ethyl.

In all embodiments, $R^1$ is most preferably Br, except in instances in which ehanced $ET_B$ affinity, compared to the corresponding compound in which $R_1$ is $CH_3$, is desired, than $R^1$ is most preferably a higher alkyl (9 to 15 carbons, preferably 9 or 10 to 13 carbons).

a. Compounds in which $Ar^2$ is phenyl and biphenyl and n is 0

Compounds in which $Ar^2$ if phenyl or biphenyl have the following formulae (IV):

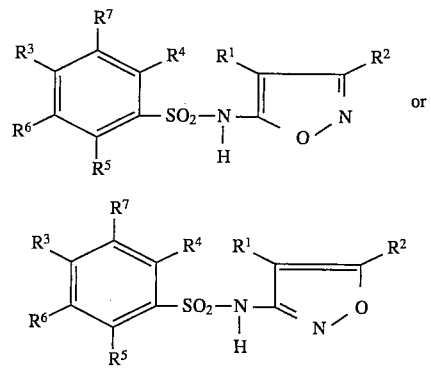

in which $R^3$, $R^4$, $R^5$, $R^6$, and $R^7$ are selected from (i), (ii), (iii) or (iv) with the proviso that, (a) when $Ar^2$ is phenyl, at least one of $R^3$, $R^4$, $R^5$, $R^6$, and $R^7$ is not hydrogen, (b) when $Ar^2$ is phenyl and $Ar^1$ is 3-isoxazolyl, $R^3$ is not $NH_2$ or $CH_3$, and (c) when $Ar^2$ is napthyl, 2-biphenyl, phenyl, other than benzofuryl, dibenzothiophenyl and dibenzopyrrolyl, $R^1$ is halide or higher alkyl:

(i) $R^3$, $R^4$, $R^5$, $R^6$, and $R^7$ are each selected independently from among H, NHOH, $NH_2$, $NO_2$, $N_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons and the aryl portions contain from 3 up to about 10 carbons, preferably 6 carbons; are each independently selected as described above; or, alternatively, (ii) $R^3$, $R^5$, and $R^7$ are H; and $R^4$ and $R^6$ are each independently selected from alkyl, alkoxy, halide aminoalkyl, dialkylaminoalkyl, which are unsubstituted or substituted with alkyl groups, wherein the alkyl and alkoxy groups contain from 1 to 10, preferably 1 to 6 carbons, and are straight or branched chains.

Among the above phenyl and biphenyl compounds, are compounds with the following formulae (V):

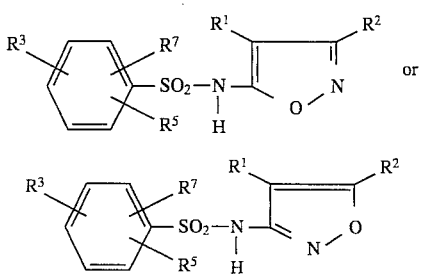

in which $R^3$, $R^5$ and $R^7$ are each independently
- (a) hydrogen, except that at least one of $R^3$, $R^5$ and $R^7$ is other than hydrogen;
- (b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$, except that if one of $R^3$, $R^5$ are $R^7$ is alkyl at the 4 position, at least one of the other two of $R^3$, $R^5$ are $R^7$ is not hydrogen;
- (c) halo;
- (d) hydroxyl;
- (e) cyano;
- (f) nitro, except that if one of $R^3$, $R^5$ and $R^7$ is 4-$NC)_2$, then at least one of the other two of $R^3$, $R^5$ and $R^7$ is not hydrogen;
- (g) —C(O)H or —C(O)$R^{27}$;
- (h) —$CO_2$H or —$CO_2R_{27}$;
- (i) —SH, —S(O)$_n$R$^{27}$, —S(O)$_m$—OH, —S(O)$_m$—OR$^{27}$, —O—S(O)$_m$OH, or —O—S(O)$_m$OR$_{27}$;
- (j) —$W^4NR^{28}R^{29}$, except that, if one of $R^3$, $R^5$ and $R^7$ is 4-$W^4NR^{28}R^{29}$ then at least one of the other two of $R^3$, $R^5$ and $R^7$ is not hydrogen; or
- (k) —$W^4N(R^{32})$—$W^5NR^{30}R^{31}$;

$R^1$ is halide or is higher alkyl (greater than about 8 carbons up to about 9 carbons in the chain;

$R^2$ is selected from:
- (a) hydrogen;
- (b) alkyl, alkenyl, alkynyl, alkoxy, cycloalkyl, cycloalkylalkyl, cycloalkenyl, cycloalkenylalkyl, aryl, aryloxy, aralkyl, or aralkoxy, any of which may be substituted with $W^1$, $W^2$ and $W^3$;
- (c) hydroxyl;
- (d) cyano;
- (e) nitro;
- (f) —C(O)H or —C(O)$R^{27}$;
- (g) —$CO_2$H or —$CO_2R_{27}$;
- (h) —SH, —S(O)$_n$R$^{27}$, —S(O)$_m$—C)H, —S(O)$_m$OR$^{27}$, —O—S(O)$_m$—R$^{27}$, —O—S(O)$_m$OH, or —O—S(O)$_m$—OR$^{27}$;
- (i) —$W^4$—NR$^{28}$R$^{29}$; or
- (j) —$W^4N(R^{32})$—$W^5$—NR$^{30}$R$^{31}$;

$R^{27}$ is alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{28}$ is
- (a) hydrogen;
- (b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;
- (c) cyano;
- (d) hydroxyl;
- (e) —C(O)H or —C(O)$R^{27}$;
- (f) —$CO_2R^{27}$;
- (g) —SH, —S(O)$_n$R$^{27}$, —S(O)$_m$—OH, —S(O)$_m$—OR$^{27}$, —O—S(O)$_m$—R$^{27}$, —O—S(O)$_m$OH, or —O—S(O)$_m$—OR$^{27}$, except when W4 is —S(O)$_n$—;

$R^{29}$ is
- (a) hydrogen;
- (b) —C(O)H or —C(O)$R^{27}$, except when $W^4$ is —C(O)— and $R^{28}$ is —C(O)H, —C(O)$R^{27}$, OF —$CO_2R_{27}$;
- (c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$; or $R^{28}$ and $R^{29}$ together are alkylene or alkenylene (either of which may be substituted with $W^1$, $W^2$ and $W^3$), completing a 3- to 8-membered saturated, unsaturated or aromatic ring together with the nitrogen atom to which they are attached;

$R^{30}$ is
- (a) hydrogen;
- (b) hydroxyl;
- (c) —C(O)H or —C(O)$R^{27}$;
- (d) —$CO_2R^{27}$;
- (e) —SH, —S(O)$_n$R$^{27}$, —S(O)$_m$—OH, —S(O)$_m$—OR$^{27}$, —O—S(O)$_m$—R$^{27}$, —O—S(O)$_m$OH, or —O—S(O)$_m$—OR$^{27}$;
- (f) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{32}$ is
- (a) hydrogen;
- (b) —C(O)H or —C(O)$R^{27}$, except when $W^5$ is —C(O)— and $R^{30}$ is —C(O)H, —C(O)$R^{27}$, or —$CO_2R^{27}$; or
- (c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{32}$ is
- (a) hydrogen;
- (b) hydroxyl
- (c) —C(O)H, —C(O)$R^{27}$ or $CO^2R^{27}$; or
- (d) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

or any two of $R^{30}$, $R^{31}$ and $R^{32}$ together are alkylene or alkenylene (either of which may be substituted with $W^1$, $W^2$ and $W^3$), completing a 3- to 8-membered saturated, unsaturated or aromatic ring together with the atoms to which they are attached;

$W^1$, $W^2$ and $W^3$ are each independently
- (a) hydrogen;
- (b) halo;
- (c) hydroxy;
- (d) alkyl;
- (e) alkenyl;
- (f) aralkyl;
- (g) alkoxy;
- (h) aryloxy;
- (i) aralkoxy;
- (j) —SH, —S(O)$_n$W$^6$, —S(O)$_m$—OH, —S(O)$_m$—OW$^6$, —O—S(O)$_m$—W$^6$, —O—S(O)$_m$OH, or —O—S(O)$_m$—OW$^6$;

(k) oxo;
(l) nitro;
(m) cyano;
(n) —C(O)H or —C(O)W$^6$;
(o) —CO$_2$H or —CO W$^6$;
(p) —W$_4$—NW$^7$W$^8$;
(q) W$^4$—N(W$^{11}$)—W$^5$—W$^6$; or
(r) —W$^4$—N(W$^{11}$)—W$^5$—NW$^7$W$^8$;

W$^4$ and W$^5$ are each independently
(a) a single bond;
(b) —W$^9$—S(O)$_n$—W$^{10}$—;
(c) —W$^9$C(O)—W$^{10}$—;
(d) —W$^9$—C(S)—W$^{10}$—;
(e) —W$^9$—O—W$^{10}$—;
(f) —W$^9$—S—W$^{10}$—; or
(g) —W$^9$—O—C(O)—W$^{10}$;

W$^6$, W$^7$ and W$^8$ are each independently hydrogen, alkyl, alkenyl, alkynyl, cycloalkyl, cycloalkylalkyl, cycloalkenyl, cycloalkenylalkyl, aryl, or aralkyl, or W$^7$ and W$^8$ together are alkylene or alkenylene, completing a 3- to 8-membered saturated, unsaturated or aromatic ring together with the nitrogen atom to which they are attached;

W$^9$ and W$^{10}$ are each independently a single bond, alkylene, alkenylene, or alkynylene;

W$^{11}$ is
(a) hydrogen;
(b) hydroxyl;
(c) —C(O)H, —C(O)W$^6$ or —CO$^2$W$^6$;
(d) alkyl, alkenyl, alkynyl, alkoxy, cycloalkyl, cycloalkylalkyl, cycloalkenyl, cycloalkenylalkyl, aryl, or aralkyl; or any two of W$^7$ and W$^8$ and W$^{11}$ together are alkylene or alkenylene, completing a 3- to 8-membered saturated, unsaturated, or aromatic ring together with the atoms to which they are attached;

m is 1 or 2; and
n is 0, 1, or 2.

Preferred compounds include those in which one of R$^3$, R$^5$ or R$^7$ is phenyl or phenoxy or compounds in which one of R$^3$, R$^5$ or R$^7$ is hydrogen, one of the other two of R$^3$, R$^5$ and R$^7$ is at the 2 position and is not hydrogen, and the other of R$^3$, R$^5$ and R$^7$ is at the 5 position. Thus, preferred compounds are 2-substituted benzenesulfonamides, and 2,5-substituted benzenesulfonamides. In addition, in preferred compounds R$^1$ is preferably halide. Preferred substituents are lower alkyl, particular methyl, ethyl, and propyl, halide, amino, dimethylamino, and methoxy.

(1) Ar$^2$ is phenyl

In particular Ar$^2$ has the formula (VI):

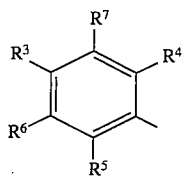

in which:
R$^1$ is halide or higher alkyl (greater than 8 carbons); R$^2$ selected from H, NH$_2$, NO$_2$, halide, pseudohalide, alkyl, alkenyl, alkynyl, aryl, arylalkyl, heterolaryl, alkoxy, alkylamino, alkylthio, haloalkoxy, haloalkyl, alkylsufinyl, alkylsulfonyl, aryloxy, arylamino, arylthio, arylsufinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons; and R$^3$, R$^4$, R$^5$, R$^6$, and R$^7$ are either (i) or (ii) as follows:
(i) R$^3$, R$^4$, R$^5$, R$^6$, and R$^7$ are selected independently from among H, NHOH, NH$_2$, No$_2$, pseudohalide, including N$_3$, halide, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons, are unsubstituted or substituted with groups, such as any set forth for R$^8$, R$^9$, R$^{10}$ and R$^{11}$, above, and the aryl portions contain from 3 up to about 10 carbons, preferably 3 to 6 carbons, and, also are unsubstituted or substituted with groups, such as any set forth for R$^8$, R$^9$, R$^{10}$ and R$^{11}$,; R$^4$ and R$^6$ are as defined in (i); or (ii) R$^3$, R$^5$, and R$^7$ are H; and R$^4$ and R$^6$ are each independently selected from alkyl, alkoxy, halide, aminoalkyl, dialkylamino, dialkylaminoalkyl, which are unsubstituted or substituted with alkyl groups, and in which the alkyl and alkoxy groups contain from 1 to 1 0, preferably 1 to 6 carbons, and are straight or branched chains.

Compounds in which at least one of R$^3$–R$^7$ is phenyl are discussed below with the biphenyl compounds.

In certain preferred embodiments: R$^1$ is halide or a higher alkyl selected from C$_9$H$_{19}$ to C$_{13}$H$_{27}$; R$^2$ is selected independently from alkyl, lower alkenyl, lower alkynl, lower haloalkyl and H; and R$^3$, R$^4$, R$^5$, R$^6$, and R$^7$ are either (i) or (ii) as follows:

(i) R$^4$, R$^5$, R$^6$ and R$^7$ are each independently selected from H, lower alkyl, NH$_2$, NO$_2$, halide, pseudohalide; R$^3$ is selected from H, NHOH, NH$_2$, NO$_2$, N$_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from 1 up to 5 or 6 carbons and the aryl portions contain from 4 to 14 carbons; or (ii) R$^3$, R$^5$, and R$^7$ are H; and R$^4$ and R$^6$ are each independently selected from alkyl, alkoxy, halide, aminoalkyl, and dialkylaminoalkyl, which are unsubstituted or substituted with alkyl groups, and in which the alkyl and alkoxy groups contain 1 to 6 carbons, and are straight or branched chains.

In more preferred embodiments, R$^1$ is Cl or Br, or if greater ET$_8$ activity is preferred a higher alkyl (C$_9$H$_{19}$ to C$_{13}$H$_{27}$;d R$^2$ is selected from H, CH$_3$, C$_2$H$_5$, CF$_3$, C$_2$F$_5$, n-C$_3$H$_7$, cyolo-C$_3$H$_7$, nC$_{13}$H$_{27}$ and nC$_9$H$_{19}$; and R$^3$, R$^4$, R$^5$, R$^6$, and R$^7$ are either (i) or (ii) as follows:

(i) R$^4$, R$^5$, R$^6$ and R$^7$ are each independently selected from H, halide, NH$_2$, CF$_3$, Ph and CH$_3$; R$^3$ is selected from H, NHOH, NH$_2$, C$_2$H$_5$NH$_2$, (CH$_3$)$_2$NH, Ph-CH$_2$NH, NO$_2$, F, Cl, Br, I, CN, CH$_3$, (CH$_3$)$_3$C, C$_5$H$_{11}$, CH$_3$O, n-C$_4$H$_9$O, CH$_2$=CH, Ph-CH=CH, CH≡C, Ph-CH≡C, Ph, 3-(ethyoxycarbonylmethyl)ureido, and 3-cyclohexylureido; or (ii) $R^3$, $R^5$, and $R^7$ are H; and $R^4$ and $R^6$ are each independently selected from alkyl and aminoalkyl in whcih the alkyl groups have from 1 to 6 carbons that may from straight or branched chains.

In yet more preferred embodiments, $R^1$ is Br, Cl or $C_9H_{19}$ to $C_{13}H_{27}$; $R^2$ is H, $CH_3$, $C_2H_5$, or $CF_3$; and $R^3$, $R^4$, $R^5$, $R^6$, and $R^7$ are either (i) or (ii) as follows (i) $R^3$ is H, $NH_2$, $CH_3$ $CF_3$, halide or $C_2H_5NH$; $R^4$, $R^5$ and $R^6$ are independently selected from H, $CH_3$, $C_2H_5$, $(CH_3)_2CH$, $CF_3$, halide, particularly Br and Cl, $NH_2$; and $R^7$ is H, $CH_3$, $CH_2$ $CH_5$, $(CH_3)CH$, F or $CF_3$; or (ii) $R^3$, $R^5$, and $R^7$ are H; and $R^4$ and $R^6$ are each independently selected from alkyl groups in which the alkyl groups have from 1 to 3 carbons and may form straight or branched chains.

Of the above compounds those with ortho and/or meta substituents or those that are substituted at positions 2 and 5 on the benzene ring are generally more preferred, except when the resulting compound is a biphenyl and $ET_B$ affinity is desired, then the corresponding para-substituted compounds are preferred. Compounds with ortho substituents are more generally more preferred than the corresponding meta-substituted compounds. This observation is particularly important when activity with respect to $ET_A$ receptors is considered. In addition, in preferred compounds $R^1$ is preferably halide. Preferred substituents are lower alkyl, particular methyl, ethyl, and propyl, halide, amino, dimethylamino, and methoxy. Other preferred substituents may be deduced from the following Table.

Benzene sulfonamides were synthesized and tested using the exemplified assays (see, EXAMPLES) and selected results are set forth in Table 1 (the N-( 3,4-dimethyl-5-isoxazolyl)benzenesulfonamides are generlly included for comparison with the corresponding N-(4-halo-3-methyl-5-isoxazolyl)benzenesulfonamide.

TABLE 1

| COMPOUND | $ET_A$ (μM)* | $ET_B$ (μM)* |
|---|---|---|
| N-(4-bromo-5-methyl-3-isoxazolyl)benzenesulfonamide | 0.097 ± 0.04 | 31 ± 5.3 |
| 2-chloro-4-fluoro-N-(5-methyl-3-isoxazoly)benzenesulfonamide | — | — |
| N-(4-bromo-5-tert-butyl-3-isoxazolyl)benzenesulfonamide | — | — |
| N-(4-chloro-5-methyl-3-isoxazolyl)benzenesulfonamide | — | — |
| N-(4-iodo-5-methyl-3-isoxazolyl)benzenesulfonamide | — | — |
| 4-nitro-N-(4-bromo-5-methyl-3-isoxazolyl)benzenesulfonamide | — | — |
| 5-nitro-N-(4-bromo-5-methyl-3-isoxazolyl)benzenesulfonamide | — | — |
| N-(3-methyl-4-bromo-5-isoxazolyl)benzenesulfonamide | 0.055 ± 0.005 | 19.5 ± 4 |
| N-(4-bromo-3-phenyl-5-isoxazolyl)benzenesulfonamide | — | — |
| N-(4-chloro-3-methyl-5-isoxazolyl)benzenesulfonamide | ~0.11 | 25.6 |
| N-(4-bromo-3-tert-butyl-5-isoxazolyl)benzenesulfonamide | — | — |
| 4-iso-propyl-N-(4-bromo-3-methyl-5-isoxazolyl)benzenesulfonamide | 17.3 | 0.78 |
| 4-bromo-N-(3,4-dimethyl-5-isoxazolyl)benzenesulfonamide | 8.9 | 14.4 |
| 4-bromo-N-(4-bromo-3-methyl-5-isoxazolyl)benzenesulfonamide | 3.0 | 3.8 |
| 4-fluoro-N-(3,4-dimethyl-5-isoxazolyl)benzenesulfonamide | 7 ± 3 | 57 ± 13 |
| 4-fluoro-N-(4-bromo-3-methyl-5-isoxazolyl)benzenesulfonamide | 1.2 | 15.3 |
| 3-nitro-N-(3,4-dimethyl-5-isoxazolyl)benzenesulfonamide | 13.7 | — |
| 3-nitro-N-(4-bromo-3-methyl-5-isoxazolyl)benzenesulfonamide | 2.8 | 40 |
| 4-iodo-N-(4-bromo-3-methyl-5-isoxazolyl)benzenesulfonamide | 6.3 ± 2.5 | 1.05 ± 0.08 |
| 4-chloro-N-(4-bromo-3-methyl-5-isoxazolyl)benzenesulfonamide | 1.96 ± 1 | 7.02 ± 2 |
| N-(4-bromo-3-ethyl-5-isoxazolyl)benzenesulfonamide | 0.47 ± 0.3 | 67.1 ± 6 |
| 4-methyl-N-(4-bromo-3-methyl-5-isoxazolyl)-4-benzenesulfonamide | 1.44 ± 0.8 | 4.0 ± 0.9 |
| 2,5-dimethyl-N-(4-bromo-3-methyl-5-isoxazolyl)benzenesulfonamide | 0.044 ± 0.03 | 15.5 ± 3 |
| 2-fluoro-N-(4-bromo-3-methyl-5-isoxazolyl)benzenesulfonamide | 0.20 | 40.8 |
| 3-fluoro-N-(4-bromo-3-methyl-5-isoxazolyl)benzenesulfonamide | 0.21 | 38.3 |
| 2,5-dimethyl-N-(3,4-di-methyl-5-isoxazolyl)benzenesulfonamide | 9.4 | 66.3 |
| 2,5-dimethyl-N-(4-chloro-3-methyl-5-isoxazolyl)benzenesulfonamide | 0.19 | 30.7 |

TABLE 1-continued

| COMPOUND | $ET_A$ (μM)* | $ET_B$ (μM)* |
|---|---|---|
| 4-acetamido-N-(3,4-dimethyl-5-isoxazolyl)benzenesulfonamide | 18.1 | — |
| 4-acetamido-N-(4-bromo-3-methyl-5-isoxazolyl)benzenesulfonamide | 6.4 ± 3.5 | ~26 |
| 4-nitro-N-(3,4-dimethyl-5-isoxazolyl)benzenesulfonamide | 100 | 10 |
| 4-nitro-N-(4-bromo-5-methyl-3-isoxazolyl)benzenesulfonamide | 53 ± 1.0 | 9.4 ± 2 |
| 2,4,6-trimethyl-N-(3,4-dimethyl-5-isoxazolyl)benzenesulfonamide | 52 ± 4 | — |
| 2,4,6-trimethyl-N-(4-bromo-3-methyl-5-isoxazolyl)benzenesulfonamide | 5.9 ± 0.9 | 45.5 ± 4.4 |
| 4-iodo-N-(3,4-dimethyl-5-isoxazolyl)benzenesulfonamide | 36 ± 3 | 6 |
| 4-iodo-N-(4-bromo-3-methyl-5-isoxazolyl)benzenesulfonamide | 6.3 ± 2.5 | 1.05 ± 0.08 |
| 4-chloro-N-(3,4-dimethyl-5-isoxazolyl)benzenesulfonamide | 10.2 ± 1.5 | 29.2 ± 0.07 |
| 4-chloro-N-(4-bromo-3-methyl-5-isoxazolyl)benzenesulfonamide | 1.96 ± 1 | 7.02 ± 2 |
| 2-chloro-N-(4-bromo-3-methyl-5-isoxazolyl)benzenesulfonamide | .071 ± .06 | 37 ± 2 |
| 3,4-dichloro-N-(3,4-dimethyl-5-isoxazolyl)benzenesulfonamide | 3.8 ± 1.5 | 25 ± 6 |
| 3,4-dichloro-N-(4-bromo-3-methyl-5-isoxazolyl)benzenesulfonamide | **0.90 ± 0.2<br>0.48 ± 0.07 | 6.9 ± 1.8<br>6.5 ± 0.9 |
| 2,4-dichloro-N-(3,4-dimethyl-5-isoxazolyl)benzenesulfonamide | 14 ± 7 | 104 ± 12 |
| 2,4-dichloro-N-(4-bromo-3-methyl-5-isoxazolyl)benzenesulfonamide | 2.6 ± 0.3 | 24 ± 7 |
| 2-fluoro-N-(4-bromo-3-methyl-5-isoxazolyl)benzenesulfonamide | 0.16 ± 0.04 | 35 ± 6 |
| 3-fluoro-N-(4-bromo-3-methyl-5-isoxazolyl)benzenesulfonamide | 0.14 ± 0.06 | 24.8 |
| 2,5-dimethyl-N-(4-chloro-3-methyl-5-isoxazolyl)benzenesulfonamide | 12.7 ± 6.7 | 12 |
| 4-nitro-N-(4-bromo-3-methyl-5-isoxazolyl)benzenesulfonamide | 19 ± 5 | 6.8 ± 3 |
| 4-butoxy-N-(3,4-dimethyl-5-isoxazolyl)benzenesulfonamide | 9.2 | 7.4 |
| 4-butoxy-N-(4-bromo-3-methyl-5-isoxazolyl)benzenesulfonamide | 3.0 ± 0.7 | 2.0 ± 0.8 |
| 3-chloro-2-methyl-N-(4-bromo-3-methyl-5-isoxazolyl)benzenesulfonamide | 0.165 ± 0.13 | 22 ± 15 |
| 2-methyl-N-(4-bromo-3-methyl-5-isoxazolyl)benzenesulfonamide | 0.12 ± 0.01 | 13 ± 1 |
| 3-chloro-2,5-dimethyl-N-(4-bromo-3-methyl-5-isoxazolyl)benzenesulfonamide | 0.31 ± 0.03 | 11.2 ± 0.3 |
| 2,6-difluoro-N-(4-bromo-3-methyl-5-isoxazolyl)benzenesulfonamide | 0.16 ± 0.1 | 63 ± 10 |
| 2,5-difluoro-N-(4-bromo-3-methyl-5-isoxazolyl)benzenesulfonamide | 2.4 ± 0.2 | 26.8 ± 3.7 |
| 2,3,4-trichloro-N-(4-bromo-3-methyl-5-isoxazolyl)benzenesulfonamide | 2.1 ± 0.01 | 10.2 ± 2.0 |
| 2,3-dichloro-N-(4-bromo-3-methyl-5-isoxazolyl)benzenesulfonamide | 0.19 ± 0.04 | 20.4 ± 2.3 |
| 2,5-dichloro-N-(4-bromo-3-methyl-5-isoxazolyl)benzenesulfonamide | 0.113 ± 0.02 | 25 ± 3 |
| 5-bromo-2-methoxy-N-(4-bromo-3-methyl-5-isoxazolyl)benzenesulfonamide | 0.072 ± 0.03 | 5.3 ± 0.4 |
| 2-bromo-5-ethyl-N-(4-chloro-3-methyl-5-isoxazolyl)benzenesulfonamide | 0.057 | 3.5 ± 0.4 |
| 2-bromo-5-methyl-N-(4-bromo-3-methyl-5-isoxazolyl)benzenesulfonamide | 0.046 ± 0.002 | 11.5 ± 4 |
| 2-bromo-5-ethyl-N-(4-bromo-3-methyl-5-isoxazolyl)benzenesulfonamide | 0.029 ± 0.010 | 5.2 ± 1.1 |
| 5-bromo-2-ethyl-N-(4-bromo-3-methyl-5-isoxazolyl)benzenesulfonamide | 0.0028 ± 0.002 | 5.2 ± 1.1 |
| 2,5-diethyl-N-(4-bromo-3-methyl-5-isoxazolyl)benzenesulfonamide | 0.0062 ± 0.003 | 5.2 ± 0.8 |
| 2,5-diethyl-N-(3,4-dimethyl-5-isoxazolyl)benzenesulfonamide | 0.027 ± 0.01 | 17 ± 7 |
| 2-bromo-N-(4-bromo-3-methyl-5-isoxazolyl)benzenesulfonamide | 0.040 ± 0.02 | 39 ± 4 |
| 2-cyano-N-(4-bromo-3-methyl-5-isoxazolyl)benzenesulfonamide | 0.18 ± 0.02 | ~80 |
| 2,4,5-trichloro-N-(4-bromo-3-methyl-5- | 1.2 ± 0.1 | 23 ± 3 |

TABLE 1-continued

| COMPOUND | ET$_A$ (μM)* | ET$_B$ (μM)* |
| --- | --- | --- |
| isoxazolyl)benzenesulfonamide | | |
| 3,4-dimethoxy-N-(4-bromo-3-methyl-5-isoxazolyl)benzenesulfonamide | 0.49 ± 0.18 | 24 ± 5 |
| 4-trifluoromethyl-N-(3,4-dimethyl-5-isoxazolyl)benzenesulfonamide | 129 | 12.1 |
| 4-trifluormethyl-N-(4-bromo-3-methyl-5-isoxazolyl)benzenesulfonamide | 22 ± 3.0 | 3.0 ± 0.2 |
| 3-trifluoromethyl-N-(4-bromo-3-methyl-5-isoxazolyl)benzenesulfonamide | 1.5 ± 0.2 | 21 ± 0.4 |
| 2,5-dimethoxy-N-(4-bromo-3-methyl-5-isoxazolyl)benzenesulfonamide | 0.19 ± 0.03 | 14 ± 0.7 |
| 5-chloro-2-methoxy-N-(4-bromo-3-methyl-5-isoxazolyl)benzenesulfonamide | 0.94 ± 0.14 | 10.2 ± 1 |
| 3-chloro-2-methyl-N-(3,4-dimethyl-5-isoxazolyl)benzenesulfonamide | 10.2 ± 1.5 | 29.2 ± 0.7 |
| 3-chloro-N-(4-bromo-3-methyl-5-isoxazolyl)benzenesulfonamide | 0.23 ± 0.06 | 34.7 ± 1.4 |
| N-(4-bromo-3-trifluoromethyl-5-isoxazolyl)benzenesulfonamide | 0.33 ± 0.08 | 34.7 ± 1.4 |
| N-(4-isothiocyanato-3-methyl-5-isoxazolyl)benzenesulfonamide | 0.62 ± 0.3 | — |
| 3-carboxyl-N-(4-bromo-3-methyl-5-isoxazolyl)benzenesulfonamide | 0.18 ± 0.05 | 7.6 ± 2.7 |
| 3,5-dichloro-N-(4-bromo-3-methyl-5-isoxazolyl)benzenesulfonamide | 0.062 ± 0.02 | 14.2 ± 1.0 |
| 3-chloro-5-fluoro-N-(4-bromo-3-methyl-5-isoxazolyl)benzenesulfonamide | 0.54 ± 0.1 | 17.0 ± 0.7 |
| 3,5-di(trifluoromethyl)-N-(4-bromo-3-methyl-5-isoxazolyl)benzenesulfonamide | 0.57 ± 0.07 | 17.1 ± 0.6 |
| 2,5-difluoro-N-(4-chloro-3-methyl-5-isoxazolyl)benzenesulfonamide | 0.19 ± 0.05 | 58 ± 10 |
| 2-chloro-5-methyl-N-(4-chloro-3-methyl-5-isoxazolyl)benzenesulfonamide | 0.22 ± 0.04 | 49 ± 2 |
| 2,5-dichloro-N-(4-bromo-3-methyl-5-isoxazolyl)benzenesulfonamide | 0.58 ± 0.25 | 17.4 ± 0.8 |
| 2-chloro-4-fluoro-N-(4-bromo-3-methyl-5-isoxazolyl)benzenesulfonamide | ~2.0 | 31 ± 0.3 |
| 2,5-difluoro-N-(4-bromo-3-methyl-5-isoxazolyl)benzenesulfonamide | 0.16 ± 0.1 | 63 ± 10 |
| 2-chloro-5-methyl-N-(4-bromo-3-methyl-5-isoxazolyl)benzenesulfonamide | 1.26 ± 0.19 | 37 ± 1 |
| 2-methyl-5-amino-N-(4-bromo-3-methyl-5-isoxazolyl)benzenesulfonamide | 0.34 ± 0.01 | ~100 |
| 2-methyl-5-dimethylamino-N-(4-bromo-3-methyl-5-isoxazolyl)benzenesulfonamide | 0.21 ± 0.03 | 44 ± 8 |
| 3-acetamido-N-(4-bromo-3-methyl-5-isoxazolyl)benzenesulfonamide | 0.35 ± 0.05 | 4.0 ± 1 |
| 3-bromo-N-(4-bromo-3-methyl-5-isoxazolyl)benzenesulfonamide | 0.23 ± 0.06 | 9.4 ± 1.4 |
| 2-phenoxy-5-nitro-N-(4-bromo-3-methyl-5-isoxazolyl)benzenesulfonamide | 0.79 ± 0.14 | 19.5 ± 0.1 |
| 4-ethyl-N-(4-bromo-3-methyl-5-isoxazolyl)benzenesulfonamide | 0.34 ± 0.05 | 083 ± 0.05 |
| 2,5-dibromo-3,6-difluoro-N-(4-bromo-3-methyl-5-isoxazolyl)benzenesulfonamide | 0.035 | 13.3 ± 1 |
| 2-trifluoromethoxy-N-(4-bromo-3-methyl-5-isoxazolyl)benzenesulfonamide | 0.017 | 55 ± 7 |
| 2-methyl-5-fluoro-N-(4-bromo-3-methyl-5-isoxazolyl)benzenesulfonamide | 0.099 | 78 ± 8 |
| 2-butyl-5-bromo-N-(4-bromo-3-methyl-5-isoxazolyl)benzenesulfonamide | 0.038 | 3.6 ± 0.3 |
| 2-bromo-5-butyl-N-(4-bromo-3-methyl-5-isoxazolyl)benzenesulfonamide | 0.85 ± 0.11 | 5.4 ± 0.3 |
| 2-methyl-5-bromo-N-(4-bromo-3-methyl-5-isoxazolyl)benzenesulfonamide | 0.24 | 13 ± 2 |
| 2,5-dipropyl-N-(4-bromo-3-methyl-5-isoxazolyl)benzenesulfonamide | 0.19 ± 0.3 | 14.4 ± 1.8 |
| 2-dimethylamino-5-methyl-N-(4-bromo-3-methyl-5-isoxazolyl)benzenesulfonamide | 8.1 ± 0.2 | 0.93 ± 0.25 |
| 2-methylamino-5-methyl-N-(4-bromo-3-methyl-5-isoxazolyl)benzenesulfonamide | 0.0081 ± 0.0002 | 0.93 ± 0.25 |
| 2-methylamino-5-methyl-N-(4-chloro-3-methyl-5-isoxazolyl)benzenesulfonamide | 0.0032 ± 0.0001 | 5.6 ± 0.6 |
| 2-methyl-5-dimethylamino-N-(4-bromo-3-methyl-5-isoxazolyl)benzenesulfonamide | 0.25 ± 0.01 | 31 ± 4 |
| 2-ethyl-5-dimethylamino-N-(4-bromo-3-methyl-5-isoxazolyl)benzenesulfonamide | 0.16 | 23 |

TABLE 1-continued

| COMPOUND | $ET_A$ (μM)* | $ET_B$ (μM)* |
|---|---|---|
| 2-methyl-5-azido-N-(4-bromo-3-methyl-5-isoxazolyl)benzenesulfonamide | 0.28 ± 0.04 | 4.2 ± 0.1 |
| 2,4-diethyl-N-(4-chloro-3-methyl-5-isoxazolyl)benzenesulfonamide | 0.62 ± 0.13 | 11.5 ± 3.4 |
| 2,4-diethyl-N-(4-bromo-3-methyl-5-isoxazolyl)benzenesulfonamide | 0.56 ± 0.08 | 9.3 ± 3 |
| 2-butyl-5-bromo-N-(4-chloro-3-methyl-5-isoxazolyl)benzenesulfonamide | 0.051 | 4.4 ± 0.1 |
| 2-bromo-N-(4-chloro-3-methyl-5-isoxazolyl)benzenesulfonamide | 0.086 | — |
| 2-bromo-5-butyl-N-(4-chloro-3-methyl-5-isoxazolyl)benzenesulfonamide | 1.1 | 4.6 ± 0.6 |
| 2-propyl-5-bromo-N-(3,4-dimethyl-5-isoxazolyl | ~.020 | 26 ± 4 |
| 2-propyl-5-bromo-N-(4-bromo-3-methyl-5-isoxazolyl)benzenesulfonamide | ~0.006 | 6.55 ± 0.2 |
| 2-propyl-5-bromo-N-(4-chloro-3-methyl-5-isoxazolyl)benzenesulfonamide | — | 14 ± 4 |
| 4-(N'-Cyclohexylureido-N-(3,4-dimethyl-5-isoxazolyl)benzenesulfonamide | 3.8 ± 0.3 | 100 ± 5 |
| N-(4-nonyl-3-trifluoromethyl-5-isoxazolyl)benzenesulfonamide | 8.7 ± 0.5 | 9.2 ± 0.7 |
| N-(4-tridecyl-3-trifluoromethyl-5-isoxazolyl)benzenesulfonamide | 13.2 ± 2 | 1.8 ± 0.5 |
| N-(4-ethyl-3-trifluoromethyl-5-isoxazolyl)benzenesulfonamide | 0.12 ± 0.02 | 27 ± 3 |
| N-(4-hexyl-3-trifluoromethyl-5-isoxazolyl)benzenesulfonamide | 11 ± 2.0 | 63 ± 9 |

*results generally from 1, 2 or 3 experiments with the same preparation
**Two preparations

(2) $Ar^2$ is biphenyl

In certain of the embodiments herein, $Ar^1$ is N-(5-isoxazolyl) or N-(3-isoxazolyl) with $R^1$ and $R^2$ selected as described above, and $Ar^2$ is a substituted benzene group in which one of $R^3$, $R^4$, $R^5$, $R^6$ and $R^7$ is selected independently from phenyl or substituted phenyl. The remaining of $R^3$, $R^4$, $R^5$, $R^6$ and $R^7$ are selected as described in (1) above for embodiments in which $Ar^2$ is phenyl. $R^1$ and $R^2$ are also selected as described in (1) above, except in instances when one Of $R^3$, $R^4$, $R^5$, $R^6$ and $R^7$ is at the 3 or 4 position so that the resulting compounds are 3- or 4-biphenyl compounds. In these instances, $R^2$ is selected as described above, but $R^1$ can be halide and higher alkly, and in addition, can be any of the substituents set forth for $R^2$, For the 3-or 4-biphenyl compounds $R^1$ is preferably halide, lower alkyl, particularly $CH_3$, or $C_9H_{19}$—$C_{13}H_{27}$, In certain embodiments, $Ar^2$ is unsubstituted or substituted biphenyl group of formula (VII):

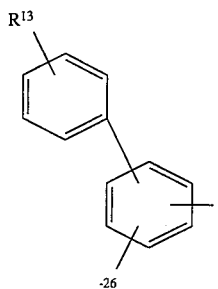

in which each ring may have one or more substituents each selected independently from $R^{26}$ and $R^{13}$ where:

(i) $R^{26}$ and $R^{13}$ are independently selected from H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons; or (ii) $R^{26}$ and $R^{13}$ together (see, Formula IVb) are —$CH_2$—, —CH=$CH_2$—O, S, $NR^{11}$ in which $R^{11}$ is as defined above, and is preferably, H or alkyl, particularly lower alkyl. It is understood that in either (i) or (ii) each ring of $Ar^2$ may be unsubstituted or substituted with more than one substituent, each of which is selected independently from the selections set forth in (i) for $R^{26}$ and $R^{13}$, These compounds, thus, include biphenylsulfonamides, fused tricyclicsubstituted sulfonamides dibenzothiophenesulfonamides, dibenzofuransulfonamides, dibenzopyrrolefonamides (carbazolesulfonamides) and phenanthrenesulfonamides. The dibenzothiophenesulfonamides, dibenzofuransulfonamides, dibenzopyrrolefonamides and phenanthrenesulfonamides are discussed separately with the compounds in which $Ar^2$ is a heterocycle with one heteroatom and two or more fused rings.

Among preferred embodiments herein, $Ar^2$ is has formula (VIII):

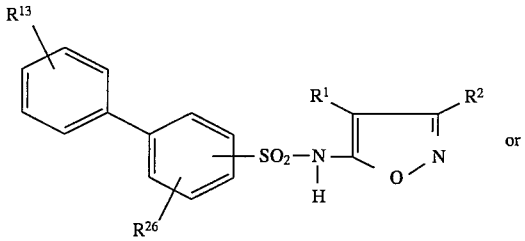

or

-continued

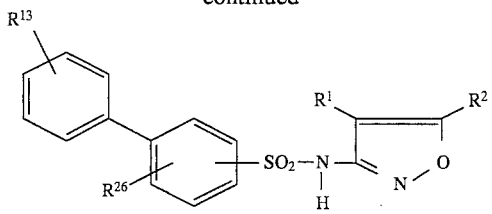

in which $R^{26}$ and $R^{13}$ are selected from H, lower alkyl, haloalkyl and halide. Again, it is understood that $Ar^2$ may be substituted with more than one substituent, each of which is selected independently from the selections set forth for $R^{26}$ and $R^{13}$, In preferred embodiments, in which the sulfonamides are biphenylsulfonamides in which $R^1$ is halide; $R^2$ is selected from alkyl, lower alkenyl, lower alkynl, lower haloalkyl and H; and $R^{26}$ and $R^{13}$ are selected from H, lower alkyl, haloalkyl and halide. In preferred of these embodiments, $R^1$ is Cl or Br, and for the 3-biphenylsulfonamides and 4-biphenylsulfonamides, $R^1$ is also $CH_3$; $R^2$ is selected from H, $CH_3$, $C_2H_5$, $CF_3$, $C_2F_5$, n-$C_3H_7$ and cyclo-$C_3H_7$; and $R^{26}$ and $R^{13}$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2$=CH.

In yet more preferred embodiments, $R^2$ is H, $CH_3$, $C_2H_5$, or $CF_3$; $R^{26}$ and $R^{13}$ are independently selected from H, $CH_3$, $C_2H_5$, $CF_3$, and halide; and X is O.

In another preferred embodiment, the biphenylsulfonamides are 3- or 4-biphenylsulfonamides, in such instances $R^1$ is preferably, halide or methyl. Such compounds have a higher $ET_B$ affinity than the 2-biphenylsulfonamides. It is also preferred that the substituent at the 2-position is hydrogen. $R^1$ is selected from halide, $CH_3$, $C_2H_5$, $CF_3$, $C_2F_5$, n-$C_3H_7$ and cyclo-$C_3H_7$, preferably halide or $CH_3$, and $R^2$ is selected from H, $CH_3$, $C_2H_5$, $CF_3$, $C_2F_5$, n-$C_3H_7$ and cyclo-$C_3H_7$; and $R^{26}$ and $R^{13}$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2$=CH. In more preferred of these embodiments, $R^1$ is halide or $CH_3$, and $R^2$ are selected from H, $CH_3$, $C_2H_5$, or $CF_3$; $R^{26}$ and $R^{13}$ are independently selected from H, $CH_3$, $C_2H_5$, $CF_3$, and halide.

Exemplary biphenyl sulfonamides are the following and those set forth in Table 2:

N-(4-bromo-3-methyl-5-isoxazolyl)-4-biphenylsulfonamide;

N-(4-chloro-3-methyl-5-isoxazolyl)-4-biphenylsulfonamide;

N-(4-bromo-5-methyl-3-isoxazolyl)-4-biphenylsulfonamide;

N-(4-chloro-5-methyl-3-isoxazolyl)-4-biphenylsulfonamide.

The biphenyl compounds provided herein are generally $ET_B$ active or $ET_B$ selective (see, e.g., Table 2); i.e. the compounds provided herein inhibit binding of endothelin to $ET_B$ receptors at concentrations about 10- to about 30-fold less than they inhibit binding of endothelin to $ET_A$ receptors. In particular the 4-biphenylsulfonamides are $ET_B$ selective.

The biphenyl compounds were tested using the exemplified assays (see, EXAMPLES) and the results are as set forth in the following table (Table 2):

TABLE 2

| COMPOUND | $ET_A$ (μM)* | $ET_B$ (μM)* |
|---|---|---|
| N-(4-bromo-3-methyl-5-isoxazolyl)-4-biphenylsulfonamide | 3.3 | ~0.17 |
| N-(4-bromo-5-methyl-3-isoxazolyl)-4-biphenylsulfonamide | 6.4 ± 2 | 0.29 ± 0.02 |
| N-(4-chloro-3-methyl-5-isoxazolyl)-4-biphenylsulfonamide | 4.93 ± 3 | 0.29 ± 0.1 |
| N-(3,4-dimethyl-5-isoxazolyl)-4-biphenylsufonamide | 9.9 ± 1.4 | 0.77 ± 0.32 |
| N-(4-chloro-5-methyl-3-isoxazolyl)-4-biphenylsulfonamide | 3.7 | 0.23 ± 0.01 |
| N-(4-Methyl-3-trifluoromethyl-5-isoxazolyl)-4-biphenylsulfonamide | 19.0 | 1.7 |
| N-(4-Tridecyl-3-trifluoromethyl-5-isoxazolyl)-4-biphenylsulfonamide | 34.0 ± 9 | 0.99 ± 0.2 |
| N-(3,4-dimethyl-5-isoxazolyl)-2-biphenylsulfonamide | 0.0083 ± 0.0014 | — |
| N-(4-bromo-3-methyl-5-isoxazolyl)-2-biphenylsulfonamide | 0.00127** | 8.54** |
| N-(4-chloro-3-methyl-5-isoxazolyl)-2-biphenlsulfonami | 0.00123** | ~14** |
| N-(3,4-dimethyl-5-isoxazolyl)-3-biphenylsulfonamide | >0.03** | 3.48** |
| N-(4-bromo-3-methyl-5-isoxazolyl)-3-biphenylsulfonamide | ~0.03** | 0.76** |
| N-(4-chloro-3-methyl-5-isoxazolyl)-3-biphenylsulfonamide | >0.03** | 0.793** |

*results generally from 1, 2 or 3 experiments with the same preparation
**preliminary results b. Compounds in which $Ar^2$ is phenyl and biphenyl and n>0

$Ar^2$ has formula (IX):

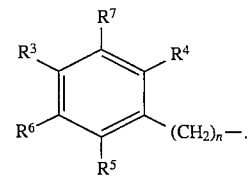

These compounds include those in the formula set forth in 1 a above in which n is 1 to 10, preferably 1 to 6, more preferably 1 to 3; $R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heterolaryl, alkoxy, alkylamino, alkylthio, haloalkoxy, haloalkyl, alkylsufinyl, alkylsulfonyl, aryloxy, arylamino, arylthio, arylsufinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide or pseudohalide; or, (ii) $R^1$ and $R^2$ together form $—(CH_2)_n—$, where n is 3 to 6; or, (iii) $R^1$ and $R^2$ together form 1,3-butadienyl; and $R^3$, $R^4$, $R^5$, $R^6$, and $R^7$ are selected from (i), (ii), (iii) or (iv):

(i) $R^3$, $R^4$, $R^5$, $R^6$, and $R^7$ are each selected independently from among H, NHOH, $NH_2$, $NO_2$, $N_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl,-formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons and the aryl portions contain from 3 up to about 10 carbons, preferably 6 carbons; or, alternatively, (ii) $R^4$ and $R^7$ together are substituted or unsubstituted 1, 3-butadienyl, 4-dimethylamino-1,3 butadiene, 1-chloro-1,3-butadiene, 1-aza-1,3-butadienyl or 2-aza- 1,3-butadienyl groups; and $R^3$, $R^5$ and $R^6$ are as defined in (i) above; or alternatively, (iii) $R^7$ and $R^3$ together are substituted or unsubstituted 1, 3-butadienyl, 4-dimethylamino-1,3 butadiene, 1-chloro-1,3-butadiene, 1-aza-1,3-butadienyl or 2-aza-1,3-butadienyl groups; and $R^4$, $R^5$ and $R^6$ are as defined in (i) above; or (iv) $R^3$, $R^5$, and $R^7$ are H are as defined in (i); and $R^4$ and $R^6$ are each independently selected from alkyl, alkoxy, halide aminoalkyl, dialkylaminoalkyl, which are unsubstituted or substituted with alkyl groups, in which the alkyl and alkoxy groups contain from 1 to 10, preferably 1 to 6 carbons, and are straight or branched chains.

In more preferred embodiments, $R^2$ is H, $CH_3$, $C_2H_5$, $CF_3$, $C_2F_5$, n-$C_3H_7$, cyclo-$C_3H_7$ and $C_4H_8$; $R^1$ is Br, Cl, $CH_3$, or, if greater $ET_B$ affinity is desired, is higher alkyl; n is 1–3; and $R^3$, $R^4$, $R^5$, $R^6$, $R^7$, are selected from either (i), (ii), (iii) or (iv) as follows:

(i) $R^5$ and $R^6$ are H; $R^4$ and $R^7$ are each independently selected from H, halide, $NH_2$, $CF_3$, Ph, $CH_3$; and $R^3$ is selected from H, NHOH, $NH_2$, $EtNH_2$, $(CH_3)_2NH$, $Ph-CH_2NH$, $NO_2$, F, Cl, Br, I, CN, $CH_3$, $(CH_3)_3C$, $C_5H_{11}$, $CH_3O$, n-$C_4H_9O$, $CH_2=CH$, Ph-$CH=CH$, $CH\equiv C$, Ph-$CH\equiv C$, Ph, 3-(ethyoxycarbonylmethyl)ureido, and 3-cyclohexylureido; or (ii) $R^4$ and $R^7$ together form 1, 3-butadienyl, 4-chloro-1,3-butadienyl, 4-dimethylamino-1,3-butadienyl or 1-aza-1,3-butadienyl; and $R^3$, $R^5$ and $R^6$ are defined as in (i) of this embodiment; or (iii) $R^7$ and $R^3$ together form 1,3-butadienyl, 3-chloro-1,3-butadienyl 4-dimethylamino-1,3-butadienyl or 1-aza-1,3-butadienyl; and $R^4$, $R^5$ and $R^6$ are as defined in (i) of this embodiment; or (iv) $R^3$, $R^5$, and $R^7$ are H as defined in (i); and $R^4$ and $R^6$ are each independently selected from alkyl, alkoxy, halide, amino alkyl, alkylaminoalkyl or dialkylaminoalkyl, which are unsubstituted or substituted with alkyl groups, in which the alkyl and alkoxy groups contain from 1 to 10, preferably 1 to 6 carbons, and are straight or branched chains.

More preferred among the above compounds are those in which n is 1 to 3; $R^1$ is Br, Cl, I or $CH_3$ or, if greater $ET_B$ affinity is desired, is $C_9H_{19}$ —$C_{13}H_{27}$; $R^2$ is H, $CH_3$, $C_2H_5$, $CF_3$, $C_2F_5$, n-$C_3H_7$, cyclo-$C_3H_7$ and $C_4H_8$; either $R^3$, $R^5$, $R^6$ and $R^7$ are either (i), (ii), (iii), (iv) or (v):

(i) $R^5$, $R^6$ and $R^7$ are H; and $R^3$ is H, $NH_2$, $CH_3$ $CF_3$, halide, $C_2H_5NH$ or Ph, $R^4$ is H, $CF_3$, $NH_2$, $R^7$ is H or $CF_3$, and $R^5$ and $R^6$ are H; or (ii) $R^3$, $R^5$ and $R^6$ are H; and $R^4$ and $R^7$ together form 1,3-butadienyl, 4-dimethylamino- 1,3 butadienyl, 1-chloro-1,3-butadiene, or 4-chloro-1,3-butadienyl; or (iii) $R^4$, $R^5$ and $R^6$ are H; and $R^7$ and $R^3$ together form 1,3-butadienyl, 4-dimethylamino-1,3 butadienyl, 1-chloro-1,3-butadiene, 1-aza-1,3-butadienyl; or (iv) $R^4$ is H or $NH_2$, $R^5$ and $R^6$ are H; and $R^3$ is H, $NH_2$ and halide; $CH_3$, Br, Cl, F, $CF_3$, $NH_2$, $R^7$ is H, $CH_3$, Br, Cl, F, $NH_2$ or $CF_3$, and $R^5$ and $R^6$ are H; or (V) $R^3$, $R^5$, and $R^7$ are H are as defined in (i); and $R^4$ and $R^6$ are each independently selected from alkyl groups that contain from 1 to 6 carbons, and are straight or branched chains.

In more preferred embodiments, the compounds are N-(4-halo-isoxazolyl)sulfonamides in which $R^2$ is H, $CH_3$, $C_2H_5$, $C_2F_5$ or $CF_3$; and $R^3$, $R^4$, $R^5$, $R^6$ and $R^7$ are either (i) or (ii) as follows:

(i) $R^4$, $R^5$, $R^6$ and $R^7$ are each independently selected from H, halide, $NH_2$, $CF_3$, Ph and $CH_3$; $R^3$ is selected from H, NHOH, $NH_2$, $C_2H_5NH_2$, $(CH_3)_2NH$, Ph-CH $_2NH$, $NO_2$, F, Cl, Br, I, CN, $CH_3$, $(CH_3)_3C$, $C_5H_{11}$, $CH_3O$, n-$C_4H_9O$, $CH_2=CH$, Ph-$CH=CH$, $CH\equiv C$, Ph-$CH\equiv C$, Ph, 3-(ethyoxycarbonylmethyl)ureido, and 3-cyclohexylureido; or (ii) $R^3$, $R^5$ and $R^7$ are H; and $R^4$ and $R^6$ are each an alkyl group that contains from 1 to 3 carbons, which are straight or branched chains.

In yet more preferred embodiments, n is 1; $R^1$ is most preferably Br, Cl or $CH_3$; $R^2$ is $CH_3$, $C_2H_5$, or $CF_3$; and $R^3$, $R^4$, $R^6$ and $R^7$ are (i) or (ii) as follows:

(i) $R^3$ is H, $NH_2$, $CH_3$ $CF_3$, halide or $C_2H_5NH$; $R^4$, $R^5$ and $R^6$ are independently selected from H, $CF_3$, halide, particularly Br and Cl, $NH_2$; and $R^7$ is H, $CH_3$, $CH_2CH_5$, $(CH_3)CH$, F or $CF_3$; or (ii) $R^3$, $R^5$ and $R^7$ and $R^4$ and $R^6$ are independently selected from nitro, hydrogen, methyl or ethyl.

The following selected compounds are among the above compounds:

TABLE 3

| COMPOUND | $ET_A$ (µM) | $ET_B$ (µM) |
|---|---|---|
| N-(3,4-Dimethyl-5-isoxazolyl)-α-toluenesulfonamide | 7.5 ± 0.2 | 84.3 ± 9 |
| 2-nitro-N-(3,4-dimethyl-5isoxazolyl)-α-toluenesulfonamide | 23.8 | — | c. Compounds in which $Ar^2$ is a fused aromatic ring

Compounds in which $Ar^2$ contains fused aromatic rings and is selected from naphthyl, anthracenyl and phenanthryl are provided herein.

(1) $Ar^2$ is naphthyl

Compounds in which $Ar^2$ is naphthyl

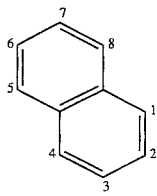

are provided herein. The compounds have formulae (X):

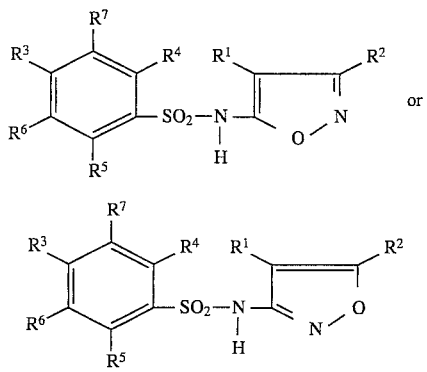

which $R^1$ and $R^2$ are as set forth above, $R^2$ is preferably H, lower alkyl or lower haloalkyl; $R^1$ is preferably halide or, if an increase in $ET_B$ affinity is desired, higher alkyl (about 8 to 15, preferably 9 to 13 carbons, which are straight or branched chains); $R^3$, $R^4$, $R^5$, $R^6$, and $R^7$ are selected from (i) or (ii):

(i) $R^4$ and $R^7$ together are substituted or unsubstituted 1,3-butadienyl, 4-dimethylamino-1,3 butadiene, 1-chloro-1,3-butadiene, 1-aza-1,3-butadienyl or 2-aza-1,3-butadienyl groups; and $R^3$, $R^5$ and $R^6$ are each selected independently from among H, NHOH, NH$_2$, NO$_2$, N$_3$, halide, pseudohalide, alkyl, alkenyl, alkynyl, aryl, heteroaryl, alkoxy, alkylamino, alkylthio, alkoxyalkyl, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons and the aryl portions contain from 3 up to about 10 carbons, preferably 6 carbons; or alternatively, (ii) $R^7$ and $R^3$ together are substituted or unsubstituted 1,3-butadienyl, 4-dimethylamino-1,3 butadiene, 1-chloro-1,3-butadiene, 1-aza-1,3-butadienyl or 2-aza- 1,3-butadienyl groups; and $R^4$, $R^5$ and $R^6$ are each selected independently from among H, NHOH, NH$_2$, NO$_2$, N$_3$, halide, pseudohalide, alkyl, alkenyl, alkynyl, aryl, heteroaryl, alkoxy, alkylamino, alkylthio, alkyalkoxy, alkylsulfinyl, alkylsulfonyl, aryloxy, arylamino, arylthio, arylsulfinyl, arylsulfonyl, haloalkyl, haloaryl, alkoxycarbonyl, alkylcarbonyl, arylcarbonyl, formyl, substituted or unsubstituted amido, substituted or unsubstituted ureido, where the alkyl, alkenyl, alkynl portions are straight or branched chains of from about 1 up to about 10 carbons, preferably, 1 to about 5 or 6 carbons and the aryl portions contain from 3 up to about 10 carbons, preferably 6 carbons. In preferred embodiments $R^2$ is H, CH$_3$, C$_2$H$_5$ or CF$_3$ and $R^1$ is halide or, in embodiments in which an increase in $ET_B$ activity is desired, $R^1$ is higher alkyl, in which the alkyl group contains between 8 and 15, preferably 9 and 13, carbons, which may be straight or branched chains.

In certain embodiments the compounds have formulae (XI):

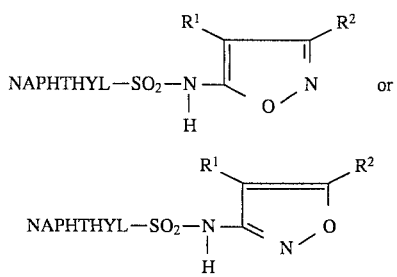

which is substituted with $R^4$, $R^5$ and $R^6$ which are selected independently, with the proviso that at least one of $R^4$, $R^5$ and $R^6$ is not hydrogen:

(a) hydrogen;

(b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

(c) halo;

(d) hydroxyl;

(e) cyano;

(f) nitro;

(g) —C(O)H or —C(O)R$^{27}$;

(h) —CO$_2$H or —CO$_2$R$^{27}$;

(i) —SH, —S(O)$_n$R$^{27}$, —S(O)$_m$—OH, —S(O)$_m$—OR$^{27}$, —O—S(O)$_m$—R$^{27}$, —O—S(O)$_m$OH, or —O—S(O)$_m$—OR$^{27}$;

(j) —W$^4$—NR$^{28}$R$^{29}$, or (k) —W$^4$—N(R$^{32}$)—W$^5$—NR$^{30}$R$^{31}$;

$R^1$ is halide or higher alkyl (greater than 8 carbons up to about 15);

$R^2$ is (a) hydrogen;

(b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

(c) hydroxyl;

(d) cyano;

(e) nitro;

—C(O)H or —C(O)R$^{27}$;

(f) —CO$_2$H or —CO$_2$R$^{27}$;

(g) —CO$_2$H or —CO$_2$R$^{27}$;

(h) —SH, —S(O)$_n$R$^{27}$, —S(O)$_m$—OH, —S(O)$_m$—OR$^{27}$, —O—S(O)$_m$—R$^{27}$, —O—S(O)$_m$OH or —O—S(O)$_m$—OR$^{27}$;

(i) —W$^4$—NR$^{28}$R$^{27}$; or (j) —W$^4$—N(R$^{32}$)—W$^6$—NR$^{30}$R$^{31}$;

$R^{27}$ is alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$.

$R^{28}$ is (a) hydrogen;

(b) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

(c) cyano;

(d) hydroxyl;

(e) —C(O)H or —C(O)R$^{27}$;

(f) —$CO_2H$ or —$CO_2R^{27}$;
(g) —SH, —$S(O)_nR^{27}$, —$S(O)_m$—OH, —$S(O)_m$—$OR^{27}$, —O—$S(O)_m$—$R^{27}$, —O—$S(O)_m$OH, or —O—$S(O)_m$—$OR^{27}$, except when $W^4$ is —$S(O)_n$—;

$R^{29}$ is (a) hydrogen;
(b) —C(O)H or —$C(O)R^{27}$, except when $W^4$ is —C(O)— and $R^{28}$ is —C(O)H, —$C(O)R^{27}$, —$CO_2H$, of —$CO_2R^{27}$,
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$, or $R^{28}$ and $R^{29}$ together are aklylene or alkenylene (either of which may be substituted with $W^1$, $W^2$ and $W^3$), completing 3- to 8-membered saturated, unsaturated or aromatic ring together with the nitrogen atom to which they are attached;

$R^{30}$ is (a) hydrogen;
(b) hydroxyl;
(c) —C(O)H or —$C(O)R^{27}$;
(d) —$CO_2H$ or —$CO_2R^{27}$;
(e) —SH, —$S(O)_nR^{27}$, —$S(O)_m$—OH, —$S(O)_m$—$OR^{27}$, —O—$S(O)_m$—$R^{27}$, —O—$S(O)_m$OH, or —O—$S(O)_m$—$OR^{27}$;
(f) alkyl, alkynyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{31}$ is (a) hydrogen;
(b) —C(O)H or —$C(O)R^{27}$, except when $W^6$ is —C(O)— and $R^{30}$ is —C(O)H, —$C(O)R^{27}$, —$CO_2H$, or —$CO_2R^{27}$;
(c) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

$R^{32}$ is (a) hydrogen;
(b) hydroxyl, $CO_2R^{27}$ or $CO_2H$, except when one of $R^{30}$ and $R^{31}$ is hydroxyl, $CO_2R^{27}$ or $CO_2H$;
(c) —C(O)H or —$C(O)R^{27}$; or
(d) alkyl, alkenyl, alkynyl, alkoxy, cycloalkyl, cycloalkylalkyl, cycloalkenyl, cycloalkenylalkyl, aryl, or aralkyl, any of which may be substituted with $W^1$, $W^2$ and $W^3$;

or any two of $R^{30}$, $R^{31}$ and $R^{32}$ together are alkylene or alkenylene (either of which may be substituted with $W^1$, $W^2$ and $W^3$), completing a 3- to 8-membered saturated, unsaturated or aromatic ring together with the atoms to which they are attached;

$W^1$, $W^2$ and $W^3$ are each independently (a) hydrogen;
(b) halo;
(c) hydroxy;
(d) alkoxy;
(e) —SH, —$S(O)_nW^6$, —$S(O)_m$—OH, —$S(O)_m$—$OW^6$, —O—$S(O)_m$—$W^6$, —O—$S(O)_m$OH, or —O—$S(O)_m$—$OW^6$;
(f) oxo;
(g) nitro;
(h) cyano;
(i) —C(O)H or —$C(O)W^6$;
(j) —$CO_2H$ or —$C(O)_2W^6$; or
(k) —$NW^7W^8$, —$C(O)NW^7W^8$, or —$S(O)_nW^7W^8$;

$W^4$ and $W^5$ are each independently (a) a single bond;
(b) —$S(O)_n$—:
(c) —C(O)—;
(d) —C(S)—; or
(e) alkyl, alkenyl, alkynyl, cycloalkyl, cycloalkylalkyl, cycloalkenyl, cycloalkenylalkyl, aryl, or aralkyl, any of which may be substituted with $W^1$, $W^2$ and $W^3$;

$W^6$, $W^7$ and $W^8$ are each independently hydrogen, alkyl, alkenyl, alkynyl, cycloalkyl, cycloalkylalkyl, cycloalkenyl, cycloalkenylalkyl, aryl, or aralkyl, or $W^7$ and $W^8$ together are alkylene or alkenylene, completing a 3- to 8-membered saturated, unsaturated or aromatic ring together with the nitrogen atom to which they are attached;

m is 1 or 2; and n is 0, 1, or 2.

At least one of $R^4$, $R^5$ and $R^6$ is preferably di-loweralkylamino or loweralkylamino and the others of $R^4$, $R^5$ and $R^6$ is hydrogen or lower alkyl.

In all preferred embodiments the sulfonamide is linked at position 1 or 2, preferably 1, of the napthyl :group and at least one of the subsituents is at position 5.

Naphthalenesulfonamides were synthesized and tested using the exemplified assays (see, EXAMPLES) and selected results are set forth in the Table 4 (the 4-haloisoxazole compounds are preferred).

TABLE 4

| COMPOUND | $ET_A$ (μM)* | $ET_B$ (μM)* |
| --- | --- | --- |
| N-(3,4-dimethyl-5-isoxazolyl)-1-naphthalenesulfonamide | 0.44 ± 0.05 | 49 ± 9 |
| 6-chloro-N-(3,4-dimethyl-5-isoxazolyl)-2-naphthalenesulfonamide | 3.4 ± 0.3 | 7.8 ± 0.4 |
| 5-chloro-N-(3,4-dimethyl-5-isoxazolyl)-1-naphthalenesulfonamide | 2.4 ± 1 | 20 ± 5 |
| N-(4-bromo-3-methyl-5-isoxazolyl)-1-naphthalenesulfonamide | 0.086 | 14.9 ± 5 |
| N-(4-bromo-5-methyl-3-isoxazolyl)-1-naphthalenesulfonamide | 0.1 | 16 |
| N-(4-methyl-3-trifluoromethyl-5-isoxazolyl)-1-naphthalenesulfonamide | 0.64 | 62 |
| N-(4-ethyl-3-trifluoromethyl-5-isoxazolyl)-1-naphthalenesulfonamide | 0.26 | 40 |
| N-(4-bromo-3-ethyl-5-isoxazolyl)-1-naphthalenesulfonamide | 0.97 | 41 |

TABLE 4-continued

| COMPOUND | $ET_A$ (μM)* | $ET_B$ (μM)* |
| --- | --- | --- |
| N-(4-bromo-3-methyl-5-isoxazolyl)-1-naphthalenesulfonamide | 0.11 | 16 |
| 5-dimethylamino-N-(3,4-dimethyl-isoxazoyl)-1-napthalenesulfonamide | 0.0064 | 14 |
| 5-dimethylamino-N-(4-bromo-3-methyl-5-isoxazoyl)-1-napthalenesulfonamide | 0.0012 | 3.07 |
| 5-dimethylamino-N-(4-bromo-5-methyl-3-isoxazoyl)-1-napthalenesulfonamide | 0.002 | 2.5 |

*results generally from 1 to 4 experiments (2) phenanthryl and anthracenyl

Isoxazolyl-sulfonamides in which $Ar^2$ contains three fused aromatic rings are also provided herein. $R^1$ and $R^2$ are selected as described above for the compounds in which $Ar^2$ is phenyl or biphenyl and n> 0. The fused rings may be substituted with one or more substituents selected from $R^{13}$ and $R^{26}$ in which $R^{26}$ and $R^{13}$ are independently selected from H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons.

More preferably $R^1$ is halide or methyl; $R^2$ is selected from alkyl, lower alkenyl, lower alkynl, and lower haloalkyl; and $R^{26}$ and $R^{13}$ are selected from H, lower alkyl, haloalkyl and halide. In more preferred embodiments, $R^1$ is Cl, Br or $CH_3$; $R^2$ is selected from H, $CH_3$, $C_2H_5$, $CF_3$, n-$C_3H_7$, cyclo-$C_3H_7$ and $C_4H_8$; $R^{26}$ and $R^{13}$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2=CH$. In yet more preferred embodiments, $R^2$ is H, $CH_3$, $C_2H_5$, or $CF_3$; $R^{26}$ and $R^{13}$ are independently selected from H, $CH_3$, $C_2H_5$, $CF_3$, and halide.

Exemplary compounds include N-(4-bromo-3-methyl-5-isoxazolyl)phenanthrene- 3-sulfonamide, N-(4-bromo-5-methyl-3-isoxazolyl)phenanthrene-3-sulfonamide and N-(3,4-dimethyl-5-isoxazolylphenanthrene-3-sulfonamide.
Selected results for such componds are set forth in Table 5:

TABLE 5

| COMPOUND | $ET_A$ (μM)* | $ET_B$ (μM)* |
| --- | --- | --- |
| N-(4-bromo-3-methyl-5-isoxazolyl)-9,10-dioxoanthracene-2-sulfonamide | 4.34 | 2.01 |
| N-(4-bromo-3-methyl-5-isoxazolyl)-2-phenanthrenesulfonamidesulfonamide | ~1.9 | ~0.06 |
| N-(3,4-dimethyl-5-isoxazolyl-2-phenanthrenesulfonamidesulfonamide | ~3.4 | 0.23 |

*preliminary results

2. Compounds in which $Ar^2$ is contains a heterocyclic ring or fused rings with at least one heterocycyclic ring Compounds in which $Ar^2$ is a heterocycle including sulfonamides in which $Ar^2$ is five-membered heterocyclic ring compound with one heteroatom and fused ring analogs thereof, compounds in which $Ar^2$ is a five-membered. heterocycle with two or more heteroatoms and fused ring analogs thereof, compounds in which $Ar^2$ is a six-membered heterocyclic ring compound with one heteroatom and fused ring analogs thereof, compounds in which $Ar^2$ is a six-membered heterocycle with two or more heteroatoms and fused ring analogs thereof are provided.

Compounds in which which $Ar^2$ is a five-membered heterocycle with one heteroatom include, but are not limited to, compounds in which $Ar^2$ is thiophenyl, furyl, pyrrolyl, 2H-pyrrolyl, 2-pyrrolinyl, 3-pyrrolinyl and pyrrolidinyl and other such rings. Compounds in which $Ar^2$ is a is a fused ring analog of a 5-membered heterocyle with one heteroatom, include, but are not limited to compounds in which $Ar^2$ is benzofuryl, benzothiophenyl (thianaphthyl) indolyl, indolizinyl, and isoindole.

Compounds in which $Ar^2$ is a 5-membered heterocycle with two or more heteroatoms and fused ring analogs thereof include, but are not limited to, compounds in which $Ar^2$ is oxazolyl, thiazolyl, imidazolyl, 2-imidazolinyl, imidaolidinyl, 1,3-dioxaolanyl, pyrazolyl, 2-pyrazolinyl, pyrazolidinyl, isoxoxaolyl, isothiazolyl, 1,2,3-oxadiazolyl, 1,2,3-triazolyl, 1,3,4-thiadiazolyl, 1H-indazolyl, benzoxazolyl, benzimidazolyl and benzothiazolyl.

Compounds in which $Ar^2$ is a 6-membered heterocycle with one heteroatom and fused ring analogs thereof include, but are not limited to, compounds in which $Ar^2$ is pyridinly, quinolinyl, isoquinolynl, acridine, 4H-quinolizine, 2H-pyran, 4H-pyran, and piperidinyl.

Compounds in which $Ar^2$ is a 6-membered heterocycle with two or more heteroatoms and fused ring analogs thereof include, but are not limited to, pyrimidinyl, pyrazinyl, piperazinyl, triazinyl, cinnolinyl, phthalazinyl, quinazolinyl, quinoxalinyl, 1,8-napthyridinyl, pterdinyl, 1,4-doxanyl, morpholinyl, thiomorpholinyl, morpholinyl, phenazinyl, phenythiazinyl, phenoxazinyl, quniazolinyl, quinoxalinyl, naphthyrindinyl and pteridinyl.

a. $Ar^2$ is thiophenyl, furyl and pyrrolyl

In certain embodiments, $Ar^2$ is represented by the formulae (XII):

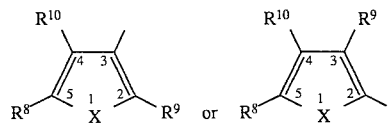

that can be substituted at any or all positions or is an analog of compounds of formula (IV) in which the substituents form fused aromatic, aliphatic or heterocyclic rings; and in which X is $NR^{11}$, O, or S, and $R^{11}$, which is hydrogen or contains up to about 30 carbon atoms, preferably 1 to 10, more preferably 1 to 6, and is selected as defined above. $R^8$, $R^9$, $R^{10}$ are selected as described above.

Thus, in certain embodiments described in detail herein, $Ar^2$ is thiophenyl, furyl, pyrrolyl or a group, such as benzofuryl, thianaphthyl or indolyl, that is a derivative of or analog, as described below, of a thiophenyl, furyl, pyrroly group, $Ar^1$ is preferably N-(5-isoxazolyl) or N-(3-isoxazolyl), and the compounds are represented by the formulae XIII:

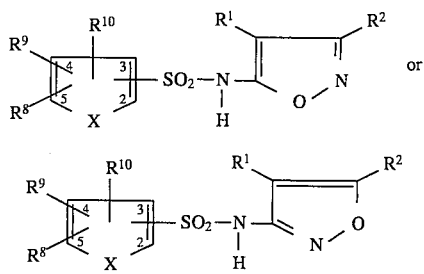

in which $R^1$, $R^2$, are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heterolaryl, alkoxy, alkylamino, alkylthio, haloalkoxy, haloalkyl, alkylsufinyl, alkylsulfonyl, aryloxy, arylamino, arylthio, arylsufinyl, arylsulfonyl, aminocarbonyl, haloalkyl, haloaryl, alkoxycarbonyl, alkylcarbonyl, arylcarbonyl, formyl, substituted or unsubstituted amido, substituted or unsubstituted ureido, in which the alkyl, alkenyl and alkynyl portions are either straight or branched chains that contain from 1 up to about 10 carbon atoms, and the aryl portions contain from about 4 to about 14 carbons, except the $R^2$ is not halide, pseudohalide or higher alkyl; or, (ii) $R^1$ and $R^2$ together form $—(CH_2)_n$, where n is 3 to 6; or, (iii) $R^1$ and $R^2$ together form 1,3-butadienyl; and X, $R^8$, $R^9$ and $R^{10}$ are selected as defined above.

The more preferred compounds of formulae I and and II provided herein are compounds in which $Ar^1$ is N-(5-isoxazolyl) or N-(3-isoxazolyl) that can be represented by the formulae XIV:

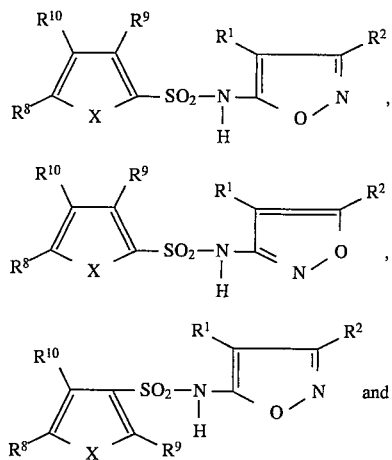

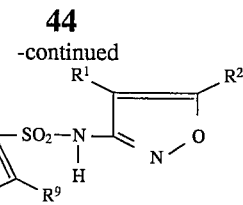

in which:

$R^1$ and $R^2$ are either (i), (ii) or (iii) as follows:

(i) $R^1$ and $R^2$ are each independently selected from H, $NH_2$, $NO_2$, halide, pseudohalide, alkyl, alkenyl, alkynyl, aryl, arylalkyl, heteroaryl, alkoxy, alkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons; or, (ii) $R^1$ and $R^2$ together form $—(CH_2)_n$, where n is 3 to 6; or, (iii) $R^1$ and $R^2$ together form 1,3-butadienyl; X is O, S, NH or $NR^{11}$ in which $R^{11}$, which contains up to about 30–50 atoms, generally 1 to 20 atoms, and which is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$, $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; m is 0–2; $R^{11}$ and $R^{15}$, are unsubstituted or are substituted with one or more substituents each independently selected from Z, which is hydrogen, halide, pseudoahlide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(C))R^{17}$ and $S(C))_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$ and $R^{16}$ may be further substituted with substituents selected from Z;

and $R^8$, $R^9$, $R^{10}$, which each, when not hydrogen, contain up to about 30 carbon atoms or more, generally fewer than about 16, are each independently selected as follows from (i) or (ii):

(i) $R^8$, $R^9$ and $R^{10}$ are each independently selected from hydrogen, halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0–2, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from: hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl; and any of the groups set forth for $R^8$, $R^9$ and $^{10}$ are unsubstituted or substituted with any substituents set forth for Z, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0–2, NHOH, $NR^{22}R^{21}$, $NO_2$, $N_3$, $OR^{21}$, $R_{22}NCOR^{21}$ and $CONR^{22}R^{21}$; $R^{22}$ is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl and cycloalkynyl, $C(O)R^{25}$ and $S(O)_nR^{25}$ in which n is 0–2; $R^{24}$ is hydrogen, alkyl, alkenyl, alkynyl, aryl, alkylaryl, heterocycle, aralkyl, aralkoxy, cycloalkyl, cycloalkenyl or cycloalkynyl; and $R^{25}$ is hydrogen, alkyl, alkenyl, alkynyl, aryl, alkylaryl, heterocycle, aralkyl, aralkoxy, cycloalkyl, cycloalkenyl or cycloalkynyl; any of the preceding groups, including $R^8$, $R^9$, $R^{10}$, $R^{18}$, $R^{19}$, $R^{20}$, $R^{21}$, $R^{22}$, $R^{23}$, $R^{24}$ and $R^{25}$ may be unsubstituted, except as specified, or may be further substituted with substituents selected from Z, which is is hydrogen, halide, pseudoahlide, alkyl, alkoxy, alkenyl, alkynyl, aryl, aryloxy, heterocycle, aralkyl, aralkoxy, cycloalkyl, cycloalkenyl, cycloalkynyl; or (ii) any two of $R^8$, $R^9$ and $R^{10}$ form an aromatic or heteroaromatic ring or an alicyclic or heterocyclic ring, which is saturated or unsaturated, containing from about 3 to about 16 members, preferably 3 to about 10 members, more preferably 5 to 7 members, and which is unsubstituted or substituted with one or more substituents in each each substituent is independently selected from Z; and the other of $R^8$, $R^9$ and $R^{10}$ is selected as in (i).

In the above embodiments, the alkyl, alkyny and alkenyl portions are straight or branched chains, acyclic or cyclic, and have from about 1 up to about 10 carbons; in certain of the more preferred embodiments they have from 1–6 carbons, and they can have fewer than 6 carbons. The aryl, homocyclic and heterocyclic groups can have from 3 to 16, generally, 3–7, more often 5–7 members in the rings, and may be single or fused rings. The ring size and carbon chain length are selected such that the resulting molecule binds to exhibits activity as an endothelin antagonist or agonist as evidenced by in vitro or in vivo tests, particularly the tests exemplified herein.

In any of the above preferred embodiments: $R^1$ and $R^2$ are preferably selected independently from alkyl, lower alkenyl, lower alkynl, lower haloalkyl, halide, pseudohalide and H, except that $R^2$ is not halide or pseudohalide or higher alkyl.

In preferred embodiments: X is S, O, $NR^{11}$ in which $R^{11}$ is aryl, hydrogen, or lower alkyl, preferably, a substituted or unsubstituted aryl, particularly phenyl, preferably unsubstituted or substituted with lower alkyl or halogen hydrogen or lower alkyl; $R^1$ is hydrogen, halide, pseudohalide, lower alkyl or lower haloalkyl, most preferably halide; $R^2$ is hydrogen, lower alkyl or lower haloalkyl; and $R^8$, $R^9$ and $R^{10}$ are each selected independently from from hydrogen, halide, pseudohalide, lower alkyl, lower aryl, lower heterocycle, lower aralkyl, $S(O)_nR^{18}$ in which n is 0–2, $C(O)R^{18}$, $CO_2R^{18}$, $NO_2$ $OR^{18}$ or $CONR^{19}R^{18}$; $R^{19}$ is preferably hydrogen, lower alkyl, and lower aryl, $C(O)R^{20}$, $S(O)_nR^{20}$ in which n is 0–2; $R^{18}$ is preferably hydrogen, halide, lower alkyl or lower aryl, and $R^{20}$ is preferably hydrogen, halide or lower alkyl; and Z is hydrogen, halide, pseudohalide, lower alkyl or lower pseudohaloalkyl or lower haloalkyl. In particular, at least one of $R^8$, $R^9$ and $R^{10}$ is selected from methyl, phenyl, pyrazolyl, isoxazolyl, carbomethoxy, carboxamide, halide, hydrogen, isopropylphenyl, pyridyl, carboxyl, phenyl, phenylaminocarbonyl, benzenesulfonyl, loweralkylphenylaminocarbonyl, biphenylaminocarbonyl, (lower)haloalkoxyphenylaminocarbonyl and halophenylaminocarbonyl and, preferably, two of $R^8$, $R^9$ and $R^{10}$ are hydrogen, halide or lower alkyl. In more preferred of these embodiments X is S.

In more preferred embodiments, two of $R^8$, $R^9$ and $R^{10}$ are hydrogen, halide or lower alkyl and the other is hydrogen, halide, pseudohalide, lower alkyl, lower aryl, heterolower aryl, lower aralkyl $C(O)R^{18}$, $CO_2R^{18}$, $NO_2$, $OR^{18}$ or $CONR^{19}R^{18}$. In yet more preferred embodiments $R^{19}$ is phenyl and $R^{18}$ is hydrogen, halide or lower alkyl. In more preferred of these embodiments, two of $R^8$, $R^9$ and $R^{10}$ are hydrogen or lower alkyl and the other is halide, lower alkyl, $C(O)R^{18}$, $CO_2R^{18}$, $NO_2$, $OR^{18}$ or $CONR^{19}R^{18}$; $R^{18}$ is hydrogen or lower alkyl in all embodiments, $R^1$ is preferably halide, H, $CH_3$ or $C_2H_5$, and $R^2$ is H, $CH_3$, $C_2H_5$, $C_2F_5$ or $CF_3$. In yet more preferred embodiments, $R^1$ preferably Br, Cl or $CH_3$; $R^2$ is H, $CH_3$, $C_2H_5$, or $CF_3$.

In certain preferred embodiments, $R^8$ and $R^{10}$ are H, halide or lower alkyl; and $R^9$ is any of the above listed substituents, and particularly, when a potent $ET_A$ antagonist is desired is a substituted aminocarbonyl. In other preferrred embodiments it is preferred that $R^9$ and $R^{10}$ are H or lower alkyl and $R^8$ is any of the above-listed substituents. In the preferred of these embodiments, $R^1$ is halide, H, $CH_3$ or $C_2H_5$, and $R^2$ is H, $CH_3$, $C_2H_5$, $C_2F_5$ or $CF_3$. In yet more preferred embodiments, $R^1$ is Br, Cl or $CH_3$; and $R^2$ is H, $CH_3$, $C_2H_5$, or $CF_3$, In embodiments in which $ET_B$ antagonists are desired, it is preferred that $R^9$ and $R^{10}$ are H or lower alkyl and $R^8$ is a heterocyclic or aromatic ring of preferably from 3 to 14, more preferably, 5 to 7, members in the ring. In particular, if X is S, $R^9$ and $R^{10}$ are H or lower alkyl, and $R^8$, is aryl, particularly unsubstituted or substituted phenyl, such as 4-ethylphenyl. If X is N, then $R^{11}$ is aryl, particularlyl unsubstituted phenyl or substituted phenyl, such as isopropylphenyl and $R^8$, $R^9$ and $R^{10}$ are preferably H, halide or lower alkyl.

In all embodiments, $R^1$ is preferably halide or lower alkyl, most preferably Br, and the compounds are, with reference to formulae IV, 2- or 3-sulfonamides, particularly thiophene sulfonamides.

The most preferred compounds provided herein have an $IC_{50}$ for $ET_A$ receptors in the assays exemplified herein between about 0.002 μM and 0.1 μM (see, e..q., Table 6). These compounds include: N-(4-bromo-3-methyl-5-isoxazolyl)- 2-[N-(4-methoxyphenyl)aminocarbonyl]thiophene-3-sulfonamide; N-(4-bromo-3-methyl-5-isoxazolyl)- 2-[N-(3-methoxyphenyl)aminocarbonyl]thiophene-
3-sulfonamide; N-(4-bromo-3-methyl- 5-isoxazolyl)-2-(N-phenylaminocarbonyl)thiophene- 3-sulfonamide; N-(4-bromo-5-methyl-3-isoxazolyl)- 2-(N-phenylaminocarbonyl)thiophene- 3-sulfonamide; N-(3,4-dimethyl-5-isoxazolyl)- 2-(N-phenylaminocarbonyl)thiophene-3-sulfonamide; N-( 4-bromo-3-methyl-5-isoxazolyl)- 2,5-dimethylthiophene-3-sulfonamide; N-(4-bromo- 3-methyl-5-isoxazolyl)-2-(carbomethoxy)thiophene- 3-sulfonamide; N-(4-bromo-3-methyl-5-isoxazolyl)thiophene- 2-sulfonamide; N-(4-bromo-3-methyl- 5-isoxazolyl)-2-[N-(4-biphenyl)aminocarbonyl]thiophene- 3-sulfonamide; N-(4-bromo-3-methyl-5-isoxazolyl)- 2-[N-(2-methoxyphenyl)aminocarbonyl]thiophene-3-sulfonamide; N-(4-bromo- 3-methyl-5-isoxazoly)-2-(N-benzylaminocarbonyl)thiophene-3-sulfonamide; N-(4-bromo-3-methyl-5- isoxazolyl)-2-[N-(4-ethylphenyl)aminocarbonyl]thiophene-3-sulfonamide; N-(4-bromo-3-methyl-5-isoN-(4-bromo-3-methyl- 5-isoxazolyl)-2-[N-(4-biphenyl)aminocarbonyl]thiophene-3-sulfonamide; N-(4-bromo-3-methyl-5-isoxazolyl)-2-[N-(4-methoxyphenyl)aminocarbonyl]thiophene- 3-sulfonamide; N-(4-bromo-3-methyl-5-isoxazolyl)-3-phenylthiophene-2-sulfonamide; N-(4-bromo-3-methyl-5-isoxazolyl)-4-phenylthiophene-2-sulfonamide; N-(4-bromo-3-methyl-5-isoxazolyl)-3-phenoxythiophene-2-sulfonamide; N-(4-bromo-3-methyl-5-isoxazolyl)-2-[N-(4-methylphenyl)aminocarbonyl]thiophene- 3-sulfonamide; N-(4-bromo-3-methyl-5-isoxazolyl)-2-[N-( 4-isopropylphenyl)aminocarbonyl]thiophene- 3-sulfonamide; N-(4-bromo-3-methyl-5-isoxazolyl)- 2-[N-(4-t-butylphenyl)aminocarbonyl]thiophene-3-sulfonamide; N-( 4-bromo-3-methyl-5-isoxazolyl)-2-[N-(4-n-butylphenyl)aminocarbonyl]thiophene- 3-sulfonamide; and N-(4-bromo-3-methyl-5-isoxazolyl)-2-[N-( 4-sec-butylphenyl)aminocarbonyl]thiophene-3-sulfonamide.

Other preferred compounds include those that have an $IC_{50}$ for $ET_B$ receptors, as measured in the assays herein, of between about 0.05 μM and 1 μM. These include compounds, such as N-(4-bromo-3-methyl-5-isoxazolyl)- 5-benzenesulfonylthiophene-2-sulfonamide, N-(4-bromo-3-methyl- 5-isoxazolyl)-1-(4'-isopropylphenyl)pyrrole-2-sulfonamide; N-(4-bromo-3-methyl- 5-isoxazolyl)-1-(4'-isopropylphenyl)pyrrole-3-sulfonamide; N-(4-bromo-3-methyl-5-isoxazolyl)-2-{3-[1-methyl-5- (trifluoromethyl)pyrazolyl]}thiophene-5-sulfonamide; N-(4-bromo- 3-methyl-5-isoxazolyl)-2-[N-(4-biphenyl)aminocarbonyl]thiophene-3-sulfonamide; N-(4-bromo-3-methyl-5-isoxazolyl)-2-[N-(4-ethylphenyl)aminocarbonyl]thiophene- 3-sulfonamide; N-(4-bromo-3-methyl-5-isoxazolyl)-5-thienylthiophene-2-sulfonamide; and N-(4-bromo-3-methyl-5-isoxazolyl)-5-(4-ethylphenyl)thiophene-2-sulfonamide.

TABLE 6

| COMPOUND | $ET_A$ (μM)* | $ET_B$ (μM)* |
|---|---|---|
| N-(4-bromo-3-methyl-5-isoxazolyl)-5-bromothiophene-2-sulfonamide | 0.314 | 2.26 |
| N-(4-bromo-3-methyl-5-isoxazolyl)-5-(2'-thienyl)thiophene-2-sulfonamide | 5.1 | 0.363 |
| N-(4-bromo-3-methyl-5-isoxazolyl)-3-phenoxythiophene-2-sulfonamide | 0.103 | 3.46 |
| N-(3,4-dimethyl-5-isoxazolyl)benzofuran-2-sulfonamide | 5.22 | 38.4 |
| N-(3,4-dimethyl-5-isoxazolyl)furan-2-sulfonamide | 3.13 | — |
| N-(4-bromo-3-methyl-5-isoxazolyl)-5-phenylfuran-2-sulfonamide | 0.857 | 2.43 |
| N-(4-bromo-3-methyl-5-isoxazolyl)furan-2-sulfonamide | 0.75 | 88.1 |
| N-(4-bromo-3-methyl-5-isoxazolyl)-2,5-dimethylfuran-3-sulfonamide | 0.46 | 36.5 |
| N-(4-bromo-3-methyl-5-isoxazolyl)-5-(phenthio)furan-2-sulfonamide | 5.0 | 7.0 |
| N-(4-Bromo-3-methyl-5-isoxazolyl)-1-(phenyl)pyrrole-2-sulfonamide | 18.1 | 8.7 |
| N-(4-Bromo-3-methyl-5-isoxazolyl)-1-(4'-isopropylphenyl)pyrrole-2-sulfonamide | 11.4 | 0.166 |
| N-(4-Bromo-3-methyl-5-isoxazolyl)-1-(4'-isopropylphenyl)pyrrole-3-sulfonamide | 0.838 | 0.211 |
| (4-bromo-3-methyl-5-isoxazolyl)-1-(4'-biphenyl)pyrrole-2-sulfonamide | 9.17 | 7.84 |
| N-(4-bromo-3-methyl-5-isoxazolyl)-2-thiophenesulfonamide | 0.095 ± 0.07 | 27.7 ± 15.0 |
| N-(4-bromo-5-methyl-3-isoxazolyl)thiophene-2-sulfonamide | 0.211 | 27.3 |
| N-(4-bromo-3-methyl-5-isoxazolyl)thiophene-3-sulfonamide | 0.135 | 23.4 |
| 5-(3-isoxazolyl)-N-(3-methyl-5-isoxazolyl)-2-thiophenesulfonamide | 5.6 | 6.7 |
| N-(4-Bromo-3-methyl-5-isoxazolyl)-5-(2-pyridyl)thiophene-2-sulfonamide | 3.84 | 2.70 |
| N-(4-Bromo-3-methyl-5-isoxazolyl)-4,5-dibromothiophene-2-sulfonamide | 0.281 | 2.58 |
| N-(4-Bromo-3-methyl-5-isoxazolyl)-5-chloro-3-methylbenzo[b]thiophene-2-sulfonamide | 0.96 | 1.63 |
| N-(4-Bromo-3-methyl-5-isoxazolyl)-5-(4-chlorobenzamidomethyl)thiophene-2-sulfonamide | 0.311 | 2.57 |
| N-(4-Bromo-3-methyl-5-isoxazolyl)-4-benzenesulfonylthiophene-2-sulfonamide | 0.383 | — |
| 4-bromo-5-chloro-N-(4-Bromo-3-methyl-5-isoxazolyl)-thiophene-2-sulfonamide | 0.359 | 2.67 |
| N-(4-Bromo-3-methyl-5-isoxazolyl)-2,5-dimethylthiophene-3-sulfonamide | 0.0956 | 7.8 |
| N-(4-Bromo-3-methyl-5-isoxazolyl)-4,5-dichlorothiophene-2-sulfonamide | ~0.45 | ~4.9 |
| N-(4-Bromo-3-methyl-5-isoxazolyl)-4-bromo-2,5-dichlorothiophene-3-sulfonamide | ~0.28 | 10.4 |
| N-(4-Bromo-3-methyl-5-isoxazolyl)-2,5-dichlorothiophene-3-sulfonamide | ~0.39 | 2.62 |

TABLE 6-continued

| COMPOUND | ET$_A$ (μM)* | ET$_B$ (μM)* |
|---|---|---|
| N-(4-Bromo-3-methyl-5-isoxazolyl)-5-{3-[1-methyl-5-(trifluoromethyl)pyrazolyl]}thiophene-2-sulfonamide | ~6.7 | ~0.36 |
| N-(4-Bromo-3-methyl-5-isoxazolyl)-5-benzenesulfonylthiophene-2-sulfonamide | 0.570 | 0.333 |
| N-(4-bromo-3-methyl-5-isoxazolyl)-2-(carbomethoxy)thiophene-3-sulfonamide | 0.0208 | 98.1 |
| N-(3,4-dimethyl-5-isoxazolyl-5-phenylthiophen-2-sulfonamide | 2.55 | 1.29 |
| N-(4-bromo-3-methyl-5-isoxazolyl)-2-(N-phenylaminocarbonyl)thiophene-3-sulfonamide | 0.0054 | 18.8 |
| N-(4-bromo-5-methyl-3-isoxazolyl)-2-(N-phenylaminocarbonyl)thiophene-3-sulfonamide | — | — |
| N-(4-chloro-3-methyl-5-isoxazolyl)-2-(N-phenylaminocarbonyl)thiophene-3-sulfonamide | — | — |
| N-(3,4-dimethyl-5-isoxazolyl)-2-(carboxyl)thiophene-3-sulfonamide | 2.64 | >~100 |
| N-(4-chloro-3-methyl-5-isoxazolyl))-2-(carbomethoxy)thiophene-3-sulfonamide | | |
| N-(3,4-dimethyl-5-isoxazolyl)-2-(N-phenylaminocarbonyl)thiophene-3-sulfonamide | 0.0182 | ~170 |
| N-(3,4-dimethyl-5-isoxazolyl)-2-(carbomethoxy)thiophene-3-sulfonamide | 0.367 | — |
| N-(4-Bromo-3-methyl-5-isoxazolyl)-2-(carboxyl)thiophene-3-sulfonamide | ~0.6 | ~67 |
| N-(4-Bromo-3-methyl-5-isoxazolyl)-2-[N-(4-methoxyphenyl)aminocarbonyl]thiophene-3-sulfonamide | 0.002 | 2.12 |
| N-(4-Bromo-3-methyl-5-isoxazolyl)-2-[N-(3-methoxyphenyl)aminocarbonyl]thiophene-3-sulfonamide | 0.003 | 5.86 |
| N-(4-Bromo-3-methyl-5-isoxazolyl)-2-[N-(2-methoxyphenyl)aminocarbonyl]thiophene-3-sulfonamide | 0.0116 | 13.2 |
| N-(4-Bromo-3-methyl-5-isoxazolyl)-2-(N-benzylaminocarbonyl)thiophene-3-sulfonamide | 0.013 | 12.7 |
| N-(4-Bromo-3-methyl-5-isoxazolyl)-2-[N-(4-ethylphenyl)aminocarbonyl]thiophene-3-sulfonamide | 0.0016 | 0.849 |
| N-(4-Bromo-3-methyl-5-isoxazolyl)-2-[N-(4-biphenyl)aminocarbonyl]thiophene-3-sulfonamide | 0.0376 | 0.912 |
| N-(3,4-dimethyl-5-isoxazolyl)-3-methoxythiophene-2-sulfonamide | 2.5 | 45.5 |
| N-(4-bromo-3-methyl-5-isoxazolyl)-5-(4-ethylphenyl)thiophene-2-sulfonamide | 3.23 | 0.0855 |
| N-(4-bromo-3-methyl-5-isoxazolyl)-3-phenythiophene-2-sulfonamide | 0.0547 | 11.1 |
| N-(4-bromo-3-methyl-5-isoxazolyl)-4-phenylthiophene-2-sulfonamide | 0.224 | 1.17 |
| N-(3,4-dimethyl-5-isoxazolyl)benzo[b]thiophene-2-sulfonamide | 7.22 | 11.1 |
| N-(4-bromo-3-methyl-5-isoxazolyl)-2-phenylthiophene-3-sulfonamide | — | — |
| N-(4-chloro-3-methyl-5-isoxazolyl)-2-(N-phenylaminocarbonyl)thiophene-3-sulfonamide | — | — |
| N-(4-bromo-3-methyl-5-isoxazolyl)-5-benzylthiophene-2-sulfonamide | — | — |
| N-(4-chloro-3-methyl-5-isoxazolyl)-2-carboxythiophene-3-sulfonamide | — | — |
| N-(4-bromo-3-methyl-5-isoxazolyl)-5-(4'-isopropylphenyl))thiophene-2-sulfonamide | 01.6 | 0.3 |
| 822N-(4-bromo-3-methyl-5-isoxazolyl)-4-(4'-isopropylphenyl))thiophene-2-sulfonamide | 5.5 | 1.3 |
| N-(4-bromo-3-methyl-5-isoxazolyl)-5-(4'-propylphenyl))thiophene-2-sulfonamide | 5.6 | 0.51 |
| N-(4-bromo-3-methyl-5-isoxazolyl)-2-[-(4-tolulyl-aminocarbonyl]thiophene-3-sulfonamide | <0.01** | 1.67** |
| N-(4-bromo-3-methyl-5-isoxazolyl)-2-[N-(4-isopropylphenyl)aminocarbonyl]thiophene-3-sulfonamide | <0.01** | 1.13** |
| N-(4-bromo-3-methyl-5-isoxazolyl)-2-(4-t-butylphenyl)aminocarbonylthiophene-3-sulfonamide | 0.011** | 2.82** |
| N-(4-bromo-3-methyl-5-isoxazolyl)-2-(4-butylphenyl)aminocarbonylthiophene-3-sulfonamide | 0.044** | 2.84** |
| N-(4-bromo-3-methyl-5-isoxazolyl)-2-[N-(4-sec-butylphenyl)aminocarbonyl]thiophene-3-sulfonamide | ~0.008** | 1.76** |

*results are generally the average of 2 to 5 experiments
**preliminary results

Other thiophenyl-, furyl- and pyrrole-sulfonamides provided herein include the following compounds: N-(4-chloro-3-methyl-5-isoxazolyl)- 2-(phenylaminocarbonyl)thiophene- 3-sulfonamide; N-(4-chloro-3-methyl-5-isoxazolyl)-5-benzylthiophene- 2-sulfonamide; N-(4-chloro-3-methyl-5-isoxazolyl)-3-benzylthiophene-2-sulfonamide; N-(4-chloro-3-methyl-5-isoxazolyl)-3-phenethylthiophene- 2-sulfonamide; N-(4-bromo-3-methyl-5-isoxazolyl)-3-styrylthiophene- 2-sulfonamide; N-(4-bromo-3-methyl-5-isoxazolyl)-2-styrylthiophene- 3-sulfonamide; N-(4-bromo-3-methyl-5-isoxazolyl)-2-phenoxythiophene- 3-sulfonamide; N-(4-bromo-3-methyl-5-isoxazolyl)-2-benzenesulfonylthiophene- 3-sulfonamide; N-(4-bromo-3-methyl-5-isoxazolyl)-2-phenylthiophene-3-sulfonamide; N-(4-bromo-3-methyl-5-isoxazolyl)-2-aminothiophene- 3-sulfonamide; N-(4-bromo-3-methyl-5-isoxazolyl)-2-(benzoylamino)thiophene- 3-sulfonamide; N-(4-bromo-3-methyl-5-isoxazolyl)-3-benzylthiophene-2-sulfonamide; N-(4-bromo-3-methyl-5-isoxazolyl)-3-phenethylthiophene- 2-sulfonamide; N-(4-bromo-3-methyl-5-isoxazolyl)-5-benzylthiophene- 2-sulfonamide; N-(4-bromo-3-methyl-5-isoxazolyl)-2-[(N-phenyl)methylaminocarbonyl]thiophene-3-sulfonamide; N-(4-bromo-3-methyl-5-isoxazolyl)- 5-benzylfuran-2-sulfonamide; N-(4-bromo-3-methyl-5-isoxazolyl)-5-(phenylthio)furan- 2-sulfonamide; N-(4-bromo-3-methyl-5-isoxazolyl)-5-(hydroxymethyl)furan- 2-sulfonamide; N-(4-bromo-3-methyl-5-isoxazolyl)-5-(carbomethoxy)furan-2-sulfonamide; N-(4-bromo-3-methyl-5-isoxazolyl)-2,5-dimethylfuran- 3-sulfonamide; N-(4-bromo-3-methyl-5-isoxazolyl)-5-(4-isopropylphenyl)thiophene- 2-sulfonamide; N-(4-bromo-3-methyl-5-isoxazolyl)-5-(4-propylphenyl)thiophene- 2-sulfonamide; N-(4-bromo-3-methyl-5-isoxazolyl)-3-(phenylaminocarbonyl)thiophene-2-sulfonamide; N-(4-bromo-3-methyl-5-isoxazolyl)- 2-benzylthiophene-3-sulfonamide; N-(4-bromo-3-methyl-5-isoxazolyl)-2-phenylthiophene- 3-sulfonamide; N-(4-bromo-3-methyl-5-isoxazolyl)-2-(dimethylaminocarbonyl)thiophene- 3-sulfonamide; N-(4-bromo-3-methyl-5-isoxazolyl)- 2-(di-isopropylaminocarbonyl)thiophene-3-sulfonamide; N-(4-bromo- 3-methyl-5-isoxazolyl)-2-(diethylaminocarbonyl)thiophene-3-sulfonamide; N-(4-bromo- 3-methyl-5-isoxazolyl)-5-(4-iso-butylphenyl)furan-2-sulfonamide; N-(4-bromo- 3-methyl-5-isoxazolyl)-5-styrylfuran-2-sulfonamide; and N-(4-bromo-3-methyl-5-isoxazolyl)-5-styrylthiophene-2-sulfonamide.

b. Ar² is a heterocycle with one heteroatom and two or more fused rings

Compounds in Ar² is a heterocycle with one heteroatom and two or more fused rings are provided. The heteroatom is O, S or N and Ar² is selected from among, but not limited to, quinolyl, isoquinolyl, dibenzofuryl, bibenzothiophenyl, and dibenzopyrrolyl compounds and other such groups. The fused rings may be substituted with one or more substituents selected from among substitutents set forth for $R^8$, $R^9$ and $R^{10}$ above, at any position. The sulfonamide portion of the compounds may be linked at any position.

(1) Ar² is quinolyl and isoquinolyl

Presently, preferred compounds are quinolines, particularly, 8-quinolinesulfonamides. The numbering scheme is as follows:

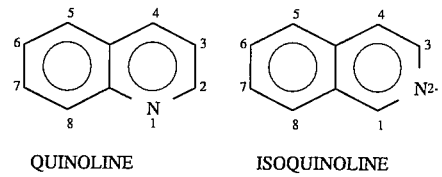

QUINOLINE    ISOQUINOLINE $R^1$ and $R^2$ are selected as described for the thiophenyl, furyl and pyrrolyl compounds, any of the rings may be substituted with one or more substituents selected from hydrogen or are selected as described above for $R^{26}$ and $R^{13}$, Exemplary quinolinesulfonamides are set forth in Table 7:

TABLE 7

| COMPOUND | $ET_A$ (μM) | $ET_B$ (μM) |
| --- | --- | --- |
| N-(3,4-dimethyl-5-isoxazolyl)-8-quinolinesulfonamide | 53 ± 7 | 63 ± 4 |
| N-(4-bromo-3-methyl-5-isoxazolyl)-8-quinolinesulfonamide | 0.12 ± 0.0 | 14 ± 1 |
| N-(4-bromo-5-methyl-3-isoxazolyl)-8-quinolinesulfonamide | 0.19 ± 0.04 | 12 ± 2 |
| N-(4-Benzyl-3-methyl-5-isoxazolyl)-8-quinolinesulfonamide | 39 ± 3 | 63 ± 10 |
| 8-ethoxy-N-(4-bromo-3-methyl-5-isoxazolyl)quinoline-5-sulfonamide | 1.7 ± 0.5 | 24 ± 0.3 |

(2) Ar² is dibenzofuryl, bibenzothiophenyl, and dibenzopyrrolyl

In certain embodiments Ar² is dibenzofuryl, bibenzothiophenyl, and dibenzopyrrolyl and has the following formula (XV):

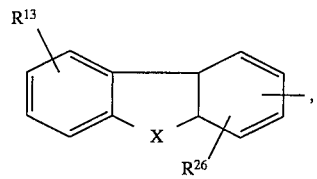

which is unsubstituted or substituted with one or more substituents selected from $R^{13}$ and $R^{26}$. In these embodiments, $R^1$ and $R^2$ are selected as described above for the thiophenyl, furyl and pyrrolyl compounds, These compounds are substituted as described above for the biphenyl compounds in which $R^{13}$ and R6; X is —CH=CH—, O, S, $NR^{11}$, in which $R^{11}$ is as set forth above (compounds in which X is —CH=CH— are phenanthrenesulfonamides, which are discussed above), and $R^{13}$ and $R^{26}$ are independently selected from H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, preferably from 1 to 6 atoms, and are either straight or branched chains or cyclic, and the aryl portions contain from about 4 to about 16 carbons, preferably 4 to 10 carbons.

In more preferred embodiments, $R^1$ is halide or methyl; $R^2$ is selected from lower alkyl, lower alkenyl, lower alkynl and lower haloalkyl; $R^{26}$ and $R^{13}$ are selected from H, lower alkyl, haloalkyl and halide. In more preferred embodiments $R^1$ is Cl, Br or $CH_3$; $R^2$ is selected from H, $CH_3$, $C_2H_5$, $CF_3$, n-$C_3H_7$, cyolo-$C_3H_7$ and $C_4H_8$; and $R^{26}$ and $R^{13}$ are each independently selected from H, halide, $NH_2$, $CF_3$ $CH_3$, CN, $CH_3$, $(CH_3)_3C$, $C_5H_{11}$, $CH_3O$, n-$C_4H_9O$ and $CH_2=CH$. In yet more preferred embodiments, $R^2$ is H, $CH_3$, $C_2H_5$, or $CF_3$; $R^{26}$ and $R^{13}$ are independently selected from H, $CH_3$, $C_2H_5$, $CF_3$, and halide; and X is O. Exemplary compounds include those set forth in Table 8:

above and may be 2-, 3- or 4-sulfonamides. $R^1$ and $R^2$ are selected as described above for the thiphenyl, furyl and pyrrolyl compounds.

Compounds in which $Ar^2$ is a pyridyl group include, but are limited to, N-(4-bromo-3-methyl-5-isoxazolyl)pyridine-2-sulfonamide, N-(4-bromo-5-methyl-3-isoxazolyl)pyridine- 2-sulfonamide, N-(3,4-dimethyl-5-isoxazolyl)pyridine-2-sulfonamide, N-(4,5-dimethyl-3-isoxazolyl)pyridine-2-sulfonamide, 3-methoxycarbonyl-N-(4-bromo-5-methyl-3-isoxazolyl)pyridine-2-sulfonamide and 3-methoxycarbonyl-N-(4-bromo-5-methyl-3-isoxazolyl)pyridine-2-sulfonamide, N-(3,4-dimethyl-5-isoxazolyl)-3-(N-phenylaminocarbonyl)pyridine-2-sulfonamide, N-(4-bromo-5-methyl-3-isoxazolyl)-3-(N-phenylaminocarbonyl)pyridine-2-sulfonamide, and N-(4-bromo-3-methyl-5-isoxazolyl)-3-(N-phenylaminocarbonyl)pyridine- 2-sulfonamide. These compounds appear to be $ET_A$ selective with $IC_{50}$ concentrations on the order of 1–3 µM or less.

d. $Ar^2$ is a heterocycle with two or more heteroatoms

Compounds in which $Ar^2$ is a heterocycle that contains two or more heteroatoms selected from O, S, N, and $NR^{11}$, including, but are not limited to pyrimidinyl, purinyl, imi-

TABLE 8

| COMPOUND | $ET_A$ (µM)* | $ET_B$ (µM)* |
|---|---|---|
| N-(4-bromo-3-methyl-5-isoxazolyl)dibenzofuran-4-sulfonamide | **0.39 | **10 |
| N-(3,4-dimethyl-5-isoxazolyl)-2-dibenzofuransulfonamide | — | — |
| N-(3,4-Dimethyl-5-isoxazolyl)-3-dibenzofuransulfonamide | 6.1 ± 1.2 | 0.81 ± 0.13 |
| N-(4-bromo-3-methyl-5-isoxazolyl)-3-dibenzofuransulfonamide | 1.05 ± 0.05 | 0.23 ± 0.05 |
| N-(3,4-dimethyl-5-isoxazolyl)dibenzothiophene-4-sulfonamide | 0.37 ± 0.06 | 1.8 ± 0.4 |
| N-(4-bromo-3-methyl-5-isoxazolyl)dibenzothiophene-4-sulfonamide | 0.115 ± 0.02 | 0.47 ± 0.13 |

*results based on 1 to 4 experiments c. $Ar^2$ is a six-membered heterocycle with one heteroatom selected from S, O or $NR^{11}$ Prefered six-membered heterocylic rings are pyridyl rings. The pyridyl groups may be substituted with one or more substituents selected from $R^{13}$, $R^8$ and $R^{26}$, as defined dazolyl, oxazolyl, thiazolyl, pyrazolyl, benzofuryl, benzothiophenyl and benzopyrrolyl, are provided. These compounds may be unsubstituted or substituted with one or more substitutents selected from those set forth for $R^3$ $R^8$ or $R^{26}$, Particular compounds that have been synthesized, include:

TABLE 9

| COMPOUND | $ET_A$ (µM)* | $ET_B$ (µM)* |
|---|---|---|
| 5-acetamido-4-methyl-N-(3,4-dimethyl-5-isoxazolyl)thiazole-2-sulfonamide | ~59 | 36 ± 6 |
| 5-acetamido-4-methyl-N-(4-bromo-3-methyl-5-isoxazolyl)thiazole-2-sulfonamide | 6.7 | 14 ± 2 |
| N-(3,4-dimethyl-5-isoxazolyl)thiazole-2-sulfonamide | | |
| N-(4-bromo-3-methyl-5-isoxazolyl)thiazole-2-sulfonamide | | |
| N-(4-chloro-3-methyl-5-isoxazolyl)thiazole-2-sulfonamide | | |
| N-(3,4-dimethyl-5-isoxazolyl)-4-benzofuransulfonamide | 1.4 ± 0.3 | — |
| N-(3,4-Dimethyl-5-isoxazolyl)benzo-2,1,3-thiadiazole-4-sulfonamide | 0.37 ± 0.03 | — |
| N-(4-Bromo-3-methyl-5-isoxazolyl)benzo-O 2,1,3-thiadiazole-4-sulfonamide | 0.073 ± 0.048 | 36 ± 20 |
| 5-chloro-1,3-dimethy-N-(4-chloro-3-methyl-5-isoxazolyl)pyrazole-4-sulfonamide | 0.19 ± 0.03 | 26 ± 2 |
| 5-chloro-1,3-dimethy-N-(4-bromo-3-methyl-5-isoxazolyl)pyrazole-4-sulfonamide | 0.15 ± 0.03 | 22 ± 2 |

TABLE 9-continued

| COMPOUND | $ET_A$ (μM)* | $ET_B$ (μM)* |
|---|---|---|
| 3,5-dimethyl-N-(4-bromo-3-methyl-5-isoxazolyl)isoxazole-4-sulfonamide | 5.35 ± 0.05 | 78 ± 2 |

*results based on 1 to 4 experiments

3. Compounds in which $Ar^2$ is alkyl

Compounds in which $Ar^2$ is alkyl include compounds in which $Ar^2$ is $CH_3-(CH_2)_n$, where n is 0 to about 30, preferably, 0 to 20, and more preferably between about 5 and about 10 and which may be substituted with halide, amino, carbonyl, nitro, and the like, and compounds in which $Ar^2$ is

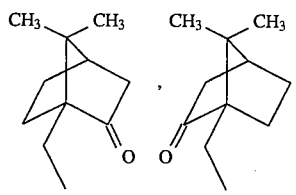

or isomers or substituted derivatives thereof.

$R^1$ and $R^2$ are selected as described above for the thiophenyl, furyl and pyrrolyl compounds. The methyl groups may be replaced by other lower alkyl groups, hydrogen or halide.

Selected compounds have the following activities:

TABLE 10

| COMPOUND | $ET_A$ (μM) | $ET_B$ (μM) |
|---|---|---|
| N-(3,4-dimethyl-5-isoxazolyl)-(−)-10-camphorsulfonamide | 11.9 ± 0.4 | ~100 |
| N-(3,4-Dimethyl-5-isoxazolyl)methanesulfonamide | 57* | 21* |
| N-(3,4-Dimethyl-5-isoxazolyl)-(+)-10-camphorsulfonamide | 20 ± 2.5 | 48.2 ± 3.6 |
| N-(4-Tridecyl-3-trifluoromethyl-5-isoxazolyl)methane sulfonamide | 17.1 ± 1.0 | 5.8 ± 2.0 |
| N-(3,4-dimethyl-5-isoxazolyl)octyl-1-sulfonamide | 3.74 | 2.88 |

*preliminary results

4. Compounds in which $Ar^2$ is styryl

Compounds in which $Ar^2$ is styryl are provided. These compounds have formulae (XVI):

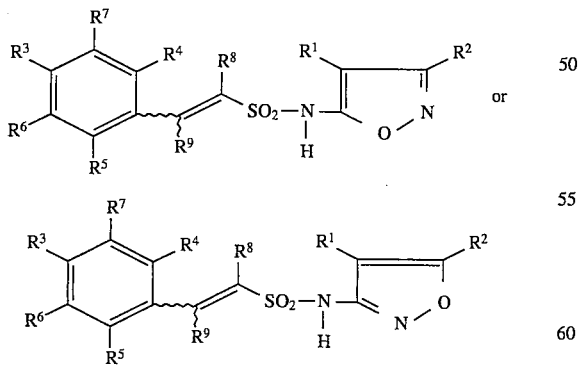

in which $R^1$ and $R^2$ are selected as described above for the thiophenyl, furyl and pyrrolyl compounds and; $R^1-R^9$ are as defined above, $R^8$ and $R^9$ may be cis or trans position. Compounds in which $Ar^2$ is styryl include, but are not limited to: N-(3,4-dimethyl-5-isoxazolyl)-β-trans-styrenesulfonamide, N-(4-bromo-3-methyl-5-isoxazolyl)-β-trans-styrenesulfonamide, N-(4-bromo-5-methyl-3-isoxazolyl)-β-trans-styrenesulfonamide, 2-nitro-N-(3,4-dimethyl-5-isoxazolyl)styrenesulfonamide, 2-nitro-N-(4-bromo-3-methyl-5-isoxazolyl)styrenesulfonamide, 2-nitro-N-(4-bromo-5-methyl-3-isoxazolyl)styrenesulfonamide, 1,2-trans-dimethyl-N-(3,4-dimethyl-5-isoxazolyl)styrene-1-sulfonamide, 1,2-trans-dimethyl-N-(4-bromo-3-methyl-5-isoxazolyl)styrene-1-sulfonamide, 1,2-trans-dimethyl-N-(4-bromo-5-methyl-3-isoxazolyl)styrene-1-sulfonamide, N-(3,4-dimethyl-5-isoxazolyl)-2-phenylstyrene-1-sulfonamide, N-(4-bromo-5-methyl-3-isoxazolyl)-2-phenylstyrene-1-sulfonamide, N-(4-bromo-3-methyl-5-isoxazolyl)-2-phenylstyrene-1-sulfonamide, 1,2-cis-dimethyl-N-(3,4-dimethyl-5-isoxazolyl)styrene-1-sulfonamide, 1,2-cis-dimethyl-N-(4-bromo-3-methyl-5-isoxazolyl)styrene-1-sulfonamide and 1,2-cis-dimethyl-N-(4-bromo-5-methyl-3-isoxazolyl)styrene-1-sulfonamide. The activities of exemplary compounds are set forth in Table 11.

TABLE 11

| COMPOUND | $ET_A$ (µM)* | $ET_B$ (µM)* |
| --- | --- | --- |
| N-(3,4-dimethyl-5-isoxazolyl)-β-trans-styrene-sulfonamide | 12 | 21 |
| 2-nitro-(N-(3,4-dimethyl-5-isoxazolyl)-β-trans-styrene-sulfonamide | 15 | 61.5 |
| 1,2-cis-dimethyl-N-(3,4-dimethyl-5-isoxazolyl)styrene-1-sulfonamide | 35 | 37 |
| 1,2-trans-dimethyl-N-(3,4-dimethyl-5-isoxazolyl)styrene-1-sulfonamide | 9 | — |
| N-(3,4-dimethyl-5-isoxazolyl)-2-phenylstyrene-1-sulfonamide | 4 | ~50 |

*preliminary results

B. Preparation of the Compounds

The preparation of the above compounds are described in detail in the examples. Any such compound or similar compound may be synthesized according to a method discussed in general below and set forth in the Examples by selecting appropriate starting materials as exemplified.

In general, most of the syntheses involve the condensation of a sulfonyl chloride with an aminoisoxazole in dry pryidine or in tetrahydrofuran (THF) and sodium hydride. The sulfonyl chorides and aminoisoxazoles either can be obtained commercially or synthesized according to methods described in the Examples or using other methods available to those of skill in this art (see, e.g., U.S. Pat. Nos. 4,659,369, 4,861,366 and 4,753,672). Exemplary preparations of numerous compounds provided herein are set forth in the Examples.

The N-(alkylisoxazolyl)sulfonamides can be prepared by condensing an aminoisoxazole with a sulfonyl chloride in dry pyridine with or without the catalyst 4-(dimethylamino)pyridine. The N-(3,4-dimethyl-5-isoxazolyl)sulfonamides and N-(4,5-dimethyl-5-isoxazolyl)sulfonamides can be prepared from the corresponding aminodimethylisoxazole, such as 5-amino-3,4-dimethylisoxazole. The N-(3,4-dimethyl-5-isoxazolyl)sulfonamides and the N-( 4,5-dimethyl-3-isoxazolylsulfonamdies can be prepared from the corresponding aminodimethylisoxaole, such as 5-amino-3,4-dimethylisoxazole. For example, N-(3,4-dimethyl-5-isoxazolyl)-2-(carbomethoxy)thiophene-3-sulfonamide was prepared from 2-methoxycarbonylthiophene-3-sulfonyl chloride and 5-amino-3,4-dimethylisoxazole in dry pyridine.

The N-(4-haloisoxazolyl)sulfonamides can be prepared by condensation of amino-4-haloisoxazole with a sulfonyl chloride in THF with sodium hydride as a base. For example, N-(4-bromo-3-methyl-5-isoxazolyl)thiophene-2-sulfonamide was prepared from 5-amino-4-bromo-3-methylisoxazole and thiophene-2-sulfonyl chloride in THF and sodium hydride. N-(4-bromo-3-methyl-5-isoxazolyl)- 5-(3-isoxazolyl)thiophene-2-sulfonamide was prepared from 5-amino-4-bromo-3-methylisoxazole and 5-(3-isoxazolyl)thiophene-2-sulphonyl chloride.

Prodrugs and other derivatives of the compounds suitable for administration to humans may also be designed and prepared by methods known to those of skill in the art (see, e.g., Nogrady (1985) *Medicinal Chemistry A Biochemical Approach*, Oxford University Press, New York, pages 388–392).

Compounds listed and described have been synthesized and tested for activity in in vitro assays and, in some cases, in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

2. Preparation of isoxazolylsulfonamides in which $Ar^2$ is phenyl, biphenyl and a fused aromatic ring a. Preparation of the N-isoxazolylsulfonamides in which $Ar^2$ is phenyl and biphenyl and n=0

(1) $Ar^2$ is phenyl

The compounds, such as 4-nitro-N-(3,4-dimethyl-5-isoxazolyl)benzenesulfonamide, for use in the methods herein may be prepared by reacting a sulfonyl chloride with 5-amino-3,4-dimethylisoxazole in pyridine solution with 4-(dimethylamino)pyridine as a catalyst. Following the reaction, the pyridine is removed under reduced pressure and the residue is partitioned between water and ethyl acetate. The organic layer is washed and then dried over anhydrous magnesium sulfate, the solvents are evaporated and the residue is purified by column chromatography over silica gel (e..q., 1% methanol in chloroform as eluent) to yielded a solid. Further purification is achieved by recrystallization from ethyl acetate/hexanes, to yield the pure product. In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

Compounds such as, 3-amino-N-(3,4-dimethyl-5-isoxazolyl)benzenesulfonamide and 2-amino-N-(3,4-dimethyl-5-isoxazolyl)benzenesulfonamide, can be prepared by hydrogenation of corresponding nitro-N-(3,4-dimethyl-5-isoxazolyl)benzenesulfonamide, which is prepared as described above.

Alternatively, the benzenesulfonamides can be prepared from the corresponding sulfonyl chloride and the aminoisoxazole in tetrahydrofuran solution containing sodium hyride.

(2) $Ar^2$ is biphenyl, dibenzofuryl, dibenzothiophenyl, and dibenzopyrrolyl

The compounds, such as N-(3,4-dimethyl-5-isoxazolyl) biphenylsulfonamide (seee, e.g., EXAMPLE 89), can be prepared from 4-biphenylsulfonyl chloride and an amino-substituted isoxazole, such as 5-amino- 3,4-dimethylisoxazole, in dry pyridine. Following the reaction, the pyridine is removed under reduced pressure and the residue is partitioned between water and ethyl acetate. The organic layer is washed and then dried over anhydrous magnesium sulfate, the solvents are evaporated and the residue is purified by column chromatography over silica gel (e.g., 1% methanol in chloroform as eluent) to yielded a solid. Further purification is achieved by recrystallization from ethyl acetate/ hexanes or column chromatography, to yield the pure product.

In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

Alternatively, the sulfonamides can be prepared from the corresponding aminoisoxazole in tetrahydrofuran solution containing sodium hydride (see, e.g., EXAMPLE 90).

b. Preparation of compounds in which $Ar^2$ is phenyl and biphenyl and n is > 0

Compounds, such as N-(3,4-dimethyl-5-isoxazolyl)-α-toluenesulfonamide can be prepared as described in B above using appropriate starting materials, such as 1 from α-toluenesulfonyl chloride and 5-amino-3,4-dimethylisoxazole.

c. Preparation of N-isoxazolylsulfonamides in which $Ar^2$ is a fused aromatic ring (1) $Ar^2$ is naphthyl Compounds, such as N-(4-bromo-5-methyl-3-isoxazolyl)-1-naphthalenesulfonamide and 5-dimethylamino-N-(4-bromo-3-methyl-5-isoxazolyl)-1-naphthalenesulfonamide can be prepared as described in B(1)a above using appropriate starting materials, such as 3-amino-4-bromo-5-methylisoxazole and 1-naphthalenesulfonyl chloride, and 5-amino-4-bromo-3-methylisoxazole and 5-dimethylaminonaphthalenesulfonyl chloride, respectively (see, e.g., EXAMPLES 51, 118 and 119)

(2) phenanthryl and anthracenyl

Compounds, such as N-(4-bromo-3-methyl-5-isoxazolyl)-9,10-dioxo-anthracene- 2-sulfonamide, N-(4-bromo-3-methyl-5-isoxazolyl)-3-phenanthrenesulfonamide, N-(3,4-dimethyl-5-isoxazolyl)-3-Phenanthrenesulfonamide can be prepared as described in B above from appropriate aminoisoxazoles and sulfonyl chlorides.

2. Preparation of N-isoxazolylsulfonamides in which $Ar^2$ is contains a heterocyclic ring or fused rings a. $Ar^2$ is thiophenyl, furyl and pyrrolyl The compounds in which $Ar^2$ is thiophenyl, furyl and pyrrolyl herein may be prepared by reacting an appropriate sulfonyl chloride with a 5-aminoisoxazole substituted at the 3 and 4 positions, such as 5-amino-4-bromo-3-methylisoxazole, in tetrahydrofuran (THF) solution containing a base, such as sodium hydride. Following the reaction, the THF is removed under reduced pressure, the residue dissolved in water, acidified and extracted with methylene chloride. The organic layer is washed and then dried over anhydrous magnesium sulfate, the solvents are evaporated and the residue is purified by recrystallization using hexanes/ethylacetate to yield pure product.

Alternatively, these sulfonamides can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature. For example:

(1) N-(4-Bromo-3-methyl-5-isoxazolyl)- 2-(N-phenyl-amioncarbonyl)thiophene- 3-sulfonamide was prepared from N-(4-bromo-3-methyl- 5-isoxazolyl)-2-carboxythiophene-3-sulfonamide and aniline and 1-ethyl- 3'[3-dimethylaminopropyl]carbodiimide (EDCI). N-(4-Bromo-3-methyl- 5-isoxazolyl)-2-[(4-methoxyphenyl)aminocarbonyl]thiophene-3-sulfonamide was prepared from 4-methoxyaniline, N,N'-diisopropylethylamine and N-(4-bromo- 3-methyl- 5-isoxazolyl)-2-carboxylthiophene-3-sulfonamide. N-(4-Bromo-3-methyl-5-isoxazolyl)-2-(benzylaminocarbonyl)thiophene-3-sulfonamide was prepared from N-(4-bromo-3-methyl-5-isoxazolyl)-2-carboxylthiophene-3-sulfonamide and benzylamine as described above.

N-(4-bromo-3-methyl-5-isoxazolyl)-2-carboxylthiophene-3-sulfonamide was prepared from N-(4-bromo-3-methyl-5-isoxazolyl)-2-(carbomethoxy)thio-phene- 3-sulfonamide, which was prepared from the condensation of 5-amino-4-bromo- 3-methylisoxazole and 2-(carbomethoxy)thiophene-3-sulfonyl chloride.

(2) N-(4-Bromo-3-methyl-5-isoxazolyl)-1-(4'-isopropylphenyl)pyrrole- 2-sulfonamide and N-(4-bromo-3-methyl-5-isoxazolyl)-1-(4'-isopropylphenyl)pyrrole- 3-sulfonamide were prepared from 5-amino-4-bromo-3-methylisoxazole and a mixture of 1-(4'-isopropylphenyl)pyrrole-2-sulfonyl chloride and 1-(4'-isopropylphenyl)pyrrole-3-sulfonyl chloride. These sulfonyl chlorides were prepared from 1-(4'-isopropylphenyl)pyrrole-2-sulfonic acid in phosphorus oxychloride and phosphorus pentachloride. 1-(4'-isopropylphenyl)pyrrole- 2-sulfonic acid was prepared from 1-(4'-isopropylphenyl)pyrrole and chlorosulfonic acid. 1-(4'-isopropylphenyl)pyrrole was prepared from 4-isopropylaniline and 2,5-dimethoxytetrahydrofuran.

b. $Ar^2$ is a heterocycle with one heteroatom and two or more fused rings

These compounds can be prepared as described in B(1)a above. For example, N-(4-bromo-3-methyl-5-isoxazolyl)-8-quinolinesulfonamide can prepared from 5-amino-4-bromo-3-methylisoxazole and 8-quinolinesulfonyl chloride in a suspension of sodium hydride in dry THF (see, e.g., Examples 99 and 100).

c. $Ar^2$ is a six-membered heterocycle with one heteroatom selected from S, O, N or NR11

These compounds can be prepared as described in B above. For example, compounds, such a N-(3,4-dimethyl-5-isoxazolyl)-2-dibenzofuransulfonamide can be prepared by reacting 5-amino-3,4-dimethylisoxazole and 2-dibenzofuransulfonyl chloride in dry pyridine (see, e.g., EXAMPLE 93).

d. $Ar^2$ is a heterocycle with two or more heteroatoms

These compounds can also be prepared according to the methods set forth in B(1)a above. For example, N-(4-bromo-3-methyl-5-isoxazolyl)benzo- 2,1,3-thiadiazole-4-sulfonamide can be prepared by reacting 5-amino-4-bromo-3-methylisoxazole and benzo-2,1,3-thiadiazole-4-sulfonyl chloride in a suspension of sodium hydride in dry THF.

3. Preparation of compounds in which $Ar^2$ is alkyl

These compounds can also be prepared according the the methods set forth in B(1)a above (see, e.g., Examples 101 and 102).

4. Preparation of compounds in which $Ar^2$ is styryl

These compounds can also be prepared according the the methods set forth in B(1)a above. For example, 2-nitro-N-(3,4-dimethyl- 5-isoxazolyl)-β-trans-styrenesulfonamide can be prepared from 2-nitro-trans-β-styrenesulfonyl chloride [see, e.g., Bordwell et al. (1946) *J. Am. Chem. Soc.* 68:1778 for a process for nitrogenation of styrenesulfonyl chloride] and 5-amino-3,4-dimethylisoxazole.

C. Evaluation of the bioactivity of the compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those of specifically identified herein, that are endothelin antagonists or agonists may be identified using such screening assays.

1. Identifying compounds that modulate the activity of an endothelin peptide The compounds are tested..for the ability to modulate the activity of endothelin-1. Numerous assays are known to those of skill in the art for evaluating the ability of compounds to modulate the activity of endothelin (see, e.g., U.S. Pat. No. 5,114,918 to Ishikawa et al.; EP A10 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177:171–176). In vitro studies may be corroborated with in vivo studies (see, e.g., U.S. Pat. No. 5,114,918 to Ishikawa et al.; EP A10 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., Tissue selectivity of endothelin, *Eur. J. Pharmacol* 165:223–230, (1989)). The ability to act as an endothelin antagonist in vivo can be tested in hypertensive rats, spontaneously hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A10 436 189 to BANYU PHARMACEUTICAL CO., LTD (Oct. 7, 1991 ); see, also Bolger et al. (1983) *J. Pharmacol. Exp. Ther.* 225291–309; Stein et al. (1994) *J. Med. Chem.* 37:329–331; and Clozel et al. (1993) *Nature* 365:759–761). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi. et al. (1991) *Reg. Pep.* 32: 23–37, Panek et al. (1992) *Biochem. Biophys. Res. Commun.* 183:566–571). For example, $ET_B$ receptors are expressed in vascular endothelial cells, possibly mediating the release of prostacyclin and endotheliumderived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res, Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. No. 5,248,807; U.S. Pat. No. 5,240,910; U.S. Pat. No. 5,198,548; U.S. Pat. No. 5,187,195; U.S. Pat. No. 5,082,838; U.S. Pat. No. 5,230,999; published Canadian Application Nos. 2,067,288 and 2,071, 193; published Great Britain Application No. 2,259,450; Published International PCT Application No. WO 93/08799; Benigi et al. (1993) *Kidney International* 44:440–444; Nirei et al. (1993) *Life Sciences* 52:1869–1874; Stein et al. (1994) *J. Med. Chem.* 37:329–331; and Clozel et al. (1993) *Nature* 365:759–761). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of endothelin receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126:3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptors subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and administration of the compositions

Effective concentrations of one or more of the sulfonamide compounds of formula I or II or pharmaceutically acceptable salts, esters or other derivatives thereof are mixed with a suitable pharmaceutical carrier or vehicle.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as salts of the compounds or prodrugs of the compounds may also be used in formulating effective pharmaceutical compositions.

The concentrations or the compounds are effective for delivery of an amount, upon administration, that ameliorates the symptoms of the endothelinmediated disease. Typically, the compositions are formulated for single dosage administration.

Upon mixing or addition of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients.

The active compounds can be administered by any appropriate route, for example, orally, parenterally, intravenously, intradermally, subcutaneously, or topically, in liquid, semiliquid or solid form and are formulated in a manner suitable for each route of administration. Preferred modes of administration include oral and parenteral modes of administration.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A10 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound in the drug composition will depend on absorption, inactivation and excretion rates of the active compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 ng/ml to about 50–100 μg/ml. The pharmaceutical compositions typically should provide a dosage of from about 0.01 mg to about 2000 mg of compound per kilogram of body weight per day. The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules or troches. Pharmaceutically compatible binding agents and adjuvant materials can be included as part of the composition.

The tablets, pills, capsules, troches and the like can contain any of the following ingredients, or compounds of a similar nature: a binder, such as microcrystalline cellulose, gum tragacanth and gelatin; an excipient such as starch and lactose, a disintegrating agent such as, but not limited to, alginic acid and corn starch; a lubricant such as, but not limited to, magnesium stearate; a glidant, such as, but not limited to, colloidal silicon dioxide; a sweetening agent such as sucrose or saccharin; and a flavoring agent such as peppermint, methyl salicylate, and fruit flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parental preparations can be enclosed in ampules, disposable syringes or multiple dose vials made of glass, plastic or other suitable material.

If administered intravenously, suitable carriers include physiological saline or phosphate buffered saline (PBS), and solutions containing thickening and solubilizing agents, such as glucose, polyethylene glycol, and polypropylene glycol and mixtures thereof. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compounds may be prepared with carriers that protect the compound against rapid elimination from the body, such as time release formulations or coatings. Such carriers include controlled release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of such formulations are known to those skilled in the art.

The compounds may be formulated for local or topical application, such as for topical application to the skin and mucous membranes, such as in the eye, in the form of gels, creams, and lotions and for application to the eye or for intracisternal or intraspinal application. Such solutions, particularly those intended for ophthalmic use, may be formulated as 0.01%–10% isotonic solutions, pH about 5–7, with appropriate salts. The compounds may be formulated as aeorsols for topical application, such as by inhalation (see, e.g., U.S. Pat. Nos. 4,044,126, 4,414,209, and 4,364,923, which describe aerosols for delivery of asteroid useful for treatment inflammatory diseases, particularly asthma).

Finally, the compounds may be packaged as articles of manufacture containing packaging material, a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 μM, within the packaging material, and a label that indicates that the compound or salt thereof is used for antagonizing the effects of endothelin, treating endothelin-mediated disorders or inhibiting the binding of an endothelin peptide to an ET receptor.

The following examples are included for illustrative purposes only and are not intended to limit the scope of the invention.

EXAMPLE 1

N-(4-Bromo-3-methyl-5-isoxazolyl)thiophene-2-sulfonamide

A solution of 5-amino-4-bromo-3-methylisoxazole (177 mg, 1.0 mmol) in dry tetrahydrofuran (THF, 2 ml) was added to a suspension of sodium hydride (60% dispersion in mineral oil, 90 mg, 2.2 mmol) in dry THF (1 ml) at 0°–5° C. After stirring at 0°–5° C. for 5 min., the reaction was stirred at room temperature for 10 min to complete the reaction. The reaction mixture was re-cooled to 0° C. and thiophene-2-sulfonyl chloride (200 mg, 1.1 mmol) dissolved in dry THF (2 ml) was added dropwise. Stirring was continued for 1 h; during this period the reaction mixture was slowly attained the ambient temperature. THF was removed under reduced pressure. The residue was dissolved in water (10 ml), the pH was adjusted to 10–11 by adding 5N sodium hydroxide solution, and was extracted with ethyl acetate (3×10 ml) to remove the neutral impurities. The aqueous layer was acidified with concentrated HCl(pH 2–3) and extracted with methylene chloride (3×10 ml). The combined organic layers was dried over anhydrous magnesium sulfate and concentrated under reduced pressure to give N-(4-bromo-3-methyl- 5-isoxazolyl)thiophene-2-sulfonamide. The pure material was obtained by recrystallization using hexanes/ethyl acetate (110 mg, 34 % yield), m.p. 125°–127° C.

EXAMPLE 2

N-(4-Bromo-3-methyl-5-isoxazolyl)-5-(3-isoxazolyl)thiophene-2-sulfonamide

A solution of 5-amino-4-bromo-3-methylisoxazole (177 mg, 1.0 mmol) in dry THF (2 ml) was added to a suspension of sodium hydride (60% dispersion in mineral oil, 90 mg, 2.2 mmol) in dry THF (1 ml) at 0°–5° C. After stirring at 0°–5° C. for 5 min, the reaction was warmed to room temperature for 10 min to complete the reaction. The reaction mixture was re-cooled to 0° C., and 5-( 3-isoxazolyl)thiophene- 2-sulphonyl chloride (273 mg, 1.1 mmol), which had been dissolved in dry THF (2 ml), was added slowly. Stirring was continued for 1 h; during this period the reaction mixture slowly attained ambient temperature. THF was removed under reduced pressure. The residue was dissolved in water (10 ml), the pH was adjusted to 2–3 by adding concentrated HCl, and was extracted with methylene chloride (3×10 ml). The combined organic layers was dried over anhydrous magnesium sulfate and concentrated under reduced pressure to give N-(4-bromo-3-methyl-5-isoxazolyl)- 5-(3-isoxazolyl)thiophene-2-sulfonamide. The pure material was obtained by recrystallization using hexanes/ethyl acetate (160 mg, 41% yield), m.p. 120°–123° C.

EXAMPLE 3

N-(4-Bromo-3-methyl-5-isoxazolyl)-5-(2-pyridyl)thiophene-2-sulfonamide

N-(4-Bromo-3-methyl-5-isoxazolyl)-5-(2-pyridyl)thiophene-2-sulfonamide was prepared in the same manner as described in Example 2 from 5-amino-4- bromo- 3-methylisoxazole and 5-(2-pyridyl)thiophene-2-sulphonyl chloride in 40% yield. Purification was achieved by recrystallization from ethyl acetate to give a crystalline solid, m.p. 186°–188° C.

EXAMPLE 4

N-(4-Bromo-3-methyl-5-isoxazolyl)-4,5-dibromothiophene-2-sulfonamide

N-(4-Bromo-3-methyl-5-isoxazolyl)-4, 5-dibromothiophene-2-sulfonamide was prepared in the same manner as described in Example 2 from 5-amino-4-bromo-3-methylisoxazole and 4,5-dibromothiophene-2-sulphonyl chloride in 45% yield. Purification was achieved by recrystallization from ethyl acetate/hexanes to give a crystalline solid, m.p. 153°–155° C.

EXAMPLE 5

N-(4-Bromo-3-methyl-5-isoxazolyl)-5-chloro-3-methylbenzo[b]thiophene-2-sulfonamide N-(4-Bromo-3-methyl-5-isoxazolyl)-5-chloro-3-methylbenzo[b]thiophene-2-sulfonamide was prepared in the same manner as described in Example 2 from 5-amino-4-bromo-3-methylisoxazole and 5-chloro-3-methylbenzo[b]thiophene-2-sulphonyl chloride in 18% yield. Purification was achieved by recrystallization from ethyl acetate/hexanes to give a crystalline solid, m.p. 153°–155° C.

EXAMPLE 6

N-(4-Bromo-3-methyl-5-isoxazolyl)-5-(4-chlorobenzamidomethyl)thiophene-2-sulfonamide N-(4-Bromo-3-methyl-5-isoxazolyl)-5-(4-chlorobenzamidomethyl)thiophene- 2-sulfonamide was prepared in the same manner as described in Example 2 from 5-amino-4-bromo-3-methylisoxazole and 5-(4-chloro-benzamidomethyl)thiophene- 2-sulphonyl chloride in 27% yield. The crude product was passed through a silica gel column using hexanes/ethyl acetate as eluent. Purification was effected by recrystallization from ethyl acetate/hexanes to give a crystalline solid, m.p. 210° C. (dec).

EXAMPLE 7

N-(4-Bromo-3-methyl-5-isoxazolyl)-4-(benzenesulfonyl)thiophene-2-sulfonamide

N-(4-Bromo-3-methyl-5-isoxazolyl)-4-(benzenesulfonyl)thiophene-2-sulfonamide was prepared in the same manner as described in Example 2 from 5-amino-4-bromo-3-methylisoxazole and 4-benzenesulfonylthiophene-2-sulphonyl chloride in 26% yield. Purification was achieved by recrystallization from ethyl acetate/hexanes to give a crystalline solid, m.p. 181°–184° C.

EXAMPLE 8

N-(4-Bromo-3-methyl-5-isoxazolyl)-4-bromo-5-chloro-thiophene-2-sulfonamide

N-(4-Bromo-3-methyl-5-isoxazolyl)-4-bromo-5-chloro-thiophene-2-sulfonamide was prepared in the same manner as described in Example 2 from 5-amino-4-bromo-3-methylisoxazole and 4-bromo- 5-chlorothiophene-2-sulphonyl chloride in 25% yield. Purification was achieved by recrystallization from ethyl acetate/hexanes to give a crystalline solid, m.p. 143°–145° C.

EXAMPLE 9

N-(4-Bromo-3-methyl-5-isoxazolyl)-2,5-dichlorothiophene-3-sulfonamide

N-(4-Bromo-3-methyl-5-isoxazolyl)-2,5-dichlorothiophene-3-sulfonamide was prepared in the same manner as described in Example 2 from 5-amino-4-bromo-3-methylisoxazole and 2,5-dichlorolthiophene-3-sulphonyl chloride in 47% yield. Purification was achieved by recrystallization from ethyl acetate/hexanes to give a crystalline solid, m.p. 135°–138° C.

EXAMPLE 10

N-(4-Bromo-3-methyl-5-isoxazolyl)-2,5-dimethylthiophene-3-sulfonamide

N-(4-Bromo-3-methyl-5-isoxazolyl)-2,5-dimethylthiophene-3-sulfonamide was prepared in the same manner as described in Example 1 from 5-amino-4-bromo- 3-methylisoxazole and 2,5-dimethylthiophene-3-sulphonyl chloride in 55% yield. Purification was achieved by recrystallization from ethyl acetate/hexanes to give a crystalline solid, m.p. 77°–80° C.

EXAMPLE 11

N-(4-Bromo-3-methyl-5-isoxazolyl)-4,5-dichlorothiophene-2-sulfonamide

N-(4-Bromo-3-methyl-5-isoxazolyl)-4, 5-dichlorothiophene-2-sulfonamide was prepared in the same manner as described in Example 1 from 5-amino-4-bromo-3-methylisoxazole and 4,5-dichlorothiophene-2-sulphonyl chloride in 42% yield. Purification was achieved by recrystallization from ethyl acetate/hexanes to give a crystalline solid, m.p. 135°–138° C.

EXAMPLE 12

N-(4-Bromo-3-methyl-5-isoxazolyl )-2,5-di chloro-4-bromothiophene-3-sulfonamide N-(4-Bromo-3-methyl-5-isoxazolyl)-2,5-dichloro-4-bromothiophene-3-sulfonamide was prepared in the same manner as described in Example 1 from 5-amino-4-bromo-3-methylisoxazole and 4-bromo-2,5-dichlorothiophene-3-sulfonyl chloride in 58% yield. Purification was achieved by recrystallization from ethyl acetate/hexanes to give a crystalline solid, m.p. 146°–149° C.

EXAMPLE 13

N-(4-Bromo-3-methyl-5-isoxazolyl)-2-{3-[1-methyl-5-(trifluoromethyl)pyrazolyl]} thiophene-5-sulfonamide N-(4-Bromo-3-methyl-5-isoxazolyl)-2-{3-[1-methyl-5-(trifluoromethyl)pyrazolyl]}thiophene- 5-sulfonamide was prepared in the same manner as described in Example 1 from 5-amino-4-bromo-3-methylisoxazole and 2-{3-[1-methyl-5-(trifluoromethyl)pyrazolyl]}thiophene- 5-sulphonyl chloride in 30% yield. Purification was achieved by recrystallization from ethyl acetate/hexanes to give a crystalline solid, m.p. 121°–123° C.

EXAMPLE 14

N-(4-Bromo-5-methyl-3-isoxazolyl)thiophene-2-sulfonamide

Thiophene-2-sulphonyl chloride (183 mg, 1 mmol) was added to a solution of 3-amino-4-bromo-5-methylisoxazole (177 mg, 1 mmol) in dry pyridine (0.5 ml). The reaction mixture was stirred at room temperature for 3 h. Pyridine was removed under reduced pressure and the residue was partitioned between water and ethyl acetate. The organic layer was washed with 1N HCl (3×10 ml), brine (10 ml) and dried over anhydrous magnesium sulfate. Evaporation of the solvents left an oily residue which was solidified at –20° C. and then purified by recrystallization from ethyl acetate/hexanes, to give the pure product (51% yield) as a tan solid, m.p. 156°–158° C.

EXAMPLE 15

N-(4-Bromo-3-methyl-5-isoxazolyl)-5-(benzenesulfonyl)thiophene-2-sulfonamide N-(4-Bromo-3-methyl-5-isoxazolyl)-5-(benzenesulfonyl)thiophene-2-sulfonamide was prepared: in the same manner as described in Example 2 from 5-amino-4-bromo-3-methylisoxazole and 5-benzenesulfonylthiophene-2-sulphonyl chloride in 59% yield. Purification was achieved by recrystallization from ethyl acetate/hexanes to give a crystalline solid, m.p. 139°–142° C.

EXAMPLE 16

N-(4-Bromo-3-methyl-5-isoxazolyl )-2-(carbomethoxy)thiophene-3-sulfonamide

N-(4-Bromo-3-methyl-5-isoxazolyl)-2-(carbomethoxy)thiophene-3-sulfonamide was prepared in the same manner as described in Example 2 from 5-amino-4-bromo-3-methylisoxazole and 2-(carbomethoxy)thiophene-3-sulphonyl chloride in 73% yield. Purification was achieved by recrystallization from ethyl acetate/hexanes to give a crystalline solid, m.p. 198°–200° C.

EXAMPLE 17

N-(4-Bromo-3-methyl-5-isoxazolyl)-2-(carboxyl)thiophene-3-sulfonamide

N-(4-Bromo-3-methyl-5-isoxazolyl)-2-(carbomethoxy)thiophene-3-sulfonamide (EXAMPLE 16) (1.5 g, 3.95 mmol) was dissolved in methanol (10 ml). Sodium hydroxide pellets (1 g, 25 mmol) and a few drops of water were then added. The resultant solution was stirred for 16 h at ambient temperature. Methanol was removed under reduced pressure. The residue was diluted with water and was extracted with ethyl acetate (2×10 ml). The aqueous layer was acidified (pH=2) with concentrated hydrochloric acid and was extracted with ethyl acetate (2×60 ml). The combined organic layers was dried over anhydrous magnesium sulfate and filtered. Removal of the solvent gave N-(4-bromo-3-methyl-5-isoxazolyl)-2-(carbomethoxy)thiophene-3-sulfonamide (1.2 g, 82% yield), which was purified by silica gel column chromatography using ethyl acetate as eluent, m.p. 188°–194° C.

EXAMPLE 18

N-(4-Bromo-3-methyl-5-isoxazolyl)-2-(N-phenylaminocarbonyl)thiophene-3-sulfonamide Aniline (0.093 g, 1 mmol) and 1-ethyl-3'[3-dimethylaminopropyl]carbodiimide (EDCl) (0.191 g, 1 mmol) were added to N-(4-bromo-3-methyl-5-isoxazolyl)- 2-(carboxyl)thiophene-3-sulfonamide (0.368 g, 1 mmol) that had been suspended in methylene chloride (5 ml) to produce a clear solution. Stirring was continued for 1 h at ambient temperature. The reaction mixture was diluted with methylene chloride (50 ml) and washed with 3N hydrochloric acid solution (3×50 ml). The combined organic layers was dried over anhydrous magnesium sulfate and filtered. Removal of the solvent under reduced pressure gave N-(4-bromo-3-methyl-5-isoxazolyl)- 2-(N-phenylaminocarbonyl)thiophene- 3-sulfonamide. The crude product thus obtained was purified by column chromatography using ethyl acetate as eluent to yield the product (0.32 g, 72% yield, m.p. 168°–170° C.).

EXAMPLE 19

N-(4-Bromo-3-methyl-5-isoxazolyl) 1-(4'-isopropylphenyl)pyrrole-2-sulfonamide and N-(4-Bromo-3-methyl-5-isoxazolyl) 1-(4'-isopropylphenyl)pyrrole-3-sulfonamide A.. 1-(4'-isopropylphenyl)pyrrole Glacial acetic acid (100 ml) was added to a mixture of 4-isopropylaniline (10 ml, 72.4 mmol) and 2,5-dimethoxytetrahydrofuran (9.6 ml, 72.4 mmol) and the resulting mixture was refluxed for 1.5 h. The reaction mixture was allowed to cool and acetic acid was removed under reduced pressure. The resulting brown syrup was dissolved in ethyl acetate (200 ml) and washed with water (2×200 ml). The organic layer was dried over magnesium sulfate and filtered. Removal of the solvent gave 1-(4'-isopropylphenyl)pyrrole (13.28 g, 99% yield) as a brown syrup.

B. 1-(4'-isopropylphenyl)pyrrole-2-sulfonic acid

Chlorosulfonic acid (1.82 ml, 27.08 mmol) was slowly added to a solution of 1-(4'-isopropylphenyl)pyrrole (5.01 g, 27.08 mmol) in chloroform (100 ml) at 0° C. The resulting solution was stirred at 0° C. for 1 h and for an additional 1 h at room temperature. Chloroform was removed under reduced pressure. The resultant brown liquid was diluted with ethyl acetate (200 ml) and washed with 1N sodium hydroxide. The aqueous layer was then acidified with concentrated hydrochloric acid (pH<1) and then extracted with chloroform (2×150 ml). The combined organic layers was dried over magnesium sulfate and was filtered. Removal of the solvent gave 1-(4'-isopropylphenyl)pyrrole-2-sulfonic acid as a brown syrup (3 g, 42% yield).

C. 1-(4'-isopropylphenyl)pyrrole-2-sulfonyl chloride and 1-(4'-isopropylphenyl)pyrrole- 3-sulfonyl chloride Phosphorus pentachloride (4.7 g, 22.64 mmol) was slowly added to a solution of 1-(4'-isopropylphenyl)pyrrole-2-sulfonic acid (3 g, 11.32 mmol) in phosphorus oxychloride (8.4 ml, 90.57 mmol). The resulting mixture was heated at 70° C. for 10 h. The reaction mixture was allowed to cool to room temperature, then carefully poured on to crushed ice (500 g) and extracted with chloroform (200 ml). The combined organic layers was dried over anhydrous magnesium sulfate. This was filtered and removal of the solvent yielded a 4:1 mixture of 1-(4'-isopropylphenyl)pyrrole-2-sulfonyl chloride and 1-[4'-isopropylphenyl]pyrrole- 3-sulfonyl chloride (2.5 g, 78%) as a brown oil.

D. N-(4-Bromo-3-methyl-5-isoxazolyl) 1-(4'-isopropylphenyl)pyrrole-2-sulfonamide and N-(4-Bromo-3-methyl-5-isoxazolyl) 1-( 4'-isopropylphenyl)pyrrole-3-sulfonamide N-(4-Bromo-3-methyl-5-isoxazolyl) 1-(4'-isopropylphenyl)pyrrole-2-sulfonamide and N-(4-bromo-3-methyl-5-isoxazolyl) 1-( 4'-isopropylphenyl)pyrrole-3-sulfonamide were prepared in the same manner as described in Example 2 from 5-amino-4-bromo-3-methylisoxazole and a mixture of 1-(4'-isopropylphenyl)pyrrole-2-sulfonyl chloride and 1-( 4'-isopropylphenyl)pyrrole-3-sulfonyl chloride in 65% combined yield. The mixture was subjected to preparative HPLC to give N-(4-bromo-3-methyl-5-isoxazolyl) 1-( 4'-isopropylphenyl)pyrrole-2-sulfonamide (retention time 22.85 min, 5% to 95% acetonitrile in water with 0.1% TFA over 30 min period, $C_{18}$ analytical column) and N-(4-bromo-3-methyl-5-isoxazolyl) 1-(4'-isopropylphenyl)pyrrole-3-sulfonamide (retention time 24.56 min, 5% to 95% acetonitrile in water with 0.1% TFA over 30 min period, $C_{18}$ analytical column) as oils.

EXAMPLE 20

N-(4-Bromo-3-methyl-5-isoxazolyl)- 5-bromothiophene-2-sulfonamide

N-(4-Bromo-3-methyl-5-isoxazolyl)-5-bromothiophene-2-sulfonamide was prepared in the same manner as described in Example 2 from 5-amino-4-bromo- 3-methylisoxazole and 5-bromothiophene-2-sulfonyl chloride in 30% yield. Purification was achieved by recrystallization from ethyl acetate/hexanes to give a crystalline solid, m.p. 240° C. (dec).

EXAMPLE 21

N-(4-Bromo-3-methyl-5-isoxazolyl)- 2-[N-(4-methoxyphenyl)aminocarbonyl]thiophene- 3-sulfonamide 4-Methoxyaniline (0.2:46 g, 2 mmol), bromo-tris-pyrrolidino-phosphonium hexafluorophosphate (PyBrop) (0.466 g, 1 mmol) and N,N'-diisopropylethylamine (0.15 ml) were added to N-(4-bromo-3-methyl-5-isoxazolyl)-2-(carboxyl)thiophene- 3-sulfonamide (0.368 g, 1 mmol), which had been suspended in methylene chloride (3 ml), resulting in a clear solution. Stirring was continued for 24 h at ambient temperature. The reaction mixture was diluted with methylene chloride (50 ml) and washed with 3N hydrochloric acid solution (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl- 5-isoxazolyl)-2-[N-(4-methoxyphenyl)aminocarbonyl]thiophene-3-sulfonamide. The crude product thus obtained was purified by column chromatography using ethyl acetate as eluent. This was recrystallized from ethyl acetate/hexanes to give a crystalline solid, m.p. 202°–205° C. (0.08 g, 17% yield).

EXAMPLE 22

N-(4-Bromo-3-methyl-5-isoxazolyl)- 2-[N-(3-methoxyphenyl)aminocarbonyl]thiophene- 3-sulfonamide N-(4-Bromo-3-methyl-5-isoxazolyl)-2-[N-(3-methoxyphenyl)aminocarbonyl]thiophene-3-sulfonamide was prepared in the same manner as described in Example 21 from N-(4-bromo-3-methyl-5-isoxazolyl)-2-(carboxyl)thiophene-3-sulfonamide and 3-methoxyaniline in 23% yield. The crude product was purified by column chromatography using ethyl acetate as eluent. This was recrystallized from ethyl acetate/hexanes to give a crystalline solid, m.p. 200°–202° C.

EXAMPLE 23

N-(4-Bromo-3-methyl-5-isoxazolyl)-2-[N- (2-methoxyphenyl)aminocarbonyl]- thiophene-3-sulfonamide N-(4-Bromo-3-methyl-5-isoxazolyl)-2-[N-(2-methoxyphenyl)aminocarbonyl]thiophene-3-sulfonamide was prepared in the same manner as described in Example 21 from N-(4-Bromo-3-methyl- 5-isoxazolyl)-2-(carboxyl)thiophene-3-sulfonamide and 2-methoxyaniline in 26% yield. The crude product was purified by column chromatography using ethyl acetate as eluent. This was recrystallized from ethyl acetate/hexanes to give a crystalline solid, m.p. 74°–80° C.

EXAMPLE 24

N-(4-Bromo-3-methyl-5-isoxazolyl)- 2-(N-benzylaminocarbonyl)thiophene-3-sulfonamide Benzylamine (0.214 g, 2 mmol), benzotriazole-1-yl-oxytris(dimethylamino)phosphonium hexafluorophosphate (Bop) (0.442 g, 1 mmol) and N,N'-diisopropylethylamine (0.15 ml) were added to N-(4-bromo- 3-methyl-5-isoxazolyl)- 2-(carboxyl)thiophene-3-sulfonamide (0.368 g, 1 mmol), which had been suspended in methylene chloride (3 ml). The resultant solution was stirred for 14 h at ambient temperature. This was diluted with methylene chloride (50 ml) and washed with 3N hydrochloric acid (3×50 ml) followed by 5% sodium carbonate solution (2×50 ml). The combined organic layers was dried over anhydrous magnesium sulfate and filtered. Removal of the solvent under reduced pressure gave N-(4-bromo-3-methyl-5-isoxazolyl)-

2-(N-benzylaminocarbonyl)thiophene- 3-sulfonamide. The crude product was purified by column chromatography using ethyl acetate as eluent. Recrystallization from ethyl acetate/hexanes gave a crystalline solid, m.p. 186°–190° C. (0.14 g, 30% yield).

EXAMPLE 25

N-(4-Bromo-3-methyl-5-isoxazolyl)-2-[N-(4-ethylphenyl)aminocarbonyl]thiophene-3-sulfonamide N-(4-Bromo-3-methyl-5-isoxazolyl)-2-[N-( 4-ethylphenyl)aminocarbonyl]-thiophene- 3-sulfonamide was prepared in the same manner as described in Example 24 from N-(4-bromo-3-methyl-5-isoxazolyl)-2-(carboxyl)thiophene-3-sulfonamide and 4-ethylaniline in 31% yield. The crude product was purified by column chromatography using ethyl acetate as eluent. This was recrystallized from ethyl acetate/hexanes to give a crystalline solid, m.p. 187°–190° C.

EXAMPLE 26

N-(4-Bromo-3-methyl-5-isoxazolyl)-2-[N-(4-biphenyl)aminocarbonyl]thiophene-3-sulfonamide N-(4-Bromo-3-methyl-5-isoxazolyl)-2-[N-(4-biphenyl)aminocarbonyl]thiophene-3-sulfonamide compound was prepared in the same manner as described in Example 24 from N-(4-bromo-3-methyl-5-isoxazolyl)-2-(carboxyl)thiophene-3-sulfonamide and 4-phenylaniline in 26% yield. The crude product was purified by column chromatography using ethyl acetate as eluent. This was recrystallized from ethyl acetate/hexanes to give a crystalline solid, m.p. 205°–212° C. (dec).

EXAMPLE 27

N-(3,4-dimethyl-5-isoxazolyl)-2-(carbomethoxy)thiophene-3-sulfonamide

2-Methoxycarbonylthophene-3-sulfonyl chloride (2.50 g, 10.05 mmol) was added to a solution of 5-amino-3,4-dimethylisoxazole(0.98 g, 8.75 mmol) in dry pyridine (5.0 ml). The reaction mixture was stirred at room temperature for 16 h. Pyridine was removed under reduced pressure and the residue was partitioned between water and dichloromethane. The organic layer was washed with 1N HCl (2×50 ml) and dried over anhydrous magnesium sulfate. Evaporation of the solvents left an oily residue, which, after purification by column chromatography over silica gel (1:1 hexanes/ethyl acetate as eluent), yielded 2.20 mg (65%) of a brown solid. Further purification was achieved by recrystallization from ethyl acetate/hexanes, giving the pure product as a white solid, m.p. 113°–116° C.

EXAMPLE 28

N-(3,4-dimethyl-5-isoxazolyl)-2-(carboxyl)thiophene-3-sulfonamide

N-(3,4-dimethyl-5-isoxazolyl)-2-(carboxyl)thiophene-3-sulfonamide was prepared in the same manner as described in Example 17 from N-(3,4-dimethyl- 5-isoxazolyl)-2-(carbomethoxy)thiophene-3-sulfonamide by basic hydrolysis in 94% yield. Purification was achieved by recrystallization from ethyl acetate/hexanes to give a crystalline solid, m.p. 202°–203° C.

EXAMPLE 29

N-(3,4-dimethyl-5-isoxazolyl)-2-(N-phenylaminocarbonyl)thiophene-3-sulfonamide N-(3,4-dimethyl-5-isoxazolyl)-2-(N-phenylaminocarbonyl)thiophene-3-sulfonamide was prepared in the same manner as-described in Example 18 from N-( 3,4-dimethyl-5-isoxazolyl)-2-(carboxyl)thiophene-3-sulfonamide in 40% yield. Purification was achieved by recrystallization from ethyl methanol/water to give a crystalline solid, m.p. 176°–178 C.

EXAMPLE 30

N-(4-Bromo-3-methyl-5-isoxazolyl)-5-(2'-thienyl)thiophene-2-sulfonamide

A. 5-Bromo-2,2'-bithiophene

N-bromosuccinimide (NBS, 1.12 g, 6.3 mmol) was added in small portions to a stirred solution of 1.0 g (6.01 mmol) of 2,2'-bithiophene in 10 ml of glacial acetic acid and 10ml of chloroform. After stirring for 1 h at room temperature, the mixture was poured into ice-water and extracted into chloroform (75 ml). The organic layer was washed with aqueous sodium bicarbonate solution, water, and then dried over magnesium sulfate and evaporated. The residue was subjected to flash chromatography on silica gel using hexane to give 1.3 g (88%) of a light green solid, m.p. 55°–56° C.

B. 5-Chlorosulphonyl-2,2'-bithiophene

A stirred solution of 5-bromo-2,2'-bithiophene (1.5 g, 6.1 mmol) in 10 ml of dry ether was placed under an argon atmosphere, cooled to –78° C. and 4.3 ml of a 1.7M solution of t-butyllithium was added over 20 min. Stirring was continued at this temperature for an additional 20 min. Sulfur dioxide gas was then bubbled in at –78° C. until a yellow precipitate formed. Bubbling of the sulfur dioxide gas was continued for an additional 3 min and was immediately followed by a dropwise addition of N-chlorosuccinimide (NCS, 902 mg, 6.76 mmol) that had been dissolved in THF. The mixture was warmed to room temperature and stirring was continued for an additional 1.5 h. The mixture was then concentrated and the residue dissolved in ether. The organic layer was washed with water, brine solution and dried over magnesium sulfate. Evaporation of solvent left a pale yellow solid, which was recrystallized from hexane to give 700 mg (44%) of a yellow solid, m.p. 63°–64° C.

C. N-(4-Bromo-3-methyl-5-isoxazolyl)-5-(2'-thienyl)thiophene-2-sulfonamide

N-(4-Bromo-3-methyl-5-isoxazolyl)-5-(2'-thienyl)thiophene-2-sulfonamide was prepared in the same manner as described in Example 2. Reaction of 2-chlorosulphonyl-5,2'-bithiophene (300 mg, 1.14 mmol)with 5-amino-4-bromo-3-methylisoxazole (183 mg, 1.03 mmol) yielded, after flash chromatography using 10% MeOH/CHCl$_3$, 430 mg (94%) of a pale brown solid, m.p. 210° C.

EXAMPLE 31

N-(4-Bromo-3-methyl-5-isoxazolyl)thiophene-3-sulfonamide

A. Thiophene-3-sulfonyl chloride

A stirred solution of 3-bromothiophene (1.5 g, 9.2 mmol) in 10 ml of dry ether was placed under an argon atmosphere and cooled to –78° C. Over the course of 20 min, a solution of t-butyllithium (5.6 ml of a 1.7M) was added and stirring was continued at this temperature for an additional 20 min. Sulfur dioxide gas was then bubbled in at −78° C. and the solution was warmed to 0° C., whereupon NCS (1.47 g, 12 mmol. in 8 ml of THF, was added dropwise. After warming to room temperature, stirring was continued for an additional 1 hour, after which, evaporation of solvents left 1.55 g of a brown oil. Flash chromatography over silica gel using hexanes yielded 1.24 g (74%) of a yellow oil which solidified on standing to give a yellow crystalline solid, m.p. 38°–39° C.

B. N-(4-Bromo-3-methyl-5-isoxazolyl)thiophene-3-sulfonamide

N-(4-Bromo-3-methyl-5-isoxazolyl)thiophene-3-sulfonamide was prepared in the same manner as described in Example 2 from thiophene-3-sulfonyl chloride with 5-amino-4-bromo-3-methylisoxazole in 22% yield. Purification by column chromatography using 10% MeOH/CHCl$_3$ as eluent gave a pale brown oil.

EXAMPLE 32

N-(3,4-dimethyl-5-isoxazolyl)-5-phenylthiophen-2-sulfonamide

A. N-(3,4-dimethyl-5-isoxazolyl)-5-bromothiophene-2-sulfonamide

A solution of 5-bromothiophene-2-sulfonyl chloride (2.75 g, 10 mmol) and 5-amino-3,4-dimethylisoxazole (1.07 g, 9.57 mmol) in pyridine containing a catalytic amount of 4-dimethylaminopyridine (DMAP, 10 mg) was stirred at room temperature for a period of 3 h. The solution was heated at 50° C. for an additional 1.5 h to drive the reaction to completion as judged by TLC. The pyridine was removed under reduced pressure and the residue, after extraction into ethyl acetate, was washed with 1N HCl (2×25 ml), water (1×25), brine solution, (1×25 ml) and dried over magnesium sulfate. Evaporation of solvent left a viscous brown gum, which was subjected to flash chromatography. Elution with 3% methanol hexanes gave 246 mg (10%) of pure sulfonamide.

B. N-(methoxyethoxymethyl)-N-(3,4-dimethyl-5-isoxazolyl)-5-bromothiophene-2-sulfonamide N-(4-Methyl-3-methyl-5-isoxazolyl)-5-bromothiophene-2-sulfonamide (680 mg, 2 mmol) in dry THF (2 ml) was added to sodium hydride (121 mg of a 60% oil dispersion, 3 mmol) in dry THF (1 ml). The resulting suspension was cooled to 0° C. and methoxy ethoxymethyl chloride (334 mg, 2.68 mmol) was added dropwise via syringe. The solution was warmed to room temperature, and stirring continued overnight. Evaporation of solvent left an oil that was extracted into ethyl acetate, washed with brine, dried over magnesium sulfate and evaporated. Flash chromatography of the residue on silica gel using 10–15% ethylacetate/hexanes yielded 480 mg (56%) of a colorless oil.

C. N-(methoxyethoxymethyl)-N-(3,4-dimethyl-5-isoxazolyl)- 5-phenylthiophene-2-sulfonamide Sodium carbonate (2 ml of a 2M aqueous solution) followed by phenyl boronic acid (86 mg, 0.71 mmol) in 2 ml of 95% ethanol were added to a solution of N-(methoxyethoxymethyl)-N-(4-methyl-3-methyl- 5-isoxazolyl)-5-bromothiophene- 2-sulfonamide (200 mg, 0.47 mmol) and tetrakis (triphenylphosphine) palladium (0) (23 mg, 0.02 mmol) in dry benzene (4 ml) under argon. The mixture was refluxed for 12 h, diluted with 5 ml of water and extracted into ethyl acetate (3×25 ml). The combined organic extracts was washed with brine (1×25 ml), dried and evaporated. The residue was flash chromatographed on silica gel using 25% ethylacetate/hexanes to afford 123 mg (62%) of the sulfonamide as a colorless gum.

D. N-(3,4-dimethyl-5-isoxazolyl-5-phenylthiophen-2-sulfonamide

HCl (3 ml of a 3N aqueous solution) was added to a solution of N-(methoxyethoxymethyl)-N-( 3,4-dimethyl-5-isoxazolyl)-5-phenylthiophene-2-sulfonamide (100 mg, 0.24 mmol) in 3 ml of 95% ethanol and the resulting mixture was refluxed for 6 h. The mixture was then concentrated, diluted with 5 ml of water, neutralized with saturated aqueous sodium bicarbonate solution and acidified to pH 4 using glacial acetic acid. The mixture was extracted with ethyl acetate (2×25 ml) and the combined organic extract was washed with brine (1×5 ml), dried and evaporated. Flash chromatography of the residue on silica gel using 2% MeOH/CHCl$_3$ and further purification by reverse phase HPLC yielded 33.4 mg (42%) of the pure sulfonamide as a white powder, m.p. 176°–178° C.

EXAMPLE 33

N-(4-Bromo-3-methyl-5-isoxazolyl)-5-(4-ethylphenyl)thiophene-2-sulfonamide

A. N-(5-Bromothiophene-2-sulfonyl)-pyrrole

Sodium hydride (60% oil dispersion, 191 m.g., 4.78 mmol) was suspended in dry tetrahydrofurn (2 ml) and the resulting cloudy suspension was cooled to 0° C. in an ice bath. Pyrrole (385 mg, 5.75 mmol) in dry tetrahydrofuran (2 ml) was added dropwise over a period at 10 min. The ice bath was removed and the solution was stir at room temperature until gas evolution ceased (15 minutes), whereupon 5-bromothiophene-2-sulfonyl chloride (1.0 g, 3.82 mmol) previously dissolved in tetrahydrofuran (4.0 ml) was added dropwise through a steel cannula. After stirring for 1 h at room temperature, the mixture was filtered through Celite. The filter pad rinsed with tetrahydrofuran. The filtrate was evaporated, which left a light brown solid that was recrystallized from methanol to produce the sulfonamide (821 mg, 74% yield) as a white powder.

B. 4-Ethylphenylboronic acid

A solution of 1-bromo-4-ethyl benzene (2.0 g, 11 mmol) in dry ether (5 ml) was added to magnesium turnings (311 mg, 13 mmol), which had been suspended in dry ether, by a dropwise addition. After addition was complete, the suspension was refluxed for a period of 15 min after which nearly all of the magnesium had reacted. This solution was then added to trimethy borate (1.12 g, 11 mmol) previously dissolved in ether (5 ml) at −78° C., the solution was warmed to room temperature and stirred for 90 min. The reaction was quenched by the addition of 10% aqueous HCl (2 ml) and the solution was extracted with ether. The combined ether extracts was extracted with 1M NaOH (2×20 ml), the aqueous extracts were acidified with dilute HCl to pH 2 and extracted with ether (2×25 ml). The combined ether extracts was washed once with water (10 ml), dried and evaporated to produce a white solid (676 mg, 38% yield), m.p. 138°–140° C.

C. N-(Pyrrole)-5-(4-ethylphenyl)thiophene-2-sulfonamide

N-(Pyrrole)-5-(4-ethylphenyl)thiophene-2-sulfonamide was prepared, in the same manner as described in Example 32C, from 4-ethylphenylboronic acid and N-(5-bromothiophenesulfonyl)pyrrole. Purification by column chromatography using 10% ethyl acetate/hexanes gave the pure sulfonamide as a tan solid in 81% yield.

D. 5-Chlorosulphonyl-2-(4-ethylphenyl)thiophene

A solution of N-(pyrrole)-5-(4-ethylphenylthiophene)-2-sulfonamide (100 mg, 0.32 mmol) and 6N sodium hydroxide (1 ml) in methanol (1.5 ml) was refluxed for approximately 6 h. Evaporation of solvents and drying in vacuo resulted in an oil. Phosphorus oxychloride (258 ml, 2.52 mmol) and phosphorus pentachloride (131 mg, 0.63 mmol) were added to the oil and the resulting brown suspension was heated at 50° C. for 3 h. The resulting clear brown solution was carefully added to about 20 ml of crushed ice and then extracted with ethyl acetate (3×25 ml). The combined organic layers was washed with brine (2×5 ml), dried (MgSO$_4$) and evaporated to leave an oily residue. Flash chromatography over silica gel using 2% ethyl acetate/hexanes yielded (53 mg, 59%) of the pure sulphonyl chloride as a pale yellow oil.

E. N-(4-Bromo-3-methyl-5-isoxazolyl)-5-(4-ethylphenyl)thiophene-2-sulfonamide

N-(4-Bromo-3-methyl-5-isoxazolyl)- 5-(4-ethylphenyl)thiophene-2-sulfonamide was prepared in the same manner as described in Example 2. Reaction of 5-chlorosulphonyl-2-(4-ethylphenyl) thiophene (47.1 mg, 11.16 mmol) with 5-amino-4-bromo-3-methyl isoxazole (29 mg, 0.16 mmol) yielded, after flash chromatography using 10% MeOH/CHCl$_3$, a pale brown solid (46 mg, 66% yield), m.p. 172°–175° C.

EXAMPLE 34

N-3,4-dimethyl-5-isoxazolyl)benzo[b] thiophene-2-sulfonamide

A. Benzo[b]thiophene-2-sulfonyl chloride

Benzo[b]thiophene (1.50 g, 11.2 mmol) was stirred at 0° C. in 20 ml of THF. t-Butyllithium (t-BuLi, 1.7M, 16.8 mmol, 9.9 ml) was slowly added over a 5 minute period. Fifteen minutes later, SO$_2$ was flushed into the reaction flask and a thick white precepitate formed. The reaction mixture was stirred for 15 minutes at 0° C. and then NCS (1.64 g, 12.3 mmol) was added. The reaction was warmed to 25° C. and stirred for 30 min. It was then poured into ethyl acetate (150 ml) and washed with brine (3×100 ml). The organic phase was dried with MgSO$_4$, filtered and concentrated to collect 2.29 g of a brown oil. The brown oil was subjected to flash chromatography (5% ethyl acetate/hexanes), which provided a yellow tan solid (1.39 g, 53% yield).

B. N-(3,4-dimethyl-5-isoxazolyl)benzo[b]thiophene-2-sulfonamide 3,4-Dimethyl-5-amino-isoxazole (0.224 g, 2.0 mmol) and 50 mg of DMAP were stirred in 5 ml of pyridine at 25° C. The benzo[b]thiophene-2-sulfonyl chloride (0.16 g, 2.6 mmol) was added and the dark brown-yellow reaction mixture was poured into 100 ml of ethyl acetate and washed with 2% HCl (3×50 ml). The organic phase was dried with MgSO$_4$, filtered and concentrated to collect 0.61 g of a brown oil/solid. The brown oil/solid was subjected to flash chromatography (30% ethyl acetate/hexanes) to provide 0.37 g of a light brown solid. This was stirred in 10 ml of methanol and 0.5 g of NaOH. The methanolic solution was heated for reflux for 1 h, then cooled to 25° C. and the methanol was removed in vacuo. The resulting residue was acidified to pH 1 with 2% HCl (100 ml) and extracted with ethyl acetate (2×50 ml) The organic phase was dried with MgSO$_4$, filtered and concentrated to collect 0.225 g of a yellow-orange solid. This was recrystallized from CHCl$_3$/Hexanes to produce a light tan-yellow solid (0.194 g, 31% yield), m.p. 157°–160° C.

EXAMPLE 35

N-(3,4-Dimethyl-5-isoxazolyl)benzo[b] furan-2-sulfonamide

A. Benzo[b]furan-2-sulfonyl chloride

Benzo[b]furan-2-sulfonyl chloride was prepared as in Example 34A from benzo[b]furan (1.61 g, 13.6 mmol), t-BuLi (1.7M, 17.7 mmol, 10.4 ml) and NCS (2.0 g, 15.0 mmol). Flash chromatography (5% ethyl acetate/hexanes) yielded a brown solid (1.84 g, 62% yield).

B. N-(3,4-Dimethyl-5-isoxazolyl)benzo[b]furan-2-sulfonamide

N-(3,4-Dimethyl-5-isoxazolyl)benzo[b]furan-2-sulfonamide was prepared, in the same manner as described in Example 34B, from 3,4-dimethyl-5-amino isoxazole (78 mg, 0.70 mmol) and benzo[b]furan-2-sulfonyl chloride (0.46 g, 2.1 mmol) Flash chromatography (30% ethyl acetate/hexanes) provided 0.186 g of a light yellow solid, which was treated with 31 mg of NaOH in 10 ml of methanol at 25° C. for 30 minutes. Recrystallization from CHCl$_3$/hexanes yielded a light tan solid (90 mg, 44% yield), m.p. 160.5°–163° C.

EXAMPLE 36

N-(3,4-dimethyl-5-isoxazolyl)furan-2-sulfonamide

A. Furan-2-sulfonyl chloride

Furan-2-sulfonyl chloride was prepared as in Example 34A from furan (0.96 g, 14.2 mmol), t-BuLi (1.7M, 17 mmol, 10 ml) and NCS (2.27 g, 17 mmol) using ether (30 ml) as the solvent. Flash chromatography (5% ethyl acetate/hexanes) produced a yellow liquid (1.22 g, 52% yield).

B. N-(3,4-dimethyl-5-isoxazolyl)furan-2-sulfonamide

N-(3,4-dimethyl-5-isoxazolyl)furan-2-sulfonamide was prepared as described in Example 34B from 3,4-dimethyl-5-amino isoxazole (0.122 g, 1.0 mmol), furan-2-sulfonyl chloride (0.50 g, 3.0 mmol) and NaOH (64 mg). Flash chromatography (50% ethyl acetate/hexanes) yielded 70 mg of a yellow solid. Recrystallization from CHCl$_3$/hexanes produced an off-white solid (46 mg, 29% yield), m.p 107°–110° C.

EXAMPLE 37

N-(3,4-Dimethyl-5-isoxazolyl)-3-methoxy-2-thiophene sulfonamide

A. 3-methoxy-2-thiophenesulfonyl chloride

Chlorosulfonic acid (ClSO$_3$H, 2.31 g, 19.62 mmol) was slowly added at 0° C. to a solution of 3-methoxythiophene (2.29 g, 19.62 mmol) in CHCl$_3$ (80 ml) The resulting mixture was stirred at 0° C. for 30 min. The solvent was evaporated under reduced pressure, at room temperature, the residue was suspended in POCl$_3$ (15 ml, 156.96 mmol), and PCl$_5$ (8.2 g, 39.24 mmol) was added slowly. The reaction was stirred at 60° C. for 18 h, then cooled to room temperature and poured onto crushed ice (200 g). The aqueous mixture was extracted with CHCl$_3$ (2×150 ml) and the combined organic layers was dried (MgSO$_4$). The solid was removed by filtration and the filtrate was concentrated to give 3-methoxy-2-thiophenesulfonyl chloride as a brown oil (1.81 g, 43% yield).

B. N-(3,4-dimethyl-5-isoxazolyl)-3-methoxy-2-thiophene sulfonamide

Sodium hydride (1.02 g, 25.56 mmol, 60% dispersion in mineral oil) was slowly added to a solution of 3-methoxy-2-thiophenesulfonyl chloride (1.18 g, 8.52 mmol) and 3,4-dimethyl-5-aminoisoxazole (1.05 g, 9.37 mmol) in THF (20 ml) at room temperature. The resulting mixture was refluxed for 4 h. THF was removed under reduced pressure. The residue was dissolved in water (10 ml), the pH was adjusted to 10°–11 by adding 5N sodium hydroxide solution, and was extracted with ethyl acetate (3×10 ml) to remove the neutral impurities. The aqueous layer was acidified with concentrated HCl (pH 2–3) and extracted with methylene chloride (3×10 ml). The combined organic layers was dried over anhydrous magnesium sulfate to produce a crude oil. Further purification by reverse phase HPLC yielded a yellow oil (retention time 14.94 min, 5% to 95% acetonitrile in $H_2O$ with 0.1% TFA over 30 min period, $C_{18}$ analytical column).

EXAMPLE 38

N-(4-Bromo-3-methyl-5-isoxazolyl)-3-phenyl-2-thiophene sulfonamide and N-(4-Bromo-3-methyl-5-isoxazolyl)4-phenyl-2-thiophene sulfonamide A. 3-phenyl-2-thiophenesulfonyl chloride and 4-phenyl-2-thiophenesulfonyl chloride Butyllithium (2.38M, 17.2 ml, 41.03 mmol) was slowly added to a solution of 3-phenylthiophene (5.47 g, 34.2 mmol) in $Et_2O$ (25 ml) at 0° C. The ice bath was removed, the mixture was stirred at room temperature for 2 h, cooled to −30° C. ($CO_2$/acetone) and $SO_2$ gas was bubbled through the reaction mixture for 20 min. A solution of NCS (6.06 g, 44.5 mmol) in THF (20 ml) was then added. The reaction was allowed to warm to room temperature and stirred for 16 h. The crude mixture was filtered, and the solid was washed with $Et_2O$. The combined organic layers was concentrated and the residue was chromatographed (hexanes/$CHCl_3$) to give 3-phenyl-2-thiophenesulfonyl chloride and 4-phenyl-2-thiophenesulfonyl chloride as a 1:1 mixture (1.46 g, 16.5%, while solid).

B. N-(4-Bromo-3-methyl-5-isoxazolyl)-3-phenyl-2-thiophene sulfonamide and N-(4-Bromo-3-methyl-5-isoxazolyl)-4-phenyl-2-thiophene sulfonamide N-(4-Bromo-3-methyl-5-isoxazolyl)-3-phenyl-2-thiophene sulfonamide and N-(4-bromo-3-methyl-5-isoxazolyl)-4-phenyl-2-thiophene sulfonamide were prepared as described in Example 1. A fraction of the crude mixture of products was purified by HPLC to give N-(4-bromo-3-methyl-5-isoxazolyl)- 3-phenyl- 2-thiophene sulfonamide (light brown solid, retention time 20.48 min, 5% to 95% acetonitrile in water with 0.1% TFA over 30 min $C_{18}$ analytical column, m.p. 105°–107° C.) and N-(4-bromo-3-methyl-5-isoxazolyl)-4-phenyl-2-thiophene sulfonamide (dull yellow solid, m.p. 108°–110° C., retention time 21.35 min, same conditions).

EXAMPLE 39

Other compounds in which $Ar^2$ is contains a heterocyclic ring, such as thiophenyl-, furyl- and pyrrole-sulfonamides of interest herein can be prepared by methods analogous to those set forth in Examples 1–38.

EXAMPLE 40

N-(4-Bromo-3-methyl-5-isoxazolyl)benzenesulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product which was purified by column chromatography using 9:1, hexanes/ethyl acetate as eluent to give 5-amino-4-bromo-3-methylisoxazole (1.55 g, 87% yield).

(b) N-(4-Bromo-3-methyl-5-isoxazolyl)benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol) in dry THF (1 ml) at 0°–5° C. After stirring at 0°–5° C. for 10 min., the reaction was warmed to room temperature for 10 min. to complete the reaction. The reaction mixture was re-cooled to 0° C. and benzenesulfonyl chloride (0.283 ml, 2.2 mmol) was added slowly. Stirring was continued for 20 min. at 0°–5° C. Excess sodium hydride was decomposed by addition of methanol (0.4 ml) followed by water (0.5 ml). The solvent was removed under reduced pressure. The residue was dissolved in water (20 ml), basified to pH 8–9 by the addition of sodium hydroxide and extracted with ethyl acetate (2×10 ml) to remove the neutral impurities. The aqueous layer was acidified with concentrate HCl (pH 2–3) and extracted with ethyl acetate (3×10 ml) The combined organic layer was dried over magnesium sulfate and concentrated under reduced pressure to give N-(4-bromo-3-methyl-5-isoxazolyl)benzenesulfonamide. The pure material was obtained by recrystallization using hexanes/ethyl acetate (0.59 g, 93% yield), m.p. 142°–144° C.

EXAMPLE 41

N-(4-Bromo-5-tert-butyl-3-isoxazolyl) benzenesulfonamide (a) 3-Amino-4-bromo-5-tert-butylisoxazole This compound was prepared from 3-amino-5-tert-butylisoxazole and N-bromosuccinimide as described in Example 44a in 91% yield, $R_f$ 0.27 (3:1 hexanes/ethyl acetate).

(b) N-(4-Bromo-5-tert-butyl-3-isoxazolyl)benzenesulfonamide

3-Amino-4-bromo-5-tert-butylisoxazole (21 9 mg, 1.0 mmol) was dissolved in dry pyridine (1 ml). Benzenesulfonyl chloride (0.14 ml, 1.1 mmol) and 4-dimethylaminopyridine (5 mg) were added and the solution was stirred at 50° C. for 6 h. The reaction mixture was diluted with dichloromethane (75 ml), washed with 1N HCl (50 ml) and dried over anhydrous magnesium sulfate. The solvent was removed under reduced pressure to yield a crude product, which was purified by column chromatography (9:1 hexanes/ethyl acetate). A crystalline solid was obtained after recrystallization from ethyl acetate/hexanes, m.p. 139°–141° C.

EXAMPLE 42

N-(3-Methyl-4-phenyl-5-isoxazolyl)benzenesulfonamide (a) N-(Benzenesulfonyl)-N-(3-methyl-4-phenyl-5-isoxazolyl)benzenesulfonamide 5-Amino-3-methyl-4-phenylisoxazole (0.174 g, 1.0 mmol) was dissolved in dry pyridine (2 ml). Benzenesulfonyl chloride (0.389 g, 2.2 mmol) was added with stirring at ambient temperature. N,N-Dimethylaminopyridine (5 mg) was added and stirring was continued at 50° C. for 4 h. The reaction mixture was diluted with dichloromethane (75 ml), washed with 1N HCl (2×50 ml) and the organic phase was dried over magnesium sulfate. The solvent was removed under reduced pressure to yield a crude product that was purified by column chromatography using 5:1, hexanes/ethyl acetate to give 0.390 g (85% yield) of N-benzenesulfonyl-N-(4-bromo-3-methyl-5-isoxazolyl)benzenesulfonamide.

(b) N-(3-Methyl-4-phenyl-5-isoxazolyl)benzenesulfonamide

N-Benzenesulfonyl-N-(3-methyl-4-phenyl-5-isoxazolyl)benzenesulfonamide (300 mg, 0.66 mmol) was dissolved in methanol. Potassium hydroxide (300 mg, 5.5 mmol) was added and the solution was warmed to 45° C. to dissolve the sodium hydroxide. Stirring was continued for 20 min. Methanol was removed under reduced pressure. The residue was dissolved in water, cooled to 0° C. and acidified to pH 3–4 with concentrated HCl. The solid precipitate was extracted with ethyl acetate, dried and evaporated in vacuo to give 210 mg (100% yield) of N-(3-methyl-4-phenyl-5-isoxazolyl)benzenesulfonamide, which was further purified by recrystallization from ethyl acetate/hexanes, m.p. 124°–126° C.

EXAMPLE 43

N-(4-Bromo-3-phenyl-5-isoxazolyl)benzenesulfonamide

This compound was prepared from benzenesulfonyl chloride and 5-amino- 4-bromo-3-phenylisoxazole according to the method in Example 40b in 36% yield. Recrystallization from methanol gave a yellow solid, m.p. 113°–115° C.

EXAMPLE 44

N-(4-Bromo-3-tert-butyl-5-isoxazolyl)bensenesulfonamide (a) 5-Amino-4-bromo-3-tert-butylisoxazole 5-Amino-4-bromo-3-tert-butylisoxazole was prepared from 5-amino-3-tert-butylisoxazole and N-bromosuccinimide in 64% yield as described in Example 40a.

(b) N-Benzenesulfonyl-N-(4-Bromo-3-tert-butyl-5-isoxazolyl)benzenesulfonamide

5-Amino-4-bromo-3-tert-butylisoxazole (440 mg, 2.0 mmol) was dissolved in dry pyridine (2 ml). Benzenesulfonyl chloride (344 mg, 2.0 mmol) and 4-dimethylaminopyridine (5 mg) was added and the reaction was stirred at 50° C. for 16 h. The reaction mixture was diluted with ethyl acetate (20 ml), washed with 1N HCl (2×10 ml) and the organic phase was dried over magnesium sulfate. The solvent was removed under reduced pressure to yield a crude product, which was recrystallized from ethyl acetate/hexanes to give 300 mg (60% yield) of N-benzenesulfonyl-N-(4-bromo-3-tert-butyl-5-isoxazolyl)benzenesulfonamide.

(c) N-(4-Bromo-3-tert-butyl-5-isoxazolyl)benzenelsulfonamide

N-Benzenesulfonyl-N-(4-bromo-3-tert-butyl-5-isoxazolyl)benzenesulfonamide (80 mg, 0.16 mmol) was dissolved in methanol (2 ml). Sodium hydroxide (0.120 g, 3.0 mmol) in methanol was added and the solution was stirred at 45° C. for 20 min. Methanol was removed under reduced pressure. The residue was dissolved in water, cooled to 0° C. and acidified to pH 3–4 with concentrated hydrochloric acid and extracted with ethyl acetate. The extract was dried over anhydrous magnesium sulfate and concentrated in vacuo to give 5N-(4-bromo-3-tert-butyl-5-isoxazolyl)benzenesulfonamide in 94% yield. Further purification was achieved by recrystallization from methanol/water, giving an off white solid, m.p. 108°–109° C.

EXAMPLE 45

4-tert-Butyl-N-(4-bromo-3-methyl-5-isoxazolyl)benzenesulfonamide

A solution of 5-amino-4-bromo-3-methylisoxazole (354 mg, 2.0 mmol) in dry THF (1 ml) was added to a suspension of sodium hydride (60% dispersion in mineral oil, 188 mg, 4.4 mmol) in dry THF (1 ml) at 0°–5° C. After stirring at 0°–5° C. for 10 min., the reaction was warmed to room temperature for 10 min. to complete the reaction. The reaction mixture was re-cooled to 0° C. and 4-tert-butylbenzenesulfonyl chloride (512 mg, 2.2 mmol) was added slowly. Stirring was continued for 20 min. at 0°–5° C. Excess sodium hydride was decomposed by addition of methanol (0.4 ml) followed by water (0.5 ml). The mixture was acidified with hydrochloric acid and extracted with dichloromethane. The extract was dried over anhydrous magnesium sulfate and the solvent was removed under reduced pressure to give a crude product, which was purified by recrystallization from ethyl acetate/hexanes to give a white solid in 21% yield, m.p. 170° C. (dec.).

EXAMPLE 46

4-iso-Propyl-N-(4-bromo-3-methyl-5-isoxazolyl)benzenesulfonamide 4-iso-Propyl-N-(4-bromo-3-methyl-5-isoxazolyl)benzenesulfonamide was prepared in the same manner as described in Example 45 from 5-amino- 4-bromo- 3-methylisoxazole and 4-iso-propylbenzenesulfonyl chloride in 77% yield. Purification was achieved by recrystallization from ethyl acetate/hexanes to give a crystalline solid, m.p. 130°–133° C.

EXAMPLE 47

4-Bromo-N-(4-bromo-3-methyl-5-isoxazolyl)benzenesulfonamide

4-Bromo-N-(4-bromo-3-methyl-5-isoxazolyl)benzenesulfonamide was prepared in the same manner as described in Example 45 from 5-amino-4-bromo- 3-methylisoxazole and 4-bromobenzenesulfonyl chloride in 74% yield. Purification was achieved by recrystallization from ethyl acetate/hexanes to give a crystalline solid, m.p. 146°–149° C.

EXAMPLE 48

4-Fluoro-N-(4-bromo-3-methyl-5-isoxazolyl) benzenesulfonamide

4-Fluoro-N-(4-bromo-3-methyl-5-isoxazolyl)benzenesulfonamide was prepared in the same manner as described in Example 45 from 5-amino- 4-bromo- 3-methylisoxazole and 4-fluorobenzenesulfonyl chloride in 71% yield. Purification was achieved by recrystallization from ethyl acetate/hexanes to give a crystalline solid, m.p. 142°–144° C.

EXAMPLE 49

3-Nitro-N-(4-bromo-3-methyl-5-isoxazolyl)benzenesulfonamide

3-Nitro-N-(4-bromo-3-methyl-5-isoxazolyl)benzenesulfonamide was prepared in the same manner as described in Example 45 from 5-amino- 4-bromo-3-methylisoxazole and 3-nitrobenzenesulfonyl chloride in 55% yield. Purification was achieved by recrystallization from ethyl acetate/hexanes to give a crystalline solid, m.p. 151°–153° C.

EXAMPLE 50

N-(4-Bromo-5-methyl-3-isoxazolyl) benzenesulfonamide (a) 3-Amino-4-bromo-5-methylisoxazole 3-Amino-5-methylisoxazole (1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography using 9:1, hexanes/ethyl acetate as eluent, to give 3-amino-4-bromo-5-methylisoxazole (1.40 g, 40% yield).

(b) N-(4-bromo-5-methyl-3-isoxazolyl)benzenesulfonamide and N-(benzenesulfonyl)N-(4-bromo-5-methyl-3-isoxazolyl)benzenesulfonamide 3-Amino-4-bromo-5-methylisoxazole (5.31 g, 30 mmol) was dissolved in dry pyridine (30 ml). Benzenesulfonyl chloride (5.24 ml, 42 mmol) was added dropwise with stirring at ambient temperature. N,N-(Dimethyl)aminopyridine (100 mg) was added and stirring was continued at 50° C. for 25 h. The reaction mixture was diluted with dichloromethane (200 ml), washed with 1N HCl (6×100 ml) and the organic phase was dried over magnesium sulfate. The solvent was removed under reduced pressure to yield a crude product which was purified by column chromatography using 9:1, hexanes/ethyl acetate as eluent to give N-(benzenesulfonyl)-N-(4-bromo-5-methyl-3-isoxazolyl)benzenesulfonamide (7 g, 51% yield, $R_f$=0.27 using 3:1, hexanes/ethyl acetate as eluent) as a solid.

Further elution with ethyl acetate gave N-(4-bromo-5-methyl-3-isoxazolyl)benzenesulfonamide (2 g, 21% yield, $R_f$=0.08 with 3:1 hexanes/ethyl acetate as eluent), m.p. 128°–130° C.

(c) N-(4-bromo-5-methyl-3-isoxazolyl)benzenesulfonamide

Sodium hydroxide (1.3 g, 30.6 mmol) was added to a solution of N-(benzenesulfonyl)-N-(4-bromo-5-methyl-3-isoxazolyl)benzene-sulfonamide (7 g, 15.3 mmol, prepared as described in (a)) in methanol (100 ml). The resulting solution was stirred at 25° C. for 30 h. Excess methanol was removed under reduced pressure. The residue was dissolved in water (50 ml) and acidified (pH 3–4) by the addition of concentrated HCl with cooling. The mixture was extracted with dichloromethane (2×100 ml) and the combined organic layer was dried over anhydrous magnesium sulfate. Removal of the solvent gave N-(4-bromo-5-methyl-3-isoxazolyl)benzenesulfonamide which was purified by crystallization from ethyl acetate/hexanes (4.5 g, 92% yield). The compound is identical to the one isolated in step (b).

EXAMPLE 51

N-(4-Bromo-5-methyl-3-isoxazolyl)-1-naphthalenesulfonamide

N-(4-Bromo-5-methyl-3-isoxazolyl)-1-naphthalenesulfonamide was prepared from 3-amino-4-bromo-5-methylisoxazole and 1-naphthalenesulfonyl chloride as described in Example 41 in 51% yield. Recrystallization from ethyl acetate/hexanes gave a crystalline solid, m.p. 167°–170° C.

EXAMPLE 52

N-(4-Chloro-3-methyl-5-isoxazolyl) benzenesuolfonamide (a) 5-Amino-4-chloro-3-methylisoxazole Using the method in Example 40a, 5-amino-4-chloro-3-methylisoxazole was prepared in 90% yield from 5-amino-3-methylisoxazole and N-chlorosuccinimide.

(b) N-(4-Chloro-3-methyl-5-isoxazolyl)benzenesuolfonamide

N-(4-Chloro-3-methyl-5-isoxazolyl)benzenesuolfonamide was prepared according to the method in Example 40b from 5-amino-4-chloro-3-methylisoxazole and benzenesulfonyl chloride in 84% yield. The crude product was purified by recrystallization using hexanes/ethyl acetate, m.p. 140°–143° C.

EXAMPLE 53

N-(4-Chloro-5-methyl-3-isoxazolyl) benzenesulfonamide (a) 3-Amino-4-chloro-5-methylisoxazole This compound was prepared from 3-amino-5-methylisoxazole and N-chlorosuccinimide as described in Example 40a except the reaction was changed to 35° C. and the reaction time was extended to 12 h. The yield was 62%, $R_f$ 0.17 (3:1 hexanes/ethyl acetate).

(b) N-(4-Chloro-5-methyl-3-isoxazolyl)benzenesulfonamide

N-(4-chloro-5-methyl-3-isoxazolyl)benzenesulfonamide was prepared from 3-amino-4-chloro-5-methylisoxazole and benzenesulfonyl chloride as described in Example 41b in 40% yield. The crude product was purified by column chromatography with 10–100% ethyl acetate/hexanes as eluent. A crystalline solid was obtained after recrystallization from ethyl acetate/hexanes, m.p. 139°–141° C. 3-Amino-4-chloro-5-methylisoxazole (25% recovery) and N-(benzenesulfonyl)-N-(4-chloro-5-methyl-3-isoxazolyl)benzen esulfonamide (7% yield) were also obtained as less polar products.

EXAMPLE 54

4-Iodo-N-(4-bromo-3-methyl-5-isoxazolyl) benzenesulfonamide

4-Iodo-N-(4-bromo-3-methyl-5-isoxazolyl)benzenesulfonamide was prepared from 5-amino-4-bromo-3-methylisoxazole and 4-iodobenzenesulfonyl chloride according to the procedures described in Example 40b. The crude product was purified by recrystallization from ethyl acetate/hexanes to give a yellow powder, m.p. 166°–173° C., yield 65%.

EXAMPLE 55

4-Chloro-N-(4-bromo-3-methyl-5-isoxazolyl)benzenesulfonamide

4-Chloro-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 40b. The crude product was purified by recrystallization from ethyl acetate/hexanes to give a yellow powder, m.p. 145°–150° C., yield 93%.

EXAMPLE 56

N-(4-Bromo-3-ethyl-5-isoxazolyl)benzenesulfonamide (a) 5-Amino-4-bromo-3-ethylisoxazole 5-Amino-4-bromo-3-ethylisoxazole was prepared from 5-amino-3-ethylisoxazole and N-bromosuccinimide as described in Example 40a.

(b) N-(4-Bromo-3-ethyl-5-isoxazolyl)benzenesulfonamide

N-(4-Bromo-3-ethyl-5-isoxazolyl)benzenesulfonamide was prepared from 5-amino-4-bromo-3-ethylisoxazole and benzenesulfonyl chloride according to the procedures described in Example 40b. The crude product was purified by recrystallization from ethyl acetate/hexanes to give off-white crystals, m.p. 90°–93° C., yield 70%.

EXAMPLE 57

N-(4-Bromo-3-methyl-5-isoxazolyl)-4-toluenesulfonamide

N-(4-Bromo-3-methyl-5-isoxazolyl)-4-toluenesulfonamide was prepared from 5-amino-4-bromo-3-methylisoxazole and 4-toluenesulfonyl chloride according to the procedures described in Example 40b. The crude product was purified by recrystallization from ethyl acetate/hexanes to give off-white crystals, m.p. 169°–172° C., yield 69%.

EXAMPLE 58

2,5-Dimethyl-N-(4-bromo-3-methyl-5-isoxazolyl) benzenesulfonamide 2,5-Dimethyl-N-(4-bromo-3-methyl-5-isoxazolyl)benzenesulfonamide was prepared from 5-amino-4-bromo-3-methylisoxazole and 2,5dimethylbenzenesulfonyl chloride according to the procedures described in Example 40b. The crude product was purified by recrystallization from ethyl acetate/hexanes to give off-white crystals, m.p. 102°–104° C., yield 81%.

EXAMPLE 59

N-(4-Bromo-3-methyl-5-isoxazolyl)-2-toluenesulfonamide

N-(4-Bromo-3-methyl-5-isoxazolyl)-2-toluenesulfonamide was prepared from 5-amino-4-bromo-3-methylisoxazole and 2-toluenesulfonyl chloride according to the procedures described in Example 40b. The crude product was purified by recrystallization from ethyl acetate/hexanes to give white crystalline solid, m.p. 93°–96° C., yield 88%.

EXAMPLE 60

2-Fluoro-N-(4-bromo-3-methyl-5-isoxazolyl) benzenesulfonamide

2-Fluoro-N-(4-bromo-3-methyl-5-isoxazolyl)benzenesulfonamide was prepared from 5-amino-4-bromo-3-methylisoxazole and 2-fluorobenzenesulfonyl chloride according to the procedures described in Example 40b. The crude product was purified by recrystallization from ethyl acetate/hexanes to give a white solid, m.p. 87°–89° C., yield 44%.

EXAMPLE 61

3-Fluoro-N-(4-bromo-3-methyl-5-isoxazolyl) benzenesulfonamide

3-Fluoro-N-(4-bromo-3-methyl-5-isoxazolyl)benzenesulfonamide was prepared from 5-amino-4-bromo-3-methylisoxazole and 3-fluorobenzenesulfonyl chloride according to the procedures described in Example 40b. The crude product was purified by recrystallization from ethyl acetate/hexanes to give a light yellow solid, m.p. 125°–128° C., yield 88%.

EXAMPLE 62

2,5-Dimethyl-N-(4-chloro-3-methyl-5-isoxazolyl) benzenesulfonamide 2,5-Dimethyl-N-(4-chloro-3-methyl-5-isoxazolyl)benzenesulfonamide was prepared from 5-amino-4-chloro-3-methylisoxazole and 2,5-dimethylbenzenesulfonyl chloride according to the procedures described in Example 40b. The crude product was purified by recrystallization from ethyl acetate/hexanes to give a light yellow solid, m.p. 92°–93° C., yield 82%.

EXAMPLE 63

4-Acetamido-N-(4-bromo-3-methyl-5-isoxazolyl)bensenesulfonamide

4-Acetamido-N-(4-bromo-3-ethyl-5-isoxazolyl)bensenesulfonamide was prepared from 5-amino-4-bromo-3-methylisoxazole and 4-acetylsulfinilyl chloride according to the procedures described in Example 45. The crude product was purified by recrystallization from ethyl acetate/hexanes to give a crystalline solid, m.p. 208°–210° C., yield 56%.

EXAMPLE 64

4-Nitro-N-(4-bromo-3-methyl-5-isoxazolyl) bensenesulfonamide

4-Nitro-N-(4-bromo-3-methyl-5-isoxazolyl)bensenesulfonamide was prepared from 5-amino-4-bromo-3-methylisoxazole and 4-nitrobenzenesulfonyl chloride according to the procedures described in Example 45. The crude product was purified by recrystallization from ethyl acetate/hexanes to give a crystalline solid, m.p. 146°–149° C., yield 34%.

EXAMPLE 65

4-Butoxy-N-(4-bromo-3-methyl-5-isoxazolyl) bensenesulfonamide

4-Butoxy-N-(4-bromo-3-methyl-5-isoxazolyl)bensenesulfonamide was prepared from 5-amino-4-bromo-3-methylisoxazole and 4-butoxybenzenesulfonyl chloride according to the procedures described in Example 45. The crude product was purified by recrystallization from ethyl acetate/hexanes to give a crystalline solid, m.p. 98°–100° C., yield 33%.

EXAMPLE 66

N-(4-Bromo-3-methyl-5-isoxazolyl)benzo-2,1,3-thiadiazole-4-sulfonamide

N-(4-Bromo-3-methyl-5-isoxazolyl)benzo-2,1,3-thiadiazole-4-sulfonamide was prepared from 5-amino-4-bromo-3-methylisoxazole and 2,1,3-thiadiazole-4-sulfonyl chloride according to the procedures described in Example 45. The crude product was purified by recrystallization from ethyl acetate/hexanes to give a crystalline solid, m.p. 177°–179° C., yield 34%.

EXAMPLE 67

N-(4-Bromo-3-methyl-5-isoxazolyl)-2-thiophenesulfonamide

N-(4-Bromo-3-methyl-5-isoxazolyl)-2-thiophenesulfonamide was prepared from 5-amino-4-bromo-3-methylisoxazole and 2-thiophenesulfonyl chloride according to the procedures described in Example 45. The crude product was purified by recrystallization from ethyl acetate/hexanes to give a crystalline solid, m.p. 125°–127° C., yield 34%.

EXAMPLE 68

3-Chloro-2-methyl-N-(4-Bromo-3-methyl-5-isoxazolyl)benzenesulfonamide

3-Chloro-2-methyl-N-(4-Bromo-3-methyl-5-isoxazolyl)benzenesulfonamide was prepared from 5-amino-4-bromo-3-methylisoxazole and 3-chloro-2-methylbenzenesulfonyl chloride according to the procedures described in Example 45. The crude product was purified by recrystallization from ethyl acetate/hexanes to give a crystalline solid, m.p. 185°–187° C., yield 34%.

EXAMPLE 69

2,4,6-Trimethyl-N-(4-bromo-3-methyl-5-isoxazolyl)benzenesulfonamide 2,4,6-Trimethyl-N-(4-bromo-3-methyl-5-isoxazolyl)benzenesulfonamide was prepared from 5-amino-4-bromo-3-methylisoxazole and 2,4,6-trimethylbenzenesulfonyl chloride according to the procedures described in Example 40b. The crude product was purified by recrystallization from ethyl acetate/hexanes to give a pink solid, m.p. 92°–95° C., yield 64%.

EXAMPLE 70

N-(4-bromo-3-methyl-5-isoxazolyl)-3-toluenesulfonamide

N-(4-bromo-3-methyl.5-isoxazolyl)-3-toluenesulfonamide was prepared from 5-amino-4-bromo-3-methylisoxazole and 3-toluenesulfonyl chloride according to the procedures described in Example 45. The crude product was purified by recrystallization from ethyl acetate/hexanes to give a crystalline solid, m.p. 138°–140° C., yield 63%.

EXAMPLE 71

3-Chloro-2,5-dimethyl-N-(4-bromo-3-methyl-5-isoxazolyl)benzenesulfonamide

3-Chloro-2,5-dimethyl-N-(4-bromo-3-methyl-5-isoxazolyl)benzenesulfonamide was prepared from 5-amino-4-bromo-3-methylisoxazole and 3-chloro-2,5-dimethylbenzenesulfonyl chloride according to the procedures described in Example 45. The crude product was purified by recrystallization from ethyl acetate/hexanes to give a crystalline solid, m.p. 148°–150° C., yield 71%.

EXAMPLE 72

2,5-Difluoro-N-(4-bromo-3-methyl-5-isoxazolyl)benzenesulfonamide 2,5-Difluoro-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 45. The crude product was purified by recrystallization from ethyl acetate/hexanes to give a crystalline solid, m.p. 123°–125° C., yield 62%.

EXAMPLE 73

2,3,4-Trichloro-N-(4-bromo-3-methyl-5-isoxazolyl)benzenesulfonamide 2,3,4-Trichloro-N-(4-bromo-3-methyl-5-isoxazolyl)benzenesulfonamide was prepared from 5-amino-4-bromo-3-methylisoxazole and 2,3,4-trichlorobenzenesulfonyl chloride according to the procedures described in Example 45. The crude product was purified by recrystallization from ethyl acetate/hexanes to give a crystalline solid, m.p. 110°–113° C., yield 66%.

EXAMPLE 74

2,3-Dichloro-N-(4-bromo-3-methyl-5-isoxazolyl)benzenesulfonamide 2,3-Dichloro-N-(4-bromo-3-methyl-5-isoxazolyl)benzenesulfonamide was prepared from 5-amino-4-bromo-3-methylisoxazole and 2,3-dichlorobenzenesulfonyl chloride according to the procedures described in Example 45. The crude product was purified by recrystallization from ethyl acetate/hexanes to give a crystalline solid, m.p. 166°–169° C., yield 75%.

EXAMPLE 75

2,5-Dichloro-N-(4-bromo-3-methyl-5-isoxazolyl)benzenesulfonamide 2,5-Dichloro-N-(4-bromo-3-methyl-5-isoxazolyl)benzenesulfonamide was prepared from 5-amino-4-bromo-3-methylisoxazole and 2,5-dichlorobenzenesulfonyl chloride according to the procedures described in Example 40b. The crude product was purified by recrystallization from ethyl acetate/hexanes to give a yellow powder, m.p. 148°–150° C., yield 53%.

EXAMPLE 76

5-Bromo-2-methoxy-N-(4-bromo-3-methyl-5-isoxazolyl)benzenesulfonamide

5-Bromo-2-methoxy-N-(4-bromo-3-methyl-5-isoxazolyl)benzenesulfonamide was prepared from 5-amino-4-bromo-3-methylisoxazole and 5-bromo- 2-methoxybenzenesulfonyl chloride according to the procedures described in Example 45. The crude product was purified by recrystallization from ethyl acetate/hexanes to give a crystalline solid, m.p. 192°–195° C., yield 61%.

EXAMPLE 77

2-Bromo-N-(4-bromo-3-methyl-5-isoxazolyl)benzenesulfonamide

2-Bromo-N-(4-bromo-3-methyl-5-isoxazolyl)benzenesulfonamide was prepared from 5-amino-4-bromo-3-methylisoxazole and 2-bromobenzenesulfonyl chloride according to the procedures described in Example 45. The crude product was purified by recrystallization from ethyl acetate/hexanes to give a crystalline solid, m.p. 84°–86° C., yield 31%.

EXAMPLE 78

2-Cyano-N-(4-bromo-3-methyl-5-isoxazolyl)benzenesulfonamide

2-Cyano-N-(4-bromo-3-methyl-5-isoxazolyl)benzenesulfonamide was prepared from 5-amino-4-bromo-3-methylisoxazole and 4-chlorobenzenesulfonyl chloride according to the procedures described in Example 45. The crude product was purified by recrystallization from ethyl acetate/hexanes to give a crystalline solid, m.p. 152°–155° C., yield 70%.

EXAMPLE 79

2,4,5-Trichloro-N-(4-bromo-3-methyl-5-isoxazolyl)bensenesulfonamide 2,4,5-Trichloro-N-(4-bromo-3-methyl-5-isoxazolyl)bensenesulfonamide was prepared from 5-amino-4-bromo-3-methylisoxazole and 2,4,5-trichlorobenzenesulfonyl chloride according to the procedures described in Example 45. The crude product was purified by recrystallization from ethyl acetate/hexanes to give a crystalline solid, m.p. 179°–182° C., yield 67%.

EXAMPLE 80

3,4-Dichloro-N-(4-bromo-3-methyl-5-isoxazolyl)benzenesulfonamide 3,4-Dichloro-N-(4-bromo-3-methyl-5-isoxazolyl)benzenesulfonamide was prepared from 5-amino-4-bromo-3-methylisoxazole and 3,4-dichlorobenzenesulfonyl chloride according to the procedures described in Example 45. The crude product was purified by recrystallization from ethyl acetate/hexanes to give a crystalline solid, m.p. 144°–146° C., yield 60%.

EXAMPLE 81

3,4-Dimethoxy-N-(4-bromo-3-methyl-5-isoxazolyl)benzenesulfonamide 3,4-Dimethoxy-N-(4-bromo-3-methyl-5-isoxazolyl)benzenesulfonamide was prepared from 5-amino-4-bromo-3-methylisoxazole and 3,4-dimethoxybenzenesulfonyl chloride according to the procedures described in Example 45. The crude product was purified by recrystallization from ethyl acetate/hexanes to give a crystalline solid, m.p. 136°–138° C., yield 64%.

EXAMPLE 82

2,4-Dichloro-N-(4-bromo-3-methyl-5-isoxazolyl)benzenesulfonamide 2,4-Dichloro-N-(4-bromo-3-methyl-5-isoxazolyl)benzenesulfonamide was prepared from 5-amino-4-bromo-3-methylisoxazole and 2,4-dichlorobenzenesulfonyl chloride according to the procedures described in Example 45. The crude product was purified by recrystallization from ethyl acetate/hexanes to give a crystalline solid, m.p. 138°–141° C., yield 46%.

EXAMPLE 83

N-(4-Iodo-5-methyl-3-isoxazolyl)benzenesulfonamide (a) 3-amino-4-Iodo-5-methylisoxazole 3-Amino-4-iodo-5-methylisoxazole was prepared from 3-amino-5-methylisoxazole and N-iodosuccinimide as described in Example 50a in 46% yield, m.p. 115°–117° C.

(b) N-(4-Iodo-5-methyl-3-isoxazolyl)benzenesulfonamide

N-(4-Iodo-5-methyl-3-isoxazolyl)benzenesulfonamide was prepared from 3-amino-4-iodo-5-methylisoxazole and benzenesulfonyl chloride according to the procedures described in Example 41b. The crude product was purified by recrystallization from ethyl acetate/hexanes to give a brown powder m.p. 138°–141° C., yield 46%.

EXAMPLE 84

4-Nitro-N-(4-bromo-5-methyl-3-isoxazolyl)benzenesulfonamide

4-Nitro-N-(4-bromo-5-methyl-3-isoxazolyl)benzenesulfonamide was prepared from 5-amino-4-bromo-3-methylisoxazole and 4-nitrobenzenesulfonyl chloride according to the procedures described in Example 40b. The crude product was purified by recrystallization from ethyl acetate/hexanes to give a light tan solid, m.p. 1 61°–163° C., yield 55%.

EXAMPLE 85

3-Nitro-N-(4-bromo-5-methyl-3-isoxazolyl) benzenesulfonamide

3-Nitro-N-(4-bromo-5-methyl-3-isoxazolyl)benzenesulfonamide was prepared from 5-amino-4-bromo-3-methylisoxazole and 3-nitrobenzenesulfonyl chloride according to the procedures described in Example 40b. The crude product was purified by recrystallization from ethyl acetate/hexanes, resutling in an off white powder, m.p. 1,37°–139° C., yield 72%.

EXAMPLE 86

4-Trifluoromethyl-N-(4-bromo-3-methyl-5-isoxazolyl)benzenesulfonamide

4-Trifluoromethyl-N-(4-bromo-3-methyl-5-isoxazolyl)benzenesulfonamide was prepared from 5-amino-4-bromo-3-methylisoxazole and 4-trifluoromethylbenzenesulfonyl chloride according to the procedures described in Example 45. The crude product was purified by recrystallization from ethyl acetate/hexanes to give a crystalline solid, m.p. 155°–158° C., yield 72%.

EXAMPLE 87

3-Trifluoromethyl-N-(4-bromo-3-methyl-5-isoxazolyl)benzenesulfonamide

3-Trifluoromethyl-N-(4-bromo-3-methyl-5-isoxazolyl)benzenesulfonamide was prepared from 5-amino-4-bromo-3-methylisoxazole and 3-trifluoromethylbenzenesulfonyl chloride according to the procedures described in Example 45. The crude product was purified by recrystallization from ethyl acetate/hexanes to give a crystalline solid, m.p. 113°–115° C., yield 83%.

EXAMPLE 88

2,5-Dimethoxy-N-(4-bromo-3-methyl-5-isoxazolyl)benzenesulfonamide 2,5-Dimethoxy-N-(4-'bromo-3-methyl-5-isoxazolyl)benzenesulfonamide was prepared from 5-amino-4-bromo-3-methylisoxazole and 2,5-dimethoxybenzenesulfonyl chloride according to the procedures described in Example 45. The crude product was purified by recrystallization from ethyl acetate/hexanes to give a crystalline solid, m.p. 118°–120°, yield 58%.

EXAMPLE 89

N-(3,4-Dimethyl-5-isoxazolyl)-4-biphenylsulfonamide (a) 4-Biphenylsulfonyl chloride 4-Biphenylsulfonic acid (3.0 g, 12.8 mmol) was heated at 70° C. with phosphorus oxychloride (1.30 ml, 14.0 mol) for 2 h. Excess phosphorus oxychloride was removed under reduced pressure. The residue was decomposed with ice water and extracted with ethyl acetate. The extract was washed with 5% sodium bicarboinate solution, dried over anhydrous magnesium sulfate and concentrated to yield 2.9 crude 4-biphenylsulfonyl chloride.

(b) N-(3,4-Dimethyl-5-isoxazolyl)biphenylsulfonamide

The 4-biphenylsulfonyl chloride from step (a) was added to a solution of 5-amino-3,4-dimethylisoxazole (250 mg, 2.2 mmol) and 4-(dimethyl)aminopyridine (5 mg) in dry pyridine (2.0 ml). The reaction mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue that, after purification by column chromatography over silica gel (1% methanol in chloroform as eluent), yielded 337 mg (45%) white solid. Recrystallization from ethyl acetate/hexanes gave white crystals, m.p. 154°–155° C.

EXAMPLE 90

N-(4-Bromo-3-methyl-5-isoxazolyl)-4-biphenylsulfonamide (a) 5-Amino-4-bromo-3-methylisoxazole 5-Amino-3-methylisoxazole (0.98 g, 10 mmol) was dissolved in chloroform (15 ml) and cooled to 0° C. N-Bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product, which was purified by column chromatography using 9: 1, hexanes/ethyl acetate as the eluent, to give 5-amino-4-bromo-3-methylisoxazole (1.55 g, 87% yield).

(b) N-(4-Biphenylsulfonyl)-N-(4-bromo-3-methyl-5-isoxazolyl)-4-biphenylsulfonamide 5-Amino-4-bromo-3-methylisoxazole (0.179 g, 1.0 mmol) was dissolved in dry pyridine (2 ml). 4-Biphenylsulfonyl chloride (0.509 g, 2.2 mmol) was added with stirring at ambient temperature. N,N-Dimethylaminopyridine (5 mg) was added, and stirring was continued at 50° C. for 16 h. The reaction mixture was diluted with dichloromethane (75 ml), washed with 1N HCl (2×50 ml) and the organic phase was dried over magnesium sulfate. The solvent was removed under reduced pressure to yield a crude product, which was purified by column chromatography using 8:2, hexanes/ethyl acetate, to give 0.390 g (60% yield) of N-(4-biphenylsulfonyl)-N-(4-bromo-3-methyl-5-isoxazolyl)-4-biphenylsulfonamide.

(c) N-(4-Bromo-3-methyl-5-isoxazolyl)-4-biphenylsulfonamide

N-(4-biphenylsulfonyl)-N-(4-bromo-3-methyl-5-isoxazolyl)-4-biphenylsulfonamide (0.150 g, 0.233 mmol) was dissolved in tetrahydrofuran (THF). Sodium hydroxide (0.120 g, 3.0 mmol) was added and the solution was warmed to 45° C. to dissolve the sodium hydroxide. Stirring was continued for 20 min. Tetrahydrofuran was removed under reduced pressure. The residue was dissolved in water, cooled to 0° C. and acidified to pH 3–4 with concentrated HCl. The solid precipitate was filtered off and dried in vacuo to give N-(4-bromo- 3-methyl-5-isoxazolyl)-4-biphenylsulfonamide (94% yield), which was further purified by recrystallization from chloroform/hexanes, m.p. 133°–135° C.

EXAMPLE 91

N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared in the same manner as described in Example 90b from 5-amino-4-methyl- 3-trifluoromethylisoxazole and 4-biphenylsulfonyl chloride in 78% yield.

Purification was achieved by recrystallization from methanol/water to give a white solid, m.p. 139°–140° C.

EXAMPLE 92

N-(4-Tridecyl-3-trifluoromethyl-5-isoxazolyl)-4-biphenylsulfonamide

N-(4-Tridecyl-3-trifluoromethyl-5-isoxazolyl)-4-biphenylsulfonamide was prepared, in the same manner as described in Example 90b, from 5-amino-4-tridecyl- 3-trifluoromethyl-isoxazole and 4-biphenylsulfonyl chloride in 81% yield. Purification was achieved by recrystallization from methanol/water to give an off white solid, m.p. 115°–116° C.

EXAMPLE 93

N-(3,4-Dimethyl-5-isoxazolyl)-2-dibenzofuransulfonamide

N-(3,4-Dimethyl-5-isoxazolyl)-2-dibenzofuransulfonamide was prepared, using the method described in Example 89b, from 5-amino-3,4-dimethylisoxazole and 2-benzofuransulfonyl chloride in 32% yield. Purification was achieved by recrystallization from chloroform/hexanes to give a white "cotton-like" solid, m.p. 173°–1750 C. (dec.).

EXAMPLE 94

N-(4-Bromo-5-methyl-3-isoxazolyl)-4-biphenylsulfonamide (a) 3-Amino-4-bromo-5-methylisoxazole 3-Amino-5-methylisoxazole (1.96 g, 20 mmol) was dissolved in chloroform (10 ml) and cooled to 0° C. N-Bromosuccinimide (3.56 g, 20 mmol) was added in small portions over a period of 10 min. The stirring was continued for another 15 minutes at 0° C. The reaction mixture was diluted with chloroform (100 ml), washed with water (2×50 ml) and the organic layer was dried over magnesium sulfate. Removal of the solvent under reduced pressure gave the crude product, which was purified by column chromatography, using 9:1 hexanes/ethyl acetate as the eluent, to give 3-amino-4-bromo-5-methylisoxazole (1.40 g, 40% yield).

(b) N-(4-bromo-5-methyl-3-isoxazolyl)-4-biphenylsulfonamide

N-(4-bromo-5-methyl-3-isoxazolyl)-4-biphenylsulfonamide ws prepared, using the method in Example 89b, from 3-amino-4-bromo-5-methylisoxazole and 4-biphenylsulfonyl chloride in 5% yield. The product (m.p. 154°–156° C.) was isolated in 51% yield by column chromatography, after recrystallization from ethyl acetate/hexanes. N-(4-Biphenylsulfonyl)-N-(4-bromo- 5-methyl-3-isoxazolyl)-4-biphenylsulfonamide was obtained in 51% yield.

EXAMPLE 95

N-(4-Chloro-3-methyl-5-isoxazolyl)-4-biphenylsulfonamide (a) 5-Amino-4-chloro-3-methylisoxazole Using the method in Example 90a, 5-amino-4-chloro-3-methylisoxazole was prepared from 5-amino-3-methylisoxazole and N-chlorosuccinimide in 90% yield.

(b) N-(4-Chloro-3-methyl-5-isoxazolyl)-4-biphenylsulfonamide

Sodium hydride (188 mg, 4.4 mmol) was suspended in dry THF (1 ml) and cooled to 0° C. A solution of 5-amino-4-chloro-3-methylisoxazole (mg, mmol) in dry THF (1 ml) was added with stirring. Once the addition was complete, the reaction mixture was warmed to room temperature for 10 min. The solution was recooled to 0° C., and 4-biphenylsulfonyl chloride (0.283 ml, 2.2 mmol) was added. Stirring was continued at 25° C. for 2 h. Excess sodium hydride was decomposed by the addition of methanol (0.4 ml) followed by water (0.5 ml). THF was removed under reduced pressure and the residue was dissolved in water (20 ml) and basified by addition of sodium hydroxide (pH 9–10). Neutral impurities were removed by extraction with ethyl acetate (2×10 ml). The aqueous layer was acidified to pH 2–3 using concentrated HCl and extracted with ethyl acetate (3×10 ml). The combined organic layer was dried over magnesium sulfate. Removal of the solvent gave N-(4-chloro-3-methyl-5-isoxazolyl)-4-biphenylsulfonamide in 83% yield. This product was purified by recrystallization from ethyl acetate/hexanes as a white solid, m.p. 129°–132° C.

EXAMPLE 96

4-tert-Butyl-N-(3,4-dimethyl-5-isoxazolyl)benzenesulfonamide

4-Tert-butylbenzenesulfonyl chloride (498 mg, 2.14 mmol) and 4-(dimethyl)aminopyridine (5 mg) were added to a solution of 5-amino-3,4-dimethylisoxazole (200 mg, 1.78 mmol) in dry pyridine (2.0 ml). The reaction mixture was stirred at room temperature for 4 h. Pyridine was removed under reduced pressure and the residue was partitioned between water and ethyl acetate. The organic layer was washed with 1N HCl (2×25 ml), brine (25 ml) and dried over anhydrous magnesium sulfate. Evaporation of the solvents left an oily residue which, after purification by column chromatography over silica gel (1% methanol in chloroform as eluent), yielded 320 mg (58%) of an off-white solid. Further purification was achieved by recrystallization from ethyl acetate/hexanes, to yield the pure product as a white solid, m.p. 151°–154° C.

EXAMPLE 97

Alternative procedure (see Example 90) for preparation of N-(4-Bromo-3-methyl-5-isoxazolyl)-4-biphenylsulfonamide (a) N-(4-biphenylsulfonyl)-N-(4-Bromo-3-methyl-5-isoxazolyl)-4-biphenylsulfonamide 5-Amino-4-bromo-3-methylisoxazole (0.179 g, 1.0 mmol) was dissolved in dry pyridine (2 ml). 4-Biphenylsulfonyl chloride (0.509 g, 2.2 mmol) was added with stirring at ambient temperature. N,N-(Dimethyl)aminopyridine (5 mg) was added and stirring was continued at 50° C. for 16 h. The reaction mixture was diluted with dichloromethane (75 ml), washed with 1N HCl (2×50 ml) and the organic phase was dried: over magnesium sulfate. The solvent was removed under reduced pressure to yield a crude product which was purified by column chromatography using 8:2, hexanes/ethyl acetate to give 0.390 g (60% yield) of N-(4-biphenylsulfonyl)-N-(4-Bromo-3-methyl-5-isoxazolyl)- 4-biphenylsulfonamide.

(b) N-(4-Bromo-3-methyl-5-isoxazolyl)-4-biphenylsulfonamide

N-(4-biphenylsulfonyl)-N-(4-Bromo-3-methyl-5-isoxazolyl)-4-biphenylsulfonamide (0.150 g, 0.233 mmol) was dissolved in tetrahydrofuran. Sodium hydroxide (0.120 g, 3.0 mmol) was added and the solution was warmed to 45° C. to dissolve the sodium hydroxide. Stirring was continued for 20 min. Tetrahydrofuran was removed under reduced pressure. The residue was dissolved in water, cooled to 0° C. and acidified to pH 3–4 with concentrated HCl. The solid precipitated was filtered off and dried in vacuo to give N-(4-Bromo- 3-methyl-5-isoxazolyl)-4-biphenylsulfonamide in 94% yield which was further purified by recrystallization from chloroform/hexanes, m.p. 133°–135° C.

EXAMPLE 98

N-(4,5,6,7-Tetrahydro-2,1-benzisoxazol-3-yl) benzenesulfonamide

N-(4,5,6,7-Tetrahydro-2,1-benziosoxazol-3-yl)benzenesulfonamide was prepared in the same manner as described in Example 97 from 3-amino-4,5,6,7-tetrahydro- 2,1-benzisoxazole and benzenesulfonyl chloride in 55% yield. Purification was achieved by recrystallization from ethyl acetate/hexanes to give white crystals, m.p. 155°–157° C.

EXAMPLE 99

N-(3,4-Dimethyl-5-isoxazolyl )-8-quinolinesulfonamide

N-(3,4-Dimethyl-5-isoxazolyl)-8-quinolinesulfonamide was prepared, as described for 4-tert-butyl-N-(3,4-dimethyl-5-isoxazolyl)benzenesulfonamide (Example 96), in 61% yield. Purification was achieved by column chromatography and recrystallization from ethyl acetate/hexanes to give a white crystalline solid, m.p. 176°–178° C.

EXAMPLE 100

N-(4-Bromo-3-methyl-5-isoxazolyl)- 8-quinolinesulfonamide

N-(4-Bromo-3-methyl-5-isoxazolyl)-8-quinolinesulfonamide was prepared, in the same manner as described in Example 96, from 5-amino-4-bromo-3-methylisoxazole and 8-quinolinesulfonyl chloride in 62% yield. Purification was achieved by recrystallization from ethyl acetate/hexanes to give a crystalline solid, m.p. 169°–171° C.

EXAMPLE 101

N-(3,4-Dimethyl-5-isoxazolyl)-(–)- 10-camphorsulfonamide

This compound was prepared according to the method in Example 96 in 49% yield as a white solid after column chromatography and recrystallization from ethyl acetate/hexanes, m.p. 135°–137° C.

EXAMPLE 102

N-(3,4-Dimethyl-5-isoxazolyl)-(+)- 10-camphorsulfonamide

This compound was prepared according to the method in Example 96 in % yield as a white solid after column chromatography and recrystallization from ethyl acetate/hexanes, m.p. 137°–139° C.

EXAMPLE 103

N-(3,4-Dimethyl-5-isoxazolyl)methanesulfonamide

This compound was prepared according to the method in Example 96 in 90% yield as a solid after column chromatography which was further purified by recrystallization from ethyl acetate/hexanes to give colorless crystals, m.p. 125°–127° C.

EXAMPLE 104

N-(3,4-Dimethyl-5-isoxazolyl)- trans-styrenesulfonamide

This compound was prepared according to the method in Example 96 in yield as a colorless crystalline solid after column chromatography and recrystallization from ethyl acetate/hexanes, m.p. 125°–128° C.

EXAMPLE 105

2-Nitro-N-(3,4-dimethyl-5-isoxazolyl)- β-trans-styrenesulfonamide

This compound was prepared according to the method in Example 96 in 59% yield from 2-nitro-trans-β-styrenesulfonyl chloride [see, e.g., Bordwell et al. (1946) *J. Am, Chem. Soc.* 68;1778 for a process for nitrogenetion of styrenesulfonyl chloride] and 5-amino-3,4-dimethylisoxazole as a colorless solid after column chromatography and recrystallization from ethyl acetate/hexanes, m.p, 108.5°–111° C.

EXAMPLE 106

N-(5-Methyl-3-isoxazolyl)benzenesulfonamide

3-Amino-5-methylisoxazole (0.196 g, 2.0 mmol) was dissolved in dry pyridine (3 ml). Benzenesulfonyl chloride (0.352 g, 2.0 mmol) was added and the resultant solution stirred at room temperature for 16 h. Pyridine was removed under reduced pressure. The residue was dissolved in dichloromethane (75 ml) and washed with 1N HCl (2×50 ml). The organic layer was dried over anhydrous magnesium sulfate and the solvent was removed under reduced pressure to give N-(5-methy-3-isoxazolyl)benzene-sulfonamide (0.40 g, 84% yield). The product was purified by recrystallization using ethyl acetate/hexanes to give a white solid, m.p. 107°–8° C.

EXAMPLE 107

4-Benzylamino-N-(3,4-dimethyl-5-isoxazolyl) benzenesulfonamide

To a mixture of 4-amino-N-(3,4-dimethyl-5-isoxazolyl)benzenesulfonamide (1.0 g, 3.74 mmol) and sodium bicarbonate (310 mg, 4.48 mmol) suspended in ethanol was added benzyl bromide (770 mg, 4.48 mmol). After 10 min of stirring at 70° C., the mixture became homogeneous. The reaction was stirred at 70° C. for 2 h and the solvent and volatiles were evaporated under reduced pressure. The residue was dissolved in ethyl acetate and washed with brine (2×25 ml). After drying over magnesium sulfate, evaporation of the solvent left a viscous yellow oil which was chromatographed on silica gel to give 960 mg (72% yield) clear, colorless oil. Further purification by HPLC gave a white solid, m.p. 47°–8° C.

EXAMPLE 108

4-(Dimethylamino)-N-(3,4-dimethyl-5-isoxazolyl) benzenesulfonamide

A solution containing 4-amino-N-(3,4-dimethyl-5-isoxazolyl)benzenesulfonamide (1.0 g, 3.74 mmol), formic acid (1.1 g, 22.4 mmol) and a 37% solution of formaldehyde (0.65 ml, 8.97 mmol) were heated at 40° C. under an argon atmosphere for 5 h. The light red solution was cooled and neutralized with saturated sodium bicarbonate solution and extracted into ethyl acetate (3×40 ml). The organic layer was then washed with brine (2×20 ml) and dried over magnesium sulfate. Evaporation of the solvent under reduced pressure and column chromatography over silica gel yielded 562 mg (25%) of a white solid, m.p. 152°–154° C.

EXAMPLE 109

4-(Ethylamino)-N-(3,4-dimethyl-5-isoxazolyl) benzenesulfonamide

Sodium borohydride (71 mg, 3.74 mmol) was added to a solution of acetic acid (740 mg, 12 mmol) in dry benzene (5 ml) with the temperature being kept at 20° C. When the evolution of hydrogen gas had ceased (ca. 5 min), 4-amino-N-(3,4-dimethyl-5-isoxazolyl)benzenesulfonamide (0.5 g, 1.87 mmol) was added in one lot and the reaction mixture was refluxed for 3 h. The reaction was cooled and shaken with saturated sodium bicarbonate solution. The organic layer was then washed with brine (2×20 ml), dried over magnesium sulfate and evaporated. the crude product was purified by column chromatography on silica gel using 1% methanol in chloroform as eluent to give 103 mg (19%) of a colorless oil. Further purification by HPLC gave a white solid, m.p. 123° C.

EXAMPLE 110

4-(Phenylethynyl)-N-(3,4-dimethyl-5-isoxazolyl) benzenesulfonamide

To a mixture of phenylacetylene (34.8 ml, 0.32 mmol) and copper(I) iodide (0.25 mg) in diethylamine (2 ml) stirred at room temperature was added 4-iodo-N-(3,4-dimethyl-5-isoxazolyl)benzenesulfonamide (1 00 mg, 0.26 mmol) and bis(triphenylphosphine) palladium(II) chloride (1.86 mg). The brown mixture was stirred at room temperature for 4 h. The solvent was removed under reduced pressure and the brownish residue was extracted into 50 ml of ethyl acetate. The organic extract was washed with 1N HCl (2×20 ml) and brine (25 ml). After drying with magnesium sulfate, the solvent was removed to give a brown crystalline solid which was chromatographed on silica gel with 1.5% methanol in chloroform to give 150 mg (81%) brown solid. Recrystallization from ethyl acetate/hexanes gave a white powder, m.p. 198°–200° C. (dec.).

EXAMPLE 111

4-[N '-(Ethoxycarbonylmethyl)ureido]-N-(3,4-dimethyl-5-isoxazolyl)benzenesulfonamide 4-amino-N-(3,4-dimethyl-5-isoxazolyl)benzenesulfonamide (545 mg, 2.0 mmol) was dissolved in dry dimethylformamide (10 ml). Ethyl isocyanatoacetate (463 ml, 4.0 mmol) was added. The reaction was stirred at room temperature for 3 h and then heated at 80° C. for an additional 8 h. Dimethylformamide was removed under reduced pressure and the residue was recrystallized from acetonitrile/water to give 807 mg (90% yield) brownish solid, m.p. 115°–125° C.

EXAMPLE 112

4-(N'-Cyclohexylureido)-N-(3,4-dimethyl-5-isoxazolyl)benzene sulfonamide

This compound was prepared from 4-amino-N-( 3,4-dimethyl-5-isoxazolyl)benzene-sulfonamide and cyclohexyl isocyanate according to the method in Example 110 in 75% crude yield. Further purification was achieved by preparative HPLC (76% recovery), furnishing the pure product as a white solid, m.p. 190°–195° C.

EXAMPLE 113

4-(Dibenzosuberylamino)-N-(3,4-dimethyl-5-isoxazolyl)benzenesulfonamide

Dibenzosuberyl chloride (953 mg, 4.0 mmol) and 4-amino-N-(3,4-dimethyl- 5-isoxazolyl)benzenesulfonamide (545 mg, 2.0 mmol) were dissolved in dry tetrahydrofuran (15 ml) and triethylamine (0.56 ml, 2.0 mmol) was slowly added. The reaction was stirred at room temperature for 2 h. The solvent and volatiles were removed under reduced pressure. The residue was taken up in ethyl acetate, washed with 1N HCl and dried over anhydrous magnesium sulfate. After removal of solvent, the residue was recrystallized from methanol to give 610 mg (66%) of yellow solid, m.p. 184° C.

EXAMPLE 114

4-(2,4-Dinitrophenylamino)-N-(3,4-dimethyl-5-isoxazolyl)benzenesulfonamide 2,4-Dinitrofluorobenzene (0.457 ml, 3.6 mmol) and 4-amino-N-(3,4-dimethyl- 5-isoxazolyl)benzenesulfonamide (818 mg, 3.0 mmol) were dissolved in dry tetrahydrofuran (25 ml) and triethylamine (1.0 ml, 7.5 mmol) was added slowly. The reaction was stirred at room temperature for 48 h. The solvent and volatiles were removed under reduced pressure and the residue was partitioned between 1N HCl and ethyl acetate. The organic layer was dried over anhydrous magnesium sulfate and concentrated and the residue was recrystallized from methanol to give 1.1 g (85%) yellow solid, m.p. 187° C.

EXAMPLE 115

4-[(2,4-Diaminophenyl)amino]-N-(3,4-dimethyl-5-isoxazolyl)benzenesulfonamide 4-(2,4-Dinitrophenylaimino)-N-( 3,4-dimethyl-5-isoxazolyl)benzenesulfonamide (95 mg, 0.219 mmol) was dissolved with heating in 60 ml of methanol. 10% Palladium of charcoal (8 mg) was added and the mixture was hydrogenated at ambient temperature and pressure for 30 min. The catalyst was removed by filtration through Celite®and the filtrate was concentrated. The product was purified by preparative HPLC to give 22 mg (27%) white solid, m.p. 181°–183° C.

EXAMPLE 116

N-[3-Methyl-4-(4-methoxyphenoxy)-5-isoxazolyl] benzenesulfonamide (a) 5-Amino-4-bromo-3-methylisoxazole 5-Amino-3-methylisoxazole (0.98 g, 10 mmol) was dissolved in chloroform (15 ml) and cooled to 0° C. N-bromosuccinimide (1.78 g, 10 mmoles) was added in small portions over a period of 10 min. The stirring was continued for another 10 minutes at 0° C. The reaction mixture was diluted with chloroform (50 ml), washed with water (2×50 ml) and the organic layer was dried over magnesium sulfate. Removal of the solvent under reduced pressure gave the crude product which was purified by column chromatography using 9:1, hexanes/ethyl acetate as eluent to give 5-amino-4-bromo-3-methylisoxazole (1.55 g, 87% yield).

(b) 5-Amino-4-(4-methoxyphenoxy)-3-methylisoxazole

To a mixture of sodium hydride (60% dispersion in mineral oil, 52 mg, 1.3 mmol) in dry dimethylformamide (2.0 ml) was added 4-methoxyphenol (0.15 g, 1.2 mmol). After stirring the solution at room temperature of 10 min, 5-amino- 4-bromo-3-methylisoxazole (0.20 g, 1.1 mmol) was added, followed by bis(triphenylphosphine)palladium(11) chloride (79 mg, 0.11 mmol). The mixture was heated to 50° C. for 2.5 h and then cooled to room temperature. The dark brown reaction mixture was worked up with ethyl acetate and 5% NaOH. The organic layer was dried with magnesium sulfate, filtered and concentrated under reduced pressure. The residue was chromatographed on silica gel using 20% ethyl acetate in hexanes as eluent to give 0.13 g (51% yield) of 5-amino-4-(4-methoxyphenoxy)-3-methylisoxazole.

(c) N-[3-M ethyl-4-(4-methoxyphenoxy)-5-isoxazolyl] benzenesulfonamide

This compound was prepared according to the method in Example 90 from benzenesulfonyl chloride and 5-amino-4-(4-methoxyphenyl)-3-methylisoxazole in 94% yield. A colorless solid was obtained after column chromatography and recrystallization from chloroform/hexanes, m.p. 128°–130° C.

EXAMPLE 117

N-(4-Ethyl-3-trifluoromethyl-5-isoxazolyl) benzenesulfonamide

N-(4-Ethyl-3-trifluoromethyl-5-isoxazolyl)benzenesulfonamide was prepared, using the method of Example 90, from 5-amino-4-ethyl-3-trifluoromethylisoxazole and benzenesulfonyl chloride in 72% yield. Purification was achieved by recrystallization from ethyl acetate/hexanes to give white needles, m.p. 105°–106° C.

EXAMPLE 118

N-(4-Methyl-3-trifluoromethyl-5-isoxazolyl)-1-naphthalenesulfonamide

N-(4-Methyl-3-trifluoromethyl-5-isoxazolyl)-1-naphthalenesulfonamide was prepared, as described in Example 90, from 5-amino- 4-methyl-3-trifluoromethylisoxazole and 1-naphthalenesulfonyl chloride in 85% yield. Purification was achieved by recrystallization from methanol/water to give white needed, m.p. 154°–155° C.

EXAMPLE 119

N-(4-Ethyl-3-trifluoromethyl-5-isoxazolyl)-1-naphthalenesulfonamide

N-(4-Ethyl-3-trifluoromethyl-5-isoxazolyl)-1-naphthalenesulfonamide was prepared, as described in Example 90, from 5-amino-4-ethyl-3-trifluoromethylisoxazole and 1-naphthalenesulfonyl chloride in 70% yield. Purification was achieved by recrystallization from methanol/water to give an off white solid, m.p. 135°–137° C.

EXAMPLE 120

N-(4-Methyl-3-trifluoromethyl-5-isoxazolyl)-4-biphenylsulfonamide

N-(4-Methyl-3-trifluoromethyl-5-isoxazolyl)-4-biphenylsulfonamide was prepared, as described in Example 90, from 5-amino-4-methyl-3-trifluoromethylisoxazole and 4-biphenylsulfonyl chloride in 78% yield. Purification was achieved by recrystallization from ethyl acetate/hexanes to give a white solid, m.p. 139°–140° C.

EXAMPLE 121

N-(4-Hexyl-3-trifluoromethyl-5-isoxazolyl) benzenesulfonamide

N-(4-Hexyl-3-trifluoromethyl-5-isoxazolyl)benzenesulfonamide was prepared as described in Example 42 from 5-amino-4-hexyl-3-trifluoromethylisoxazole and benzenesulfonyl chloride in 80% yield. Purification was achieved by recrystallizing the crude product from methanol/water to give a white needles, m.p. 128.5°–129° C.

EXAMPLE 122

N-(4-Nonyl-3-trifluoromethyl-5-isoxazolyl) benzenesulfonamide

N-(4-Nonyl-3-trifluoromethyl-5-isoxazolyl)benzenesulfonamide was prepared as described in Example 42 from 5-amino-4-nonyl-3-methylisoxazole and benzenesulfonyl chloride in 87% yield. Purification was achieved by recrystallizing the crude product from methanol/water to give a yellow solid, m.p. 101.5° C.

EXAMPLE 123

N-(4-Tridecyl-3-trifluoromethyl-5-isoxazolyl) benzenesulfonamide

N-(4-Tridecyl-3-trifluoromethyl-5-isoxazolyl)benzenesulfonamide was prepared as described in Example 42 from 5-amino-4-tridecyl-3-methylisoxazole and benzenesulfonyl chloride in 80% yield. Purification was achieved by recrystallizing the crude product from methanol/water to give a yellow solid, m.p. 89° C.

EXAMPLE 124

N-(3-Cyclopropyl-4-methyl-5-isoxazolyl) benzenesulfonamide

This compound was prepared as described in Example 42 from 5-amino- 3-cyclopropyl-4-methylisoxazole and benzenesulfonyl chloride in 62% yield. The crude product was preparative HPLC to give a viscous colorless oil.

EXAMPLE 125

N-(4-Methyl-3-trifluoromethyl-5-isoxazolyl) benzenesulfonamide

This compound was prepared according to the method in Example 96 from benzenesulfonyl chloride and 5-amino-4-methyl-3-trifluoromethylisoxazole (see, U.S. Pat. No. 4,910,326 or corresponding EP A 0220947) in 72% yield as an off white solid after recrystallization from ethyl acetate/hexanes, m.p. 99.5°–100° C.

EXAMPLE 126

N-(4-Ethyl-3-trifluoromethyl-5-isoxazolyl) benzenesulfonamide

N-(4-Ethyl-3-trifluoromethyl-5-isoxazolyl)benzenesulfonamide was prepared in the same manner as described in Example 42 from 5-amino-4-ethyl- 3-trifluoromethylisoxazole and benzenesulfonyl chloride in 72% yield. Purification was achieved by recrystallization from ethyl acetate/hexanes to give white needles, m.p. 105°–106.5° C.

EXAMPLE 127

N-(3-Ethyl-4-methyl-5-isoxazolyl)benzenesulfonamide

N-(3-Ethyl-4-methyl-5-isoxazolyl)benzenesulfonamide was prepared as described in Example 42 from 5-amino-3-ethyl-4-methylisoxazole and benzenesulfonyl chloride in 68% yield. Purification was achieved by preparative HPLC to give a white solid, m.p. 94°–95° C.

EXAMPLE 128

2-Phenyl-N-(4-bromo-3-methyl-5-isoxazolyl)-3-thiophenesulfonamide.

A. 3-Bromo-2-phenyl-thiophene

Tetrakis (triphenylphosphine) palladium (400 mg), $Na_2CO_3$ (4M, 80 ml, 320 mmol) and phenylboric acid (3.81 g, 30.3 mmol) as a solution in ethanol (80 ml) were sequentially added to a solution of 2,3-dibromothiophene (7.33 g, 30.3 mmol) in benzene (100 ml). The mixture was heated at reflux for 12 hours. The aqueous layer of the crude mixture was removed and the organic layer was diluted with $Et_2O$ (200 ml), washed with 1N NaOH (2×150 ml) and was dried ($MgSO_2$), filtered and the soluent was evaporated. The residue was chromatographed using hexane as the eluent to give 3-bromo-2-phenylthiophene as a clear oil (3.31 g, 47% yield).

B. 2-Phenylthiophene-3-sulfonylchloride nBuLi (2.38M, 11.5 ml, 27.28 mmol) was slowly added to a solution of 2-phenyl-thiophene (22.73 mmol) in ether (50 ml) at 0° C. The reaction was stirred at 0° C. for 1 h. $SO_2$ was bubbled through the mixture for 15 minutes at 0° C. followed by the addition of NCS (3.95 g, 29.55 mmol) as a suspension in THF (20 ml).

The crude products were purified by column chromatography (hexanes) to give 2-phenylthiophene-3-sulfonylchloride as a white solid (1.23 g, 34% yield).

C. 2-Phenyl-N-(4-bromo-3-methyl-5-isoxazolyl)-3-thiophenesulfonamide,

2-Phenyl-N-(4-bromo-3-methyl-5-isoxazolyl)-3-thiophenesulfonamide was prepared from 2-phenyl-3-thiophene sulfonylchloride using the method described in Example 1.

The product was purified by HPLC, 77% yield, reddish solid, 86 mp –89° C.

EXAMPLE 129

N-(4-bromo-3-methyl-5-isoxazolyl)-2-pyridine sulfonamide

N-(4-bromo-3-methyl-5-isoxazolyl)-2-pyridine sulfonamide was prepard from pyridine-2-sulfonyl chloride and 5-amino-4-bromo-3-methylisoxazole using the method of Example 1. (NaH/THF). Recrystallized from MeOH gave a solid, 66% yield, with amp of 184°–189° C.

EXAMPLE 130

3-Phenoxy-N-(4-bromo-3-methyl-5-isoxazolyl)thiophene-2-sulfonamide

A. 3-Phenoxythiophene.

Couprous chloride (3.08 g, 31.1 mmol) and phenol (8.78 g, 93.3 mmol) were sequentially added to a solution of 3-bromothiophene (5.06 g, 31.1 mmol) in pyridine (150 ml). Sodium hydride (3.73 g, 93.3 mmol, 60% dispersion in mineral oil) was then slowly added. The reaction was heated at reflux for 20 hours under Argon. The pyridine was removed under reduced pressure. The residue was diluted with EtO (200 ml) and washed with 1N NaOH (3×100 ml), 1N HCl (2×150 ml) and 1N NaOH (150 ml). The organic layer was dried ($MgSO_4$), filtered, and the solvent was evaporated. The residue was chromatographed using hexanes to give 3-phenoxy-thiophene as a clear oil (4.0 g, 74% yield).

B. 3-Phenoxythiophene-2-sulfonyl chloride

BuLl (2.38M, 11.5 ml, 27.28 mmol) was slowly added to a solution of 3-phenoxythiophene (4.0 g, 22.73 mmol) in ether (50 ml) at 0° C. The reaction was stirred at 0° C. for 1 h. $SO_2$ was bubbled through the mixture for 15 minutes at 0° C. followed by the addition of NCS (3.95 g, 29.55 mmol) as a suspension in THF (20 ml). The mixture was allowed to warm up to 250° C. and stirred at for 2 more hours. The precipitate was filtered, and the filtrate was concentrated and chromatographed (hexanes) to give 3-phenoxythiophene-2-sulfonyl chloride as a yellowish solid (1.03 g, 17% yield).

C. N-(4-bromo-3-methyl-5-isoxazolyl)-3-phenoxythiophene-2-sulfonamide

N-(4-bromo-3-methyl-5-isoxazolyl)-3-phenoxythiophene-2-sulfonamide was prepared from 3-phenoxythiophene-2-sulfonyl chloride aand 5-amino-4-bromo-3-methylisoxazole using the method described in Example 1. The product was recrystallized from acetonitrile/$H_2O$ to give a solid m.p. 121°–123° C., 61% yield.

EXAMPLE 131

3-Phenylaminocarbonyl-N-(3,4-dimethyl-5-isoxazolyl)-pyridine-2-sulfonamide nBuLi (1.8 ml, 2.34M) was slowly added to a solution of N-(3,4-dimethyl- 5-isoxazolyl)pyridine-2-sulfonamide (500 mg, 2.0 mmol) in THF (14 ml) at –78° C. The mixture was stirred at –78° C. for 1 hour. Phenylisocyanate (3.55 mg, 2.9 mmol) was then added slowly and the mixture was allowed to warm room temperature. The reaction was quenched with $H_2O$ and the volatiles were removed under reduced pressure. The aqueous residue was extracted with EtOAc (2×50 ml). The aqueous layer was acidified with concenrated HCl to pH 4(~50 ml) and extracted with EtOH (2×50 ml). The combined organic layer was dried (MgSO$_4$), filtered and evaporated to give a yellow oil, which was purified by HPLC to give an 88% yield with a m.p. of 199°–200° C.

EXAMPLE 132

N-(4-Bromo-3-methyl-5-isoxazolyl)-2-[N-(4-isopropylphenyl)aminocarbonyl]thiophene-3-sulfonamide N-(4-Bromo-3-methyl-5-isoxazolyl)-2-[N-(4-isopropylphenyl)aminocarbonyl]thiophene-3-sulfonamide was prepared in the same manner as described in Example 24 from N-(4-Bromo- 3-methyl-5-isoxazolyl)-2-(carboxyl)thiophene- 3-sulfonamide and 4-isopropylaniline in 19% yield. The crude product was passed through silica gel column using ethyl acetate as eluent. This was further purified by HPLC (5% CH$_3$CN to 100% CH$_3$CN over 30 min.) to give a solid.

EXAMPLE 133

N-(4-Bromo-3-methyl-5-isoxazolyl)-2-[N-(4-sec-butylphenyl)aminocarbonyl]thiophene-3-sulfonamide N-(4-Bromo-3-methyl-5-isoxazolyl)-2-[N-(4-sec-butylphenyl)aminocarbonyl]thiophene-3-sulfonamide was prepared in the same manner as described in Example 24 from N-(4-bromo-3-methyl-5-isoxazolyl)- 2-(carboxyl)thiophene-3-sulfonamide and 4-sec-butylaniline in 25% yield. The crude product was passed through silica gel column using ethyl acetate as eluent. This was further purified by HPLC (5% CH$_3$CN to 100% CH$_3$CN over 30 min.) give a solid, m.p. 205°–208° C.

EXAMPLE 134

N-(4-Bromo-3-methyl-5-isoxazolyl)-2-[N-(4-tert-butylphenyl)aminocarbonyl]thiophene-3-sulfonamide N-(4-Bromo-3-methyl-5-isoxazolyl)-2-[N-(4-tert-butylphenyl)aminocarbonyl]thiophene-3-sulfonamide was prepared in the same manner as described in Example 24 from N-(4-Bromo-3-methyl- 5-isoxazolyl)-2-(carboxyl)thiophene-3-sulfonamide and 4-tert-butylaniline in 28% yield. The crude product was passed through silica gel column using ethyl acetate as eluent. This was further purified by HPLC (5% CH$_3$CN to 100% CH$_3$CN over 30 min.) give a solid, m.p. 76°–86° C.

EXAMPLE 135

N-(4-Bromo-3-methyl-5-isoxazolyl)-2-[N-(4-butylphenyl)aminocarbonyl]thiophene-3-sulfonamide N-(4-Bromo-3-methyl-5-isoxazolyl)-2-[N-( 4-butylphenyl)aminocarbonyl]-thiophene- 3-sulfonamide was prepared in the same manner as described in Example 24 from N-(4-Bromo-3-methyl- 5-isoxazolyl)-2-(carboxyl)thiophene-3-sulfonamide and 4-butylaniline in 18% yield. The crude product was passed through silica gel column using ethyl acetate as eluent. This was further Purified by HPLC (5% CH$_3$CN to 100% CH$_3$CN over 30 min.) give a solid.

EXAMPLE 136

N-(4-bromo-3-methyl-5-isoxazolyl)-2-biphenylsulfonamide

A. 2-Biphenylsulfonyl chloride

2-Bromobiphenyl (2.33 g, 10 mmol) was dissolved in ether (10 ml) and cooled to −78° C. n-Butyllithium (2.5M solution in hexane, 4.8 ml, 12 mmol) was added dropwise under constant stirring and argon atmosphere. The resultant reaction mixture was stirred at −70° C. to −60° C. for 1 h. The reaction mixture was cooled to −78° C. and sulfuryl chloride (0.88 ml, 11 mmol) was added dropwise. After addition, the reaction mixture was allowed to attain ambient temperature slowly and stirred for 1 h. The reaction mixture was diluted with ethyl acetate (50 ml), washed with water and the organic layer dried over anhydrous MgSO$_4$. Removal of the solvent under reduced pressure gave a crude product, which was purified by column chromatography, using hexane followed by 5% ethyl acetate in hexane as a eluent, to give 2-biphenylsulfonyl chloride as a solid (1.3 g, 51% yield).

B. N-(4-bromo-3-methyl-5-isoxazolyl)-2-biphenylsulfonamide

N-(4-bromo-3-methyl-5-isoxazolyl)-2-biphenylsulfonamide was prepared in the same manner as described in Example 2 from 5-amino-4-bromo-3-methylisoxazole and 2-biphenylsulfonyl chloride in 71% yield. Purification was achieved by recrystallization from ethyl acetate/hexanes to give a crystalline solid, m.p. 145°–147° C.

EXAMPLE 137

N-(4-Chloro-3-methyl-5-isoxazolyl)-2-biphenylsulfonamide

N-(4-Chloro-3-methyl-5-isoxazolyl)-2-biphenylsulfonamide was prepared in the same manner as described in Example 2 from 5-amino-4-chloro-3-methylisoxazole and 2-biphenylsulfonyl chloride in 74% yield. Purification was achieved by recrystallization from ethyl acetate/hexanes to give a crystalline solid, m.p. 132°–134° C.

EXAMPLE 138

N-(4-Bromo-3-methyl-5-isoxazolyl)-3-biphenylsulfonamide

A. 3-Biphenylsulfonyl chloride

3-Bromobiphenyl (1.5 g, 6.4 mmol) was dissolved in ether (15 ml) and cooled to −78° C. t-Butyllithium (1.7M solution in hexane, 3.8 ml, 6.4 mmol) was added dropwise under constant stirring and an argon atmosphere. The resultant reaction mixture was stirred at −10° C. to −5° C. for 6 h. The reaction mixture was cooled to −78° C. and sulfuryl chloride (0.64 ml, 6.4 mmol) was added dropwise. After the completion of the addition, the reaction mixture was allowed to attain ambient temperature slowly and stirred for 1 h. The reaction mixture was diluted with ethyl acetate (50 ml), washed with water and the organic layer dried over anhydrous MgSO$_4$. Removal of the solvent under reduced pressure gave crude product, which was purified by column chromatography, using hexane followed by 5% ethyl acetate in hexane as eluent, to give 3-biphenylsulfonyl chloride as a oil (0.8 g, 49% yield).

B. N-(4-bromo-3-methyl-5-isoxazolyl)-3-biphenylsulfonamide

N-(4-bromo-3-methyl-5-isoxazolyl)-3-biphenylsulfonamide was prepared in the same manner as described in Example 2 from 5-amino-4-bromo-3-methylisoxazole and 3-biphenylsulfonyl chloride in 22% yield. This was purified by HPLC (5% CH₃CN to 100% CH₃CN over 30 min.) to give a solid., m.p. 78°–82° C.

EXAMPLE 139

N-(4-chloro-3-methyl-5-isoxazolyl)-3-biphenylsulfonamide

N-(4-chloro-3-methyl-5-isoxazolyl)-3-1-phenylsulfonamide was prepared in the same manner as described in Example 2 from 5-amino-4-chloro-3-methylisoxazole and 3-biphenylsulfonyl chloride in 63% yield. This was purified by HPLC (5% CH₃CN to 100% CH₃CN over 30 min.) to give a solid, m.p. 84°–86° C.

EXAMPLE 140

N-(4-bromo-3-methyl-5-isoxazolyl)thiazole-2-sulfonamide

A. Thiazole-2-sulfonyl chloride

Thiazole (0.51 g, 6 mmol) was dissolved in THF (5 ml) and cooled to −78° C. under argon atmosphere. n-Butyllithium (2.5M solution in hexane, 2.4 ml, 6 mmol) was added dropwise under constant stirring. The resultant reaction mixture was stirred at −78° C. for 40 min. Sulfur dioxide was bubbled through the reaction mixture for 15 min at −78° C. The reaction mixture was allowed to attain ambient temperature slowly and stirred for 30 min. NCS was added and stirring was continued for 30 min. The reaction mixture was diluted with water (50 ml), extracted with ethyl acetate (2×50 ml) and the combined organic layer was dried over anhydrous MgSO₄. Removal of the solvent under reduced pressure gave crude product which was purified by column chromatography, using hexane as eluent, to give thiazole-2-sulfonyl chloride as a liquid (0.6 g, 54% yield).

B. N-(4-bromo-3-methyl-5-isoxazolyl)thiazole-2-sulfonamide

N-(4-bromo-3-methyl-5-isoxazolyl)thiazole-2-sulfonamide was prepared in the same manner as described in Example 2 from 5-amino-4-bromo-3-methylisoxazole and thiazole-2-sulfonyl chloride in 57% yield. This was purified by HPLC (5% CH₃CN to 100,% CH₃CN over 30 min.) to give a solid., m.p. 175°–177° C.

EXAMPLE 141

N-(4-chloro-3-methyl-5-isoxazolyl)thiazole-2-sulfonamide

N-(4-chloro-3-methyl-5-isoxazolyl)thiazole-2-sulfonamide was prepared in the same manner as described in Example 2 from 5-amino-4-chloro-3-methylisoxazole and thiazole-2-sulfonyl chloride in 33% yield. This was purified by HPLC (5% CH₃CN to 100% CH₃CN over 30 min.) to give a solid, m.p. 171°–173° C.

EXAMPLE 142

N-(3,4-dimethyl-5-isoxazolyl)thiazole-2-sulfonamide

N-(3,4-methyl-5-isoxazolyl)thioazole-2-sulfonamide was prepared in the same manner as described in Example 14 from 5-amino-3,4-dimethylisoxazole and thiazole-2-sulfonyl chloride in 37% yield. This was purified by HPLC (5% CH₃CN to 100% CH₃CN over 30 min.) give a solid, m.p. 118°–120° C.

EXAMPLE 143

2-benzyl-N-(4-bromo-3-methyl-5-isoxazolyl)-thiophene-5-sulfonamide

A. 1-(2-Thienyl)benzyl alcohol

Sodium borohydride (0.37 g, 10 mmol) was added to 2-benzylthiophene (1.88 g, 10 mmol) dissolved in methanol/THF mixture (1:10 ratio, 11 ml). This was stirred at room temperature for 10 h. The reaction mixture was decomposed by addition of saturated ammonium chloride solution (50 ml) and was extracted with ethyl acetate (2×50 ml). The combined organic layer was dried over anhydrous MgSO₄. Removal of the solvent gave 1-(2-thienyl)benzyl alcohol as a solid (1.75 g, 92% yield).

B. 2-Benzylthiophene

Acetic anhydride (5 ml) was added to a solution of 1-(2-thienyl)benzyl alcohol in pyridine. The resultant solution was stirred at 70° C. for 3 h. Water (50 ml) was added and the reaction mixture was stirred at room temperature for 2 h. This was extracted with ethyl acetate (2×50 ml) and the combined organic layer dried over anhydrous MgSO₄. Removal of the solvent gave crude product, which was purified by passing through silica gel using 3:1 hexane/ethyl acetate mixture to give 1-(2-thienyl)benzyl acetate.

A solution of 1-(2-thienyl)benzyl acetate in THF (5 ml) was added carefully to dry liquid ammonia (100 ml). Lithium metal was added in small portions until the blue color persisted. The resulting reaction mixture was stirred for 30 min, and the reaction was quenched by addition of solid ammonium chloride. The residue, after complete evaporation of liquid ammonia, was dissolved in water (50 ml) and was extracted with methylene chloride (2×50 ml). The combined organic layer was dried over MgSO₄ and filtered. Removal of the solvent gave crude product, which was purified by column chromatography using hexane as eluent to give 2-benzylthiophene (1.2 g, 68% yield).

C. 5-Benzylthiophene-2-sulfonyl chloride

To a solution of 2-benzylthiophene (0.875 g, 5 mmol) in chloroform (2 ml) at 0° C. was added chlorosulfonic acid dropwise and the reaction was stirred at 0° C. for 30 min. The reaction mixture was decomposed by pouring onto crushed ice (20 g). The mixture was extracted with ethyl acetate, dried over MgSO₄ and filtered. The solvent was removed under reduced pressure to give 5-benzylthiophene-2-sulfonic acid.

Phosphorous pentachloride (2.08 g, 40 mmol) was added to a solution of 5-benzylthiophene-2-sulfonic acid in phosphorous oxychloride (6.0 g, 40 mmol) at 0° C. The reaction mixture was kept at 50° C. for 1 h, cooled to room temperature, then poured onto crushed ice (50 g) and extracted with ethyl acetate (2×30 ml). Removal of the solvent under reduced pressure gave a crude product, which was purified by column chromatography using 3% ethyl acetate in hexane to give 2-benzylthiophene-5-sulfonyl chloride (0.6 g, 39% yield).

D. 5-Benzyl-N-(4-Bromo-3-methyl-5-isoxazolyl)thiophene-2-sulfonamide

5-Benzyl-N-(4-Bromo-3-methyl-5-isoxazolyl)thiophene-2-sulfonamide was prepared in the same manner as described in Example 2 from 5-amino-4-bromo- 3-methylisoxazole and 5-benzyl-2-thiophenesulfonyl chloride in 22% yield. The product was purified by HPLC (5% CH₃CN to 100% CH₃CN over 30 min.) to give a solid, m.p. 49°–50° C.

EXAMPLE 144

3-phenethyl-N-(4-bromo-3-methyl-5-isoxazolyl)thiophene-2-sulfonamide

A. 1-(3-Thienyl)phenethyl alcohol

Benzyl bromide (25.65 g, 150 mmol) was added dropwise over 8 h to a suspension of magnesium (3.6 g, 150 mmol) in ether (75 ml) dissolved in ether (30 ml). The resulting mixture was cooled to −10° C. 3-thiophenecarboxaldehyde in ether (45 ml) over 30 min was then added and the resultant reaction mixture was stirred at room temperature for 6 h. This was cooled to 0° C. and the reaction mixture was decomposed by addition of 0.1N HCl. The ether layer was separated and the aqueous phase was extracted with ethyl acetate (2×50 ml). The combined organic layer was dried over MgSO₄ and filtered. Removal of the solvent gave 1-(3-thienyl)phenethyl alcohol (16 g, 78% yield).

B. 1-(3-Thienyl)phenethyl acetate 1-(3-Thienyl)phenethyl alcohol (10 g, 49 mmol) was dissolved in a 2:1 pyridine and acetic anhydride mixture (50 ml). This was stirred at 80° C. for 4 h. Excess of pyridine and acetic anhydride mixture was removed under reduced pressure and the residue was dissolved in water (100 ml). This was extracted with methylene chloride (3×75 ml) and the combined organic layer was dried over MgSO₄ and filtered. Removal of the solvent gave 1-(3-thienyl)phenethyl acetate (10.2 g, 84% yield).

C. 3-Phenethylthiophene 1-(3-thienyl)phenethyl acetate dissolved in THF (20 ml) was added carefully to dry liquid ammonia (300 ml). Lithium metal was added in small portions until the blue color persisted. The resulting reaction mixture was stirred for 30 min and the reaction was quenched by addition of solid ammonium chloride. The residue, after the complete evaporation of liquid ammonia, was dissolved in water (100 ml) and was extracted with methylene chloride (4×50 ml). The combined organic layer was dried over MgSO₄ and filtered. Removal of the solvent gave a crude product, which was purified by column chromatography using hexane followed by mixture of ethyl acetate in hexane as eluent to give 3-phenethylthiophene (3.2 g, 34% yield) and 1-(3-thienyl)phenethyl acetate (starting material, 7 g).

D. 3-Phenethylthiophene-2-sulfonyl chloride and 4-phenethylthiophene-2-sulfonyl chloride 3-Phenethylthiophene (0.94 g, 5 mmol) was dissolved in THF (12 ml) and cooled to −78° C. under argon atmosphere. n-Butyllithium (2.5M solution in hexane, 4.4 ml, 5.5 mmol) was added dropwise with constant stirring under an argon atmosphere. The resultant reaction mixture was stirred at −10° C. to 0° C. for 3 h, cooled to −78° C. and sulfur dioxide was bubbled through the reaction mixture for 15 min. The reaction mixture was allowed to attain ambient temperature slowly and stirring continued for 30 min. NCS (1 g) was added and stirring was continued for 1 h. The reaction mixture was diluted with water (50 ml), extracted with methylene chloride (2×50 ml) and the combined organic layer was dried over anhydrous MgSO₄. Removal of the solvent under reduced pressure gave a crude product which was purified by column chromatography, using 0.2% ethyl acetate in hexane as eluent, to give 3-phenethyl-2-thiophenesulfonyl chloride (0.06 g, 4% yield) and 4-phenethyl-2-thiophenesulfonyl chloride (0.72 g, 45% yield).

E. 3-Phenethyl-N-(4-bromo-3-methyl-5-isoxazolyl)thiophene-2-sulfonamide

3-Phenethyl-N-(4-bromo-3-methyl-5-isoxazolyl)thiophene-2-sulfonamide was prepared in the same manner as described in Example 2 from 5-amino-4-bromo-3-methylisoxazole and 3-phenethyl-2-thiophenesulfonyl chloride in 48% yield. This was purified by HPLC (5% CH₃CN to 100% CH₃CN over 30 min.) to give a solid.

EXAMPLE 145

4-phenethyl-N-(4-bromo-3-methyl-5-isoxazolyl)thiophene-2-sulfonamide 4-phenethyl-N-(4-bromo-3-methyl-5-isoxazolyl)thiophene-2-sulfonamide was prepared in the same manner as described in Example 2 from 5-amino-4-bromo-3-methylisoxazole and 4-phenethyl-2-thiophenesulfonyl chloride in 32% yield. This was purified by HPLC (5% CH₃CN to 100% CH₃CN over 30 min.) to give a gum.

EXAMPLE 146

N-(4-Bromo-3-methyl-5-isoxazolyl)-5-(3-methoxyphenyl)thiophene-2-sulfonamide A. 5-Bromothiophene-2-sulfonyl chloride Chlorosulfonic acid was added dropwise over 20 min. to a cold solution (−78° C.) of 2-bromothiophene (16.3 g, 100 mmol) in methylene chloride (50 ml) was added After addition of chlorosulfonic acid was complete, the cold bath was removed. The reaction mixture was allowed to attain room temperature slowly (2 h), was added dropwise onto the crushed ice (1000 g) and was extracted with methylene chloride (4×100 ml). The combined organic layer was dried over MgSO₄, filtered and the solvent was removed under reduced pressure to give a crude product. This was purified by column chromatography using hexane as eluent to give 5-bromothiophene-2-sulfonyl chloride (22 g, 75% yield).

B. N-(5-Bromothiophene-2-sulfonyl)pyrrole

N-(5-Bromothiophene-2-sulfonyl)pyrrole was prepared in the same manner as described in Example 33A from 5-Bromothiophene-2-sulfonyl chloride and pyrrole in 88% yield. This was purified by recrystallization using hexane/ethyl acetate as a solvent.

C. 3-Methoxyphenylboric acid

3-Methoxyphenylboric acid was prepared in the same manner as described in Example 33B from 3-bromoanisole and triisopropyl borate in 82% yield. This was used in the next step without any further purification.

D. N-[5-(3-methoxyphenyl)thiophene-2-sulfonyl]pyrrole

N-[5-(3-methoxyphenyl)thiophene-2-sulfonyl]pyrrole was prepared in the same manner as described in Example 32C from 3-methoxyphenylboric acid and N-(5-bromothiophene-2-sulfonyl)pyrrole in 93% yield. This was purified by recrystallization using hexane/ethyl acetate as solvent.

E. 5-(3-Methoxyphenyl)thiophene-2-sulfonyl chloride

To the suspension of N-[5-(3-methoxyphenyl)thiophene-2-sulfonyl]pyrrole (1.4 g, 4.5 mmol) in ethanol (15 ml) was added 6N sodium hydroxide solution (15 ml) and the resultant reaction mixture refluxed for 14 h. The reaction mixture was cooled to room temperature. Ethanol was removed under reduced pressure and the resultant precipitate was filtered and dried under vacuum (1.1 g, 91% yield).

Phosphorous pentachloride (2.08 g, 10 mmol) was added to the suspension of sodium slat of sulfonic acid (0.62 g, 2.5 mmol) (obtained from above step) in phosphorousoxy chloride (0.93 ml, 10 mmol) and the resultant reaction mixture stirred at room temperature for 3 h. This was decomposed by adding on to crushed ice and the product was extracted with methylene chloride (2×50 ml). The combined organic layer dried over MgSO$_4$ and filtered. Removal of the solvent gave the crude product which was purified by column chromatography using 2% ethyl acetate in hexane to give 5-(3-methoxyphenyl)thiophene- 2-sulfonyl chloride (0.51 g, 75%).

EXAMPLE 147

N-(4-Bromo-3-methyl-5-isoxazolyl )-5-(3-methoxyphenyl)thiophene-2-sulfonamide

N-(4-Bromo-3-methyl-5-isoxazolyl)-5-(3-methoxyphenyl)thiophene-2-sulfonamide was prepared in the same manner as described in Example 2 from 5-amino-4-bromo-3-methylisoxazole and 5-(3-methoxyphenyl)thiophene-2-sulfonyl chloride in 48% yield. This was purified by HPLC (5% CH$_3$CN to 100% CH$_3$CN over 30 min.) give a solid.

EXAMPLE 148

N-(4-Bromo-3-methyl-5-isoxazolyl )-5-(4-methoxyphenyl)thiophene-2-sulfonamide

A. 4-Methoxyphenylboric acid

4-Methoxyphenylboric acid was prepared in the same manner as described in Example 33B from 4-bromoanisole and triisopropyl borate in 69% yield. This was used in the next step without any further purification.

B. N-[5-(4-methoxyphenyl)thiophene-2-sulfonyl]pyrrole

N-[E-(4-methoxyphenyl)thiophene-2-sulfonyl]pyrrole was prepared in the same manner as described in Example 32C from 4-methoxyphenylboric acid and N-(5-Bromothiophene-2-sulfonyl)pyrrole in quantative yield. This was purified by recrystallization using hexane/ethyl acetate as a solvent.

C. 5-(4-Methoxyphenyl)thiophene-2-sulfonyl chloride 5-(4-Methoxyphenyl)thiophene-2-sulfonyl chloride was prepared in the same manner as described in Example 146E from N-[5-( 4-methoxyphenyl)thiophene-2-sulfonyl]pyrrole in 77% yield.

EXAMPLE 149

1,2-trans-dimethylstyrene(3,4-dimethyl-5-isoxazolyl)-2-sulfonamide 1,2-trans-dimethylstyrene(3,4-dimethyl-5-isoxazolyl)-2-sulfonamide was prepared by the method of Example 14 with 3,4-dimethyl-5-amino isoxazole (0.209 g, 1.87 mmol) and trans-1,2-dimethylstyrene-2-sulfonyl chloride. Flash chromatography (30% Etoac/hexane) and recrystallization from CHCl$_3$/hexane provided 79 mg (14% yield) of light yellow crystals, m.p. 164°–166° C.

EXAMPLE 150

N-(4-Bromo-3-methyl-5-isoxazolyl)-5-(3-thienyl) thiophene-2-sulfonamide

A. 3-Thiopheneboric acid

To a solution of 3-bromothiophene (8.15 g, 50 mmol) in THF (20 ml) at −78° C. under an argon atmosphere was added n-butyllithium (2.5M solution in hexane, 20 ml, 50 mmol) dropwise and the resultant solution was stirred at −78° C. for 45 min. This solution was added to a solution of triisopropyl borate (9.4 g, 50 mmol) in THF at −78° C. over 30 min through a steel cannula. The resultant reaction mixture was stirred at room temperature for 12 h and was decomposed by the addition of 100 ml 1N HCl. The aqueous layer was extracted with ether (2×100 ml) and the combined organic layer was extracted with 1M NaOH (3×30 ml), the aqueous extract was acidified with concentrated HCl to pH 2 and extracted with ether (3×50 ml). The combined ether extract was washed once with water, dried over MgSO$_4$ and filtered. Removal of the solvent gave 3-thenylboronic acid as a solid (5.2 g, 80% yield).

B. N-[5-(3-thienyl)thiophene-2-sulfonyl]pyrrole

N-[5-(3-thienyl)thiophene-2-sulfonyl]pyrrole was prepared in the same manner as described in Example 32C from 3-thienylboric acid and N-( 5-bromothiophene-2-sulfonyl)pyrrole in quantative yield. This was purified by recrystallization using hexane/ethyl acetate as solvent.

C. 5-(3-Thienyl)thiophene-2-sulfonyl chloride 5-(3-thienyl)thiophene-2-sulfonyl chloride was prepared in the same manner as described in Example 146E from N-[5-( 4-methoxyphenyl)thiophene-2-sulfonyl]pyrrole in 74% yield.

D. N-(4-Bromo-3-methyl-5-isoxazolyl)-5-(3-thienyl)thiophene-2-sulfonamide

N-(4-Bromo-3-methyl-5-isoxazolyl)-5-(3-thienyl)thiophene-2-sulfonamide was prepared in the same manner as described in Example 2 from 5-amino-4-bromo- 3-methylisoxazole and 5-(3-thienyl)thiophene-2-sulfonyl chloride in 40% yield. This was purified by HPLC (5% CH$_3$CN to 100% CH$_3$CN over 30 min.) give a solid.

EXAMPLE 151

1,2-cis-Dimethylstyrene(3,4-dimethyl-5-isoxazolyl)-2-sulfonamide

A. cis and trans-1,2-dimethylstyrene-2-sulfonyl chloride

Cis and trans 2-bromo-1,2-dimethylstyrene (2.61 g, 12.4 mmol) was added to a mixture of magnesium (0.90 g, 37.1 mmol) in dry ether (40 ml). The reaction mixture was stirred 18 hours at ambient temperature and then sulfurdioxide was flushed into the reaction flask. The ether was removed by distillation and the resulting brown residue was stirred in 40 ml of CH$_2$Cl$_2$, followed by the addition of NCS (1.82 g, 13.6 mmol). The reaction mixture was stirred 1 hr at ambient temperature then diluted with stone (100 ml) and washed with brine (2×100 ml). The organic was dried (MgSO$_4$), filtered and concentrated. Flash chromatography (5% EtOAc/hexanes) provided 0.269 g (9% yield) of the cis-isomer and 0.563 g (20% yield) of the trans-isomer.

B. 1,2-cis-dimethylstyrene(3,4-dimethyl-5-isoxazolyl)-2-sulfonamide 1,2-cis-dimethylstyrene(3,4-dimethyl-5-isoxazolyl)-2-sulfonamide was prepared by the method of Example 14 with 3,4-dimethyl-5-aminoisoxazole (0.105 g, 0.94 mmol)

and cis-1,2-dimethylstyrene-2-sulfonyl chloride (0.26 g, 1.13 mmol). Flash chromatography (30% EtOAc/hexane) and recrystallization from CHCl₃/hexane provided 37 mg of white crystals (13% yield), m.p. 122.5°–124° C.

EXAMPLE 152

1-phenylstyrene(3,4-dimethyl-5-isoxazolyl)-2-sulfonamide

A. 1,1-diphenylethene-2-sulfonyl chloride 1,1-Diphenylethene (11.3 mmol, 2 ml) was added to a solution of DMF (22.7 mmol, 1.75 ml) and sulfuryl chloride (19.3 mmol, 1.55 ml) at 0° C. The reaction was heated to 90° C. for 4 hr, then cooled to ambient temperature and poured into ice (500 ml). The aqueous layer was extracted with EtOAc (2×100 ml). Then the organic was dried (MgSO₄) filtered and concentrated. Flash chromatography (5% EtOAc/hexane) provided 0.92 g (29% yield) of light yellow crystals.

B. 1-phenylstyrene(3,4-dimethyl-5-isoxazolyl)-2-sulfonamide 1-phenylstyrene(3,4-dimethyl-5-isoxazolyl)-2-sulfonamide was prepared by the method of Example 14 with 3,4-dimethyl-5-aminoisoxazole (0.168 g, 1.5 mmol) and 1,1-diphenylethene-2-sulfonyl chloride (0.502 g, 1.8 mmol). Flash chromatography (30% EtOAc/hexane) provided 133 g of light tan crystals, m.p. 159.5°–161° C.N-(4-bromo-3-methyl-5-isoxazolyl)-2,5-dimethylfuran-3-sulfonamide.

EXAMPLE 153

A. 2,5-Dimethylfuran-3-sulfonyl chloride

DMF (2.2 ml, 28 mmol) and sulfuryl chloride (1.9 ml, 24 mmol) were stirred at 0° C. for 30 minutes and then the 2,5-dimethylfuran (1.5 ml, 14 mmol) was slowly added. The reaction mixture was heated to 60° C. for 30 minutes, then cooled to ambient temperature and poured into ice water (200 ml). The aqueous layer was extracted with EtOAc (100 ml) and then the organic layer was dried (MgSO₄) filtered and concentrated to collect 0.69 g of a brown liquid. Flash chromatography (5% EtOAc/hexane) provided 0.607 g (22% yield) of a yellow liquid.

B. Furan-2-sulfonyl chloride

Furan-2-sulfonyl chloride was prepared by the method of Example 1 with 4-bromo-3-methyl-2-aminoisoxazole (0.354 g, 2.0 mmol), NaH (60% oil dispersion) (200 g, 5.0 mmol) and 2,5-dimethylfuran 3-sulfonyl chloride (0.467 g, 2.4 mmol). Flash chromatography (5% CH₃OH/CHCl₃) and recrystallization from CHCl₃/hexane provided 0.21 4 g (32% yield) of light brown crystals (m.p. 85.5°–87° C.).

C. N-(4-bromo-3-methyl-5-isoxazolylfuran-2-sulfonamide

N-(4-bromo-3-methyl-5-isoxazolylfuran-2-sulfonamide was prepared by the method of Example 1 with 4-bromo-3-methyl-2-amino isoxazole (0.266 g, 1.5 mmol), NaH (60% oil dispersion) (0.15 g, 3.8 mmol) and furan-2-sulfonyl chloride (0.30 g, 1.8 mmol). Flash chromatography (50% EtOAc/hexane) and recrystallization from CHCl₃ and hexane provided 90 g (20% yield) of light yellow crystals (m.p. 117°–119° C.).

EXAMPLE 154

N-(4-bromo-3-methyl-5-isoxazolyl)-5-(phenylthio)furan-2-sulfonamide

A. 2-phenylthiofuran t-BuLi (1.7 m, 10 ml, 1.7 mmol) was added to a solution of furan (1.24 ml, 17 mmol) in 20 ml of THF at −60° C. Thirty minutes later diphenyldisulfide (3.7 g, 17 mmol) was added via cannula in 8 ml of THF. The reaction was warmed to ambient temperature for 30 minutes, then diluted with 150 ml of ether and washed with 3% NaOH (3×100 ml). The organic was dried (MgSO₄), filtered and concentrated to collect 2.92 g (97% yield) of a light yellow liquid.

B. 5-phenylthiofuran-2-sulfonyl chloride 5-phenylthiofuran-2-sulfonyl chloride was prepared by the method of Example 34A with 5-phenylthiofuran (1.5 g, 8.5 mmol), t-BuLi (1.2 m, 8.9 mmol, 5.3 ml) and NCS (1.14 g, 8.5 mmol). Flash chromatography (5% EtOAc/hexane) provided 1.61 g (69% yield) of a yellow-orange liquid.

C. N-(4-bromo-3-methyl-5-isoxazolyl)-5-(phenylthio)furan-2-sulfonamide

N-(4-bromo-3-methyl-5-isoxazolyl)-5-(phenylthio)furan-2-sulfonamide was prepared by the method of Example 1 with 4-bromo-3-methyl-2-aminoisoxazole (0.354 g, 2.0 mmol), NaH (60% oil dispersion) (0.20 g, 5.0 mmol) and 5-phenylthiofuran-2-sulfonyl chloride (0.66 g, 2.4 mmol). Flash chromatography (50% EtOAc/hexane) and recrystallization from CHCl₃/hexane provided 82 mg (10% yield) of a tan solid (m.p. 90°–91.5° C.).

EXAMPLE 155

N-(4-bromo-3-methyl-5-isoxazolyl)-5-phenylfuran-2-sulfonamide

A. 2-phenylfuran 2-phenylfuran was prepared by the method of Example 32C from 2-bromofuran (0.93 g, 6.3 mmol), sodium carbonate (18 ml of 2M aqueous solution), phenyl boric acid (0.93 g, 7.6 mmol) and tetrakis (triphenylphosphine) palladium (0) (0.36 g, 0.32 mmol). Flash chromatography with hexane provided 0.79 g (87% yield) of a colorless liquid.

B. 5-phenylfuran-2-sulfonyl chloride 5-phenylfuran-2-sulfonyl chloride was prepared by the method of Example 34A with 2-phenylfuran (0.79 g, 5.5 mmol), t-BuLi (1.7 m, 6.0 mmol, 3.6 ml) and NCS (0.73 g, 5.5 mmol). Flash chromatography (5% EtOAc/hexane) provided 0.84 g (63% yield) of a light red solid.

C. N-(4-bromo-3-methyl-5-isoxazolyl)-5-phenylfuran-2-sulfonamide

N-(4-bromo-3-methyl-5-isoxazolyl)-5-phenylfuran-2-sulfonamide was prepared by the method of Example 1 with 4-bromo-3-methyl-2-amino isoxazole (0.354 g, 2.0 mmol), NaH (60% oil dispersion) (0.20 g, 5.0 mmol) and 5-phenylfuran-2-sulfonyl chloride (0.58 g, 2.4 mmol). Flash chromatography (50% EtOAc/hexane) and recrystallization from CHCl₃/hexane provided 0.23 g (29% yield) of light yellow crystals (m.p. 124°–126° C.).

EXAMPLE 156

N-(4-bromo-3-methyl-5-isoxazolyl)-5-(4-isopropylphenyl)thiophene-2-sulfonamide

A. 4-Isopropylphenyl boronic acid

4-Isopropylphenyl boronic acid was prepared in the same manner as described in Example 33B from 1-bromo-4-ethyl benzene. The boronic acid was isolated as a white powder in 63% yield, m.p. 133°–135° C.

B. N-(pyrrole)-5-(4-isopropylphenyl)thiophene-2-sulfonamide

N-(pyrrole)-5-(4-isopropylphenyl)thiophene-2-sulfonamide was prepared in the same manner as described in Example 33C, from 4-isopropylphenyl boronic acid and N-(5-bromothiophene sulfonyl)-pyrrole. Purification by column chromatography using 10% ethyl acetate/hexanes gave the pure sulfonamide as an off white colored solid in 84% yield, m.p. 112°–114° C.

C. 5-chlorosulfonyl-2-(4-ethylphenyl)thiophene 5-chlorosulfonyl-2-(4-ethylphenyl)thiophene was prepared in the same manner as described in Example 33D. Hydrolysis of 526 mg (1.59 mmol) of N-(pyrrole)-5-(4-isopropylthiophene)-2-sulfonamide with 6N sodium hydroxide followed by chlorination using phosphorous-oxychloride and phosphorous pentachloride gave the crude sulfonyl chloride as dark oil. Flash column chromatography over silica gel using 2% ethyl acetate/hexanes yielded 262 mg (55%) of the pure sulphonyl chloride as a light brown oil.

D. N-(4-bromo-3-methyl-5-isoxazolyl)-5-(4-isopropylphenyl)thiophene- 2-sulfonamide N-(4-bromo-3-methyl-5-isoxazolyl)-5-( 4-isopropylphenyl)thiophene-2-sulfonamide was prepared in the same manner as described in Example Z. Reaction of 5-chlorosulfonyl-2-(4-isopropyl)thiophene (260 mg, 0.87 mmol) with 5-amino-4-bromo-3-methylisoxazole (161 mg, 0.91 mmol) yielded after flash chromatography using 10% NeoH/CACl$_3$ a pale brown solid (265 mg) which was further purified using preparative HPLC to give the pure sulfonamide as a light tan colored solid, m.p. 114°–116° C.

EXAMPLE 157

N-(4-bromo-3-methyl-5-isoxazolyl)-5-(4-propylphenyl)thiophene-2-sulfonamide

A. 1-bromo-4-propylbenzene

A solution of 1-bromopropane (1.32 g, 0.6 mmol) was added dropwise at room temperature at a rate such that a gentle reflux was maintained to a suspension of magnesium (258 mg, 12 mmol) in dry tetrahydrofuran. The cloudy suspension was stored at room temperature for an additional 30 minutes to produce a gray solution that was then added dropwise over 15 minutes to a mixture of 1-iodo-4-bromobenzene (3.0 g, 10.6 mmol) and tetrakis (triphenylphosphine) palladium (0) in 50 mL of dry benzene at room temperature. The mixture was stirred for 2 hours, diluted with 50 mL of water, the organic layer was separated and the aqueous layer was extracted with ether (2×50 mL). The combined organic extracts were dried and evaporated to yield 1.69 g (80%) of a light brown oil, and used in the next step without further purification.

B. 4-propylphenyl boronic acid

To a suspension of magnesium shavings (217 mg, 8.9 mmol) in 3 mL of dry tetrahydrofuran under argon, a crystal along with a solution of 4-bromopropylbenzene (1.69 g, 8.5 mmol) dissolved in 6 mL of tetrahydrofuran was added at such a rate that a gentle reflux was maintained. The solution was refluxed for an additional 0.5 h, cooled to room temperature and added in portions over 10 minutes to a solution of trimethylborate (924 mg, 8.9 mmol) previously dissolved in 4 mL of dry ether at −78° C. After 30 minutes, the solution was warmed to room temperature where stirring continued for 90 minutes, then the reaction was quenched by the addition of 2 mL of a 10% hydrochloric acid solution. The tetrahydrofuran was removed under reduced pressure and the remaining residue was extracted into diethyl ether (3×25 mL). The combined ether extracts was extracted with 1M NaOH (3×25 mL) and the resulting aqueous layer was acidified to pH 2.0 using 6N HCl, then reextracted back into diethyl ether (3×25 mL). The combined organic layers was washed with water (1×25 mL), brine (1×25 mL) and dried over magnesium sulfate. Evaporation of solvent left a brown solid which was filtered through a small plug of silica gel using 11.0 MeOH/CACl3. Evaporation left 448 mg (32%) of a brown solid, m.p. 90°–93° C.

C. N-(pyrrole)-5-(4-propylphenyl)thiophene-2-sulfonamide

N-(pyrrole)-5-(4-propylphenyl)thiophene-2-sulfonamide was prepared in the same manner as described in Example 33C, from 4-dropylphenyl boronic acid and N-(5-bromothiophenesulfonyl)pyrrole. Purification by column chromatography using 10% ethyl acetate/hexanes gave the pure sulfonamide as a white solid in 55% yield, m.p. 106°–108° C.

D. 5-chlorosulfonyl-2-(4-propylphenyl)thiophene 5-chlorosulfonyl-2-(4-propylphenyl)thiophene was prepared in the same manner as described in Example 33D. Hydrolysis of 240 mg (0.73 mmol) of N-(pyrrole)-5-(4-propylphenylthiophene)-2-sulfonamide with 6N NaOH followed by chlorination using phosphorous oxychloride and phosphorous pentachloride gave the crude sulfonyl chloride as a greenish-brown oil. Flash chromatography over silica gel using 2% ethyl acetate/hexanes yielded 83 mg (81%) of the pure sulfonyl chloride as a pale yellow oil.

E. N-(4-bromo-3-methyl-5-isoxazolyl)-5-( 4-propylphenyl)-thiophene-2-sulfonamide N-(4-bromo-3-methyl-5-isoxazolyl)-5-(4-propylphenyl)-thiophene-2-sulfonamide was prepared in the same manner as described in Example 2. Reaction of 5-chlorosulfonyl-2-(4-isopropyl)thiophene (260 mg, 0,87 mmol) with 5-amino-4-bromo-3-methylisoxazole (161 mg, 0.91 mmol) yielded after flash chromatography using 10% MeOH/CHCl$_3$ a brown solid (76.1 mg) which was further purified using preparative HPLC to give the pure sulfonamide as a tan colored oil.

EXAMPLE 158

Assays for identifying compounds that exhibit endothelin antagonistic and/or agonist activity Compounds that are potential endothelin antagonists are identified by testing their ability to compete with $^{125}$I-labeled ET-1 for binding to human ET$_A$ receptors or ET$_B$ receptors present on isolated cell membranes. The effectiveness of the test compound as an antagonist or agonist of the biological tissue response of endothelin/can also be assessed by measuring the effect on endothelin induced contraction of isolated rat thoracic aortic rings. The ability of the compounds to act as antagonists or agonists for ET$_B$ receptors can be assess by testing the ability of the compounds are to inhibit endothelin-1 induced prostacyclin release from cultured bovine aortic endothelial cells.

A. Endothelin binding inhibition—Binding Test #1: Inhibition of binding to ET$_A$ receptors TE 671 cells (ATCC Accession No. HTB 139) express ET$_A$ receptors. These cells were grown to confluence in T-175 flasks. Cells from multiple flasks were collected by scraping, pooled and centrifuged for 10 min at 190 X g. The cells were resuspended in phosphate buffered saline (PBS) containing 10 mM EDTA using a Tenbroeck homogenizer. The suspension was centrifuged at 4° C. at 57,800 X g for 15 min, the pellet was resuspended in 5 ml of buffer A (5 mM HEPES buffer, pH 7.4 containing aprotinin (100 KIU/ml)) and then frozen and thawed once. 5 ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800 X g as described above, the pellet washed twice with buffer A and then resuspended in buffer C (30 mM HEPES buffer, pH 7.4 containing aprotinin (100 KIU/ml) to give a final protein concentration of 2 mg/ml and stored at −70° C. until use.

The membrane suspension was diluted with binding buffer (30 mM HEPES buffer, pH 7.4 containing 150 mM NaCl, 5mM $MgCl_2$, 0.5% Bacitracin) to a concentration of 8 µg/50 µl. $^{125}$I-endothelin-1 (3,000 cpm, 50 mL) was added to 50 µL of either: (A) endothelin-1 (for non specific binding) to give a final concentration 80 nM); (B) binding buffer (for total binding); or (C) a test compound (final concentration 1 nM to 100 µM). The membrane suspension (50 µL), containing up to 8 pg of membrane protein, was added to each of (A), (B), or (C). Mixtures were shaken, and incubated at 4° C. for 16–18 hours, and then centrifuged at 4° C. for 25 min at 2,500 X g. The supernatant, containing unbound radioactivity, was decanted and the pellet counted on a Genesys multiwell gamma counter. The degree of inhibition of binding (D) was calculated according to the following equation:

$$\%D = 100 - \frac{(C) - (A)}{(B) - (A)} \times 100$$

Each test was generally performed in triplicate.

B. Endothelin binding inhibition—Binding Test #2: Inhibition of binding to $ET_B$ receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µl.

Briefly, the COS7 cells, described above, that had been transfected with DNA encoding the $ET_B$ receptor and express the human $ET_B$ receptor on their surfaces, were grown to confluence in T-175 flasks. Cells from multiple flasks were collected by scraping, pooled and centrifuged for 10 min at 190 X g. The cells were resuspended in phosphate buffered saline (PBS) containing 10 mM EDTA using a Tenbroeck homogenizer. The suspension was centrifuged at 4° C. at 57,800 X g for 15 min, the pellet was resuspended in 5 ml of buffer A (5 mM HEPES buffer, pH 7.4 containing aprotinin (100 KIU/ml)) and then frozen and thawed once. Five ml of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800 X g as described above, the pellet washed twice with buffer A and then resuspended in buffer C (30 mM HEPES buffer, pH 7.4 containing aprotinin (100 KIU/ml) to give a final protein concentration of 2 mg/ml. The binding assay was performed as described above (A) using the membrane preparation diluted to give 1 µg/50 µl of binding buffer.

C. Test for activity against endothelin-induced contraction of isolated rat thoracic aortic rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223°–230) or by measuring the ability to contract the tissue when added alone.

Compounds to be tested are prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 ml organ bath filled with Krebs'-Henseleit solution saturated with a gas mixture of 95% $O_2$ and 5% $CO_2$ (118 mM NaCl, 4,7 mM KCl, 1.2 mM $MgSO_4$, 1.2 mM $KH_2PO_4$, 25 mM $NaHCO_3$, 2.5 mM $CaCl_2$, 10 mM D-glucose) gassed with 95% $O_2$/5% $CO_2$. Changes in tension are measured isometrically and recorded using a Grass Polygraph coupled to a force transducer. Endothelin is added to the organ bath in a cumulatively increasing manner, and the effects of the test compounds on the concentration-response curve for endothelin-1 are examined. Compounds are added 15 min prior to the addition of endothelin-1.

D. Assay for identifying compounds that have agonist and/or antagonistic activity against $ET_B$ receptors 1. Stimulation of prostacyclin release Since endothelin-1 stimulates the release of prostacyclin from cultured bovine aortic endothelial cells, the compounds that have agonist or antagnoist activity are identified by their ability to inhibit endothelin-1 induced prostacyclin release from such endothelial cells by measuring 6-keto $PGF_{1\alpha}$ substantially as described by (Filep et al. (19.91) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and sub-cultured at least four times, The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of sarafotoxin 6c induced contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 ml organ bath filled with Krebs'-Henseleit solution containing 10 µM cyclo(D-Asp-Pro-D-Val-Leu-D-Trp) (BQ-123; see, U.S. Pat. No. 5,114,918 to Ishikawa et al.), 5 µM indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6c. The effects of the test compounds on the concentration-response curve for sarafotoxin 6c are examined.

E. Results

The $IC_{50}$ for each of the compounds of the preceding Examples for $ET_A$ and $ET_B$ receptors has been measured. Almost all of the compounds have an $IC_{50}$ of less than 10 μM for either or both of the $ET_A$ and $ET_B$ receptors. Many of the compounds have an $IC_{50}$ less than about 10 μM, others have an $IC_{50}$ less than about 1 μM and some of the compounds have an $IC_{50}$ less than about 0.1 μM. A number of the compounds have an $IC_{50}$ for $ET_A$ receptors that is substantially less (10 to 100-fold or more) than for $ET_B$ receptors, and, thus are selective for ETA receptors. Others of the compounds are $ET_B$ selective.

Since modifications will be apparent to those of skill in this art, it is intended that this invention be limited only by the scope of the appended claims.

We claim:

1. A compound of formula I:

$$Ar^2-SO_2-N(H)-\underset{R^1}{\overset{R^2}{\bigg|}}\text{(isoxazole)} \quad (I)$$

or $$Ar^2-SO_2-N(H)-\underset{R^1}{\overset{R^2}{\bigg|}}\text{(isoxazole isomer)}$$

wherein: $R^1$ and $R^2$ are either (i), (ii) or (iii) as follows:

(i) $R^1$ and $R^2$ are independently selected from H, $NH_2$, $NO_2$, halide, pseudohalide, alkyl, alkenyl, alkynyl, aryl, arylalkyl, heterolaryl, alkoxy, alkylamino, hydroxyalkyl, alkoxyalkyl, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, with the proviso that $R^2$ is not halide or pseudohalide; or, (ii) $R^1$ and $R^2$ together form $-(CH_2)_n-$, where n is 3 to 6; or, (iii) $R^1$ and $R^2$ together form 1,3-butadienyl; and $Ar^2$ is a heterocycle containing up to about 16 carbons in the ring, except that $Ar^2$ is not naphthyl unless the compound is an N-isoxazolylsulfonamide substituted at the 4-position on the isoxazolyl group with halide or higher alkyl that contains from 8 to 15 carbon atoms and is a straight or branched chain.

2. The compounds of claim 1, wherein: $Ar^2$ selected from:

[Structures of R^8, R^9, R^10 substituted isoquinoline/quinoline]

$R^8$, $R^9$, $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0–2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for $R^8$, $R^9$ and $R^{10}$ are unsubstituted or substituted with any substituents set forth for Z Z is selected from among, halide, pseudoahlide, alkyl, alkoxy, alkenyl, alkynyl, aryl, aryloxy, heterocycle, aralkyl, aralkoxy, cycloalkyl, cycloalkenyl, cycloalkynyl OH CN, $C(O)R^{21}$, $CO_2R^{21}$, SH, $S(O) R^{21}$ in which n is 0–2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0–2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl; or (ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, that is unsubstituted or substituted with one or more substituents in each each substituent is independently selected from Z; and the other of $R^8$, $R^9$ and $R^{10}$ is selected as in (i).

3. The compounds of claim 1 in which $Ar^2$ is selected from among isoxazolyl, thiadiazolyl, thiazolyl, quinolinyl, and pryidyl.

4. The compounds of claim 1 in which $Ar^2$ is a five-membered heterocyclic ring with one heteroatom or fused ring analogs thereof, $Ar^2$ is a five-membered heterocycle with two or more heteroatoms or fused ring analogs thereof, $Ar^2$ is a six-membered heterocyclic ring compound with one heteroatom or fused ring analogs thereof, or $Ar^2$ is a six-membered heterocycle with two or more heteroatoms or fused ring analogs thereof.

5. The compounds of claim 1 in which $Ar^2$ is selected from thiazolyl, isoxoxaolyl, isothiazolyl, and 1,3,4-thiadiazolyl.

6. The compounds of claim 1 in which $Ar^2$ is selected from pyridinly, quinolinyl or isoquinolynl.

7. The compound of claim 1, wherein $Ar^2$ is pryidyl.

8. The compounds claim 1, wherein $R^1$ is selected from alkyl, lower alkenyl, lower alkynyl, lower haloalkyl, halide, and pseudohalide; and $R^2$ is selected from lower alkyl, lower haloalkyl and hydrogen.

9. The compounds of claim 1, wherein $R^1$ is selected from halide and alkyl, which contains from 8 to 15 carbon atoms, and $R^2$ is selected from lower alkyl and hydrogen.

10. The compounds of claim 1, wherein $R^1$ is selected from Br, Cl and alkyl that contains 9 to 13 carbon atoms.

11. The compounds of claim 1, wherein $R^1$ is halide.

12. The compounds of claim 1, wherein $R^1$ is alkyl that contains 9 to 13 carbon atoms.

13. The compounds of claim 1 that are selected from the group consisting of N-(4-bromo-3-methyl-5-isoxazolyl)-1-naphthalenesulfonamide; N-(4-bromo-5-methyl-3-isoxazolyl)-1-naphthalenesulfonamide; N-(4-bromo-3-ethyl-5-isoxazolyl)-1-naphthalenesulfonamide; N-(4-bromo-3-methyl-5-isoxazolyl)-1-naphthalenesulfonamide; 5-dimethylamino-N-(4-bromo-3-methyl-isoxazoyl)-1-nathalenesulfonamide or 5-dimethylamino-N-(4-bromo-5-methyl-3-isoxazoyl)-1-nathalenesulfonamide.

14. The compounds of claim 1 that are selected from the group consisting of N-(4-halo-3-methyl-5-isoxazolyl)-1-naphthalenesulfonamide; N-(4-halo-5-methyl-3-isoxazoyl)-1-napthalenesulfonamide; 5-dimethylamino-N-(4-halo-3-methyl-5-isoxazoyl)-1-napthalenesulfonamide; 5-dimethylamino-N-(4-halo-5-methyl-3-isoxazoyl)-1-napthalenesulfonamide, wherein halo is Br or Cl.

15. The compound of claim 1, that is 5-dimethylamino-N-( 4-bromo-3-methyl-5-isoxazoyl)-1-napthalenesulfonamide or 5-dimethylamino-N-(4-bromo-5-methyl-3-isoxazoyl)-1-napthalenesulfonamide.

16. A compound of claim 1, wherein: $Ar^2$ is a heterocycle with one heteroatom and two or more fused rings in which the heteroatom is O, S, N or $NR^1$ and the rings may be substituted with one or more substituents each independently selected from $R^{26}$, which is H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or cyclic, and the aryl portions contain from about 4 to about 16 carbons; and $R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are are unsubstituted or are substituted with one or more substituents each selected independently from Z which is halide, pseudoahlide, alkyl, alkoxy, alkenyl, alkynyl, aryl, heterocycle, aralkyl, aralkoxy, cycloalkyl cycloalkenyl, cycloalkynyl OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl.

17. The compounds of claim 16 in which $R^{26}$ H, alkyl, haloalkyl and halide and amino.

18. The compounds of claim 17 in which $Ar^2$ is quinolyl or isoquinolyl.

19. The compounds of claim 18 wherein $R^1$ is hydrogen, halide, or alkyl, or haloalkyl and $R^2$ is lower alkyl, lower haloalkyl, or hydrogen.

20. The compounds of claim 16, in which $Ar^2$ is quinolyl.

21. The compound of claim 16 that is N-(4-bromo-3-methyl-5-isoxazolyl)-8-quinolinesulfonamide; N-(4-bromo-5-methyl-3-isoxazolyl)-8-quinolinesulfonamide; or 8-ethoxy-N-(4-bromo-3-methyl-5-isoxazolyl)quinoline-5-sulfonamide.

22. The compounds of claim 16 in which $R^{26}$ is selected from H, $CH_3$, $C_2H_5$, $CF_3$, and halide; and X is O.

23. A compound of claim 1, wherein:

$Ar^2$ is a six-membered heterocycle with one heteroatom X selected from S, O, N or $NR^{11}$;

$R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are are unsubstituted or are substituted with one or more substituents each selected independently from Z which is halide, pseudoahlide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; and $Ar^2$ is unsubstituted or substituted with one or more substituents each independently selected from $R^{26}$, which is H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or cyclic, and the aryl portions contain from about 4 to about 16 carbons.

24. A compound of claim 23, wherein $R^1$ is selected from alkyl, lower alkenyl, lower alkynyl, lower haloalkyl, halide, pseudohalide and H; and $R^2$ is selected lower alkyl, lower alkenyl, lower alkynyl, lower haloalkyl, and H.

25. A compound of claim 24, wherein $R^{26}$ H, alkyl, haloalkyl and halide and amino.

26. A compound of claim 25 in which $R^1$ is halide, alkyl, or haloalkyl, and $R^2$ is lower alkyl, lower haloalkyl, or hydrogen.

27. A compound of claims 26 in which $Ar^2$ is pyridyl.

28. A compound of claim 23 selected from the group consisting of N-(4-bromo-3-methyl-5-isoxazolyl)pyridine-2-sulfonamide, N-(4-bromo-5-methyl-3-isoxazolyl)pyridine- 2-sulfonamide, N-(3,4-dimethyl-5-isoxazolyl)-2-pyridine-2-sulfonamide, N-(4,5-dimethyl-3-isoxazolyl)pyridine-2-sulfonamide, 3-methoxycarbonyl-N-(4-bromo-5-methyl-3-isoxazolyl)pyridine-2-sulfonamide and 3-methoxycarbonyl-N-(4-bromo-5-methyl-3-isoxazolyl)pyridine-2-sulfonamide, N-(3,4-dimethyl-5-isoxazolyl)-3-(N-phenylaminocarbonyl)pyridine-2-sulfonamide, N-(4-bromo-5-methyl-3-isoxazolyl)-3-(N-phenylaminocarbonyl)pyridine-2-sulfonamide, and N-(4-bromo-3-methyl-5-isoxazolyl)-3-(N-phenylaminocarbonyl)pyridine- 2-sulfonamide.

29. A compound of claim 1, wherein:

$Ar^2$ is a heterocycle that contains two or more heteroatoms selected from O, S, N, and $NR^{11}$, in which the heterocycle is unsubstituted or substituted with one or more substituents-selected from $R^{26}$, which is selected from H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or cyclic, and the aryl portions contain from about 4 to about 16 carbons; and $R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{16}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are are unsubstituted or are substituted with one or more substituents each selected independently from Z which is halide, pseudoahlide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl.

30. The compounds of claim 29 which $Ar^2$ is thiazolyl, oxazolyl, and pyrazolyl.

31. A compound of claim 30 that is selected from the group consisting of 5-acetamido-4-methyl-N-(3,4-dimethyl-5-isoxazolyl)thiazole-2-sulfonamide; 5-acetamido-4-methyl-N-(4-bromo-3-methyl- 5-isoxazolyl)thiazole-2-sulfonamide; N-(3,4-dimethyl-5-isoxazolyl)thiazole-2-sulfonamide; N-(4-bromo-3-methyl-5-isoxazolyl)thiazole-2-sulfonamide; N-(4-chloro-3-methyl-5-isoxazolyl)thiazole-2-sulfonamide; N-(3,4-dimethyl- 5-isoxazolyl)-4-benzofuransulfonamide; N-(3,4-dimethyl-5-isoxazolyl)benzo-2,1,3-thiadiazole- 4-sulfonamide; 5-chloro-1,3-dimethyl-N-(4-chloro-3-methyl-5-isoxazolyl)pyrazole- 4-sulfonamide; 5-chloro-1,3-dimethyl-N-(4-bromo-3-methyl-5-isoxazolyl)pyrazole- 4-sulfonamide; N-(4-bromo-3-methyl-5-isoxazolyl)benzo- 2,1,3-thiadiazole-4-sulfonamide; or 3,5-dimethyl-N-(4-bromo-3-methyl-5-isoxazolyl)isoxazole-4-sulfonamide.

32. The compound of claim 30 that is N-(4-bromo-3-methyl-5-isoxazolyl)benzo-2,1,3-thiadiazole- 4-sulfonamide; N-(4-bromo-5-methyl-3-isoxazolyl)benzo- 2,1,3-thiadiazole-4-sulfonamide; N-(4-chloro-3-methyl- 5-isoxazolyl)benzo-2,1,3-thiadiazole- 4-sulfonamide; or N-(4-chloro-5-methyl-3-isoxazolyl)benzo- 2,1,3-thiadiazole-4-sulfonamide.

33. A pharmaceutical composition, comprising a compound of claim 1 in a pharmaceutically acceptable carrier.

34. A method for the treatment of endothelin-mediated diseases, comprising administering an effective amount a compound of claim 1, wherein the effective amount is sufficient to ameliorate one or more of the symptoms of the disease.

35. A method for the treatment of endothelin-mediated diseases, comprising administering an effective amount a compound of claim 3, wherein the effective amount is sufficient to ameliorate one or more of the symptoms of the disease.

36. A method for the treatment of endothelin-mediated diseases, comprising administering an effective amount a compound of claim 4, wherein the effective amount is sufficient to ameliorate one or more of the symptoms of the disease.

37. A method for the treatment of endothelin-mediated diseases, comprising administering an effective amount a compound of claim 5, wherein the effective amount is sufficient to ameliorate one or more of the symptoms of the disease.

38. A method for the treatment of endothelin-mediated diseases, comprising administering an effective amount a compound of claim 8, wherein the effective amount is sufficient to ameliorate one or more of the symptoms of the disease.

39. A method for the treatment of endothelin-mediated diseases, comprising administering an effective amount a compound of claim 13, wherein the effective amount is sufficient to ameliorate one or more of the symptoms of the disease.

40. A method for the treatment of endothelin-mediated diseases, comprising administering an effective amount a compound of claim 14, wherein the effective amount is sufficient to ameliorate one or more of the symptoms of the disease.

41. A method for the treatment of endothelin-mediated diseases, comprising administering an effective amount a compound of claim 16, wherein the effective amount is sufficient to ameliorate one or more of the symptoms of the disease.

42. A method for the treatment of endothelin-mediated diseases, comprising administering an effective amount a compound of claim 8, wherein the effective amount is sufficient to ameliorate one or more of the symptoms of the disease.

43. A method for the treatment of endothelin-mediated diseases, comprising administering an effective amount a compound of claim 22, wherein the effective amount is sufficient to ameliorate one or more of the symptoms of the disease.

44. A method for the treatment of endothelin-mediated diseases, comprising administering an effective amount a compound of claim 23, wherein the effective amount is sufficient to ameliorate one or more of the symptoms of the disease.

45. A method for the treatment of endothelin-mediated diseases, comprising administering an effective amount a compound of claim 24, wherein the effective amount is sufficient to ameliorate one or more of the symptoms of the disease.

46. A method for the treatment of endothelin-mediated diseases, comprising administering an effective amount a compound of claim 26, wherein the effective amount is sufficient to ameliorate one or more of the symptoms of the disease.

47. A method for the treatment of endothelin-mediated diseases, comprising administering an effective amount a compound of claim 28, wherein the effective amount is sufficient to ameliorate one or more of the symptoms of the disease.

48. A method for the treatment of endothelin-mediated diseases, comprising administering an effective amount a compound of claim 29 wherein the effective amount is sufficient to ameliorate one or more of the symptoms of the disease.

49. The method of claim 34, wherein the disease is selected from the group consisting of hypertension, cardiovascular disease, asthma, pulmonary hypertension, inflammatory diseases, ophthalmologic disease, elevated intraocular pressure, glaucoma, menstrual disorders, obstetric conditions, wounds, gastroenteric disease, renal failure, immunosuppressant-mediated renal vasoconstriction, erythropoietin-mediated vasoconstriction, ischemia, pulmonary hypertension, anaphylactic shock and hemorrhagic shock.

50. The method of claim 34, wherein the disease is selected from the group consisting of hypertension, cardiovascular disease, pulmonary hypertension, erythropoietin-mediated vasoconstriction endotoxin shock, pulmonary hypertension, anaphylactic shock and hemorrhagic shock.

51. The method of claim 34, wherein the disease is selected from the group consisting of asthma and inflammatory diseases.

52. A method for inhibiting the binding of an endothelin peptide to endothelin$_A$ (ET$_A$) or endothelin$_B$ (ET$_B$) receptors, comprising contacting the receptors an endothelin peptide and with one or more compounds of claim 1, wherein:
the contacting is effected prior to, simultaneously with or subsequent to contacting the receptors with the endothelin peptide.

53. A method for inhibiting the binding of an endothelin peptide to endothelin$_A$ (ET$_A$) or endothelin$_B$ (ET$_B$) receptors, comprising contacting the receptors an endothelin peptide and with one or more compounds of claim 3, wherein:
the contacting is effected prior to, simultaneously with or subsequent to contacting the receptors with the endothelin peptide.

54. A method for altering endothelin receptor-mediated activity, comprising contacting endothelin receptors with a compound of claim 1.

55. A method for altering endothelin receptor-mediated activity, comprising contacting endothelin receptors with a compound of claim 3.

56. A pharmaceutical composition formulated for single dosage administration, comprising an effective amount of a compound of claim 1, wherein the amount is effective for ameliorating the symptoms of an endothelin-mediated disease.

57. An article of manufacture, comprising packaging material and a compound of claim 1 contained within the packaging material, wherein the compound is effective for antagonizing the effects of endothelin, ameliorating the symptoms of an endothelin-mediated disorder, or inhibiting the binding of an endothelin peptide to an ET receptor with an IC$_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder, 58. A pharmaceutical composition, comprising a compound of claim 3 in a pharmaceutically acceptable carrier.

59. A pharmaceutical composition, comprising a compound of claim 4 in a pharmaceutically acceptable carrier.

60. A pharmaceutical composition, comprising a compound of claim 5 in a pharmaceutically acceptable carrier.

61. A pharmaceutical composition, comprising a compound of claim 8 in a pharmaceutically acceptable carrier.

62. A pharmaceutical composition, comprising a compound of claim 13 in a pharmaceutically acceptable carrier.

63. A pharmaceutical composition, comprising a compound of claim 14 in a pharmaceutically acceptable carrier.

64. A pharmaceutical composition, comprising a compound of claim 16 in a pharmaceutically acceptable carrier.

65. A pharmaceutical composition, comprising a compound of claim 18 pharmaceutically acceptable carrier.

66. A pharmaceutical composition, comprising a compound of claim 21 in a pharmaceutically acceptable carrier.

67. A pharmaceutical composition, comprising a compound of claim 22 in a pharmaceutically acceptable carrier.

68. A pharmaceutical composition, comprising a compound of claim 23 in a pharmaceutically acceptable carrier.

69. A pharmaceutical composition, comprising a compound of claim 24 in a pharmaceutically acceptable carrier.

70. A pharmaceutical composition, comprising a compound of claim 26 in a pharmaceutically acceptable carrier.

71. A pharmaceutical composition, comprising a compound of claim 28 in a pharmaceutically acceptable carrier.

72. A pharmaceutical composition, comprising a compound of claim 29 in a pharmaceutically acceptable carrier.

73. A pharmaceutical composition, comprising a compound of claim 30 in a pharmaceutically acceptable carrier.

74. A pharmaceutical composition, comprising a compound of claim 31 in a pharmaceutically acceptable carrier.

75. An article of manufacture, comprising packaging material and a compound of claim 3 contained within the packaging material, wherein the compound is effective for antagonizing the effects of endothelin, ameliorating the symptoms of an endothelin-mediated disorder, or inhibiting the binding of an endothelin peptide to an ET receptor with an IC$_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder.

76. An article of manufacture, comprising packaging material and a compound of claim 4 contained within the packaging material, wherein the compound is effective for antagonizing the effects of endothelin, ameliorating the symptoms of an endothelin-mediated disorder, or inhibiting the binding of an endothelin, peptide to an ET receptor with an IC$_{50}$ of less than about 10 μM; and the packaging material includes a label that indicates that the compound or salt thereof is used for antagonizing the effects of endothelin, inhibiting the binding of endothelin to an endothelin receptor or treating an endothelin-mediated disorder.

77. An article of manufacture, comprising packaging material and a compound of claim 13 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

78. An article of manufacture, comprising packaging material and a compound of claim 16 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

79. An article of manufacture, comprising packaging material and a compound of claim 23 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

80. An article of manufacture, comprising packaging material and a compound of claim 27 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

81. An article of manufacture comprising packaging material and a compound of claim 29 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

82. An article of manufacture, comprising packaging material and a compound of claim 30 contained within the packaging material, wherein the compound is effective for antagonizing the effects of endothelin, ameliorating the symptoms of an endothelin-mediated disorder, or inhibiting the binding of an endothelin peptide to an ET receptor with an $IC_{50}$ of less than about 10 µM; and the packaging material includes a label that indicates that the compound or salt thereof is used for antagonizing the effects of endothelin, inhibiting the binding of endothelin to an endothelin receptor or treating an endothelin-mediated disorder.

83. A method for the treatment of endothelin-mediated diseases, comprising administering an effective amount a compound of claim 30, wherein the effective amount is sufficient to ameliorate one or more of the symptoms of the disease.

84. A method for the treatment of endothelin-mediated diseases, comprising administering an effective amount a compound of claim 31, wherein the effective amount is sufficient to ameliorate one or more of the symptoms of the disease.

85. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 4, wherein:
the contacting is effected prior to, simultaneously with or subsequent to contacting the receptors with the endothelin peptide.

86. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 13, wherein:
the contacting is effected prior to, simultaneously with or subsequent to contacting the receptors with the endothelin peptide.

87. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 16, wherein:
the contacting is effected prior to, simultaneously with or subsequent to contacting the receptors with the endothelin peptide.

88. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 23, wherein:
the contacting is effected prior to, simultaneously with or subsequent to contacting the receptors with the endothelin peptide.

89. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 27, wherein:
the contacting is effected prior to, simultaneously with or subsequent to contacting the receptors with the endothelin peptide.

90. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 29, wherein:
the contacting is effected prior to, simultaneously with or subsequent to contacting the receptors with the endothelin peptide.

91. A method for inhibiting the binding of an endothelin peptide to endothelin$_A$ ($ET_A$) or endothelin$_B$ ($ET_B$) receptors, comprising contacting the receptors an endothelin peptide and with one or more compounds of claim 30, wherein:
the contacting is effected prior to, simultaneously with or subsequent to contacting the receptors with the endothelin peptide.

\* \* \* \* \*

UNITED STATES PATENT AND TRADEMARK OFFICE
CERTIFICATE OF CORRECTION

PATENT NO.: 5,571,821

DATED: November 5, 1996

INVENTOR(S): Chan et al.

Page 1 of 9

It is certified that error appears in the above-identified patent and that said Letters Patent is hereby corrected as shown below:

IN THE TITLE PAGE:

In item [75], entitled Inventors, delete "Kalyanaraman Ramnarayan" as an inventor;

in item [63], entitled Related U.S. Application Data, line 8, "142,559" should read —142,552—;

in item [63], entitled Related U.S. Application Data, lines 8 and 9, delete "Oct. 25, 1993, Pat. No. 5,378,463"; and in item [63], entitled Related U.S. Application Data, lines 10 and 11, "142,559" should read —142,552—.

At column 1, lines 41 and 42, "08/142,559" should read —08/142,552—;
at column 1, line 42, delete "filed Oct. 25, 1993, now U.S. Pat. No. 5,373,463";
at column 1, lines 43-44, delete "filed Oct. 25, 1993, now U.S. Pat. No. 5,373,463";
at column 1, line 45, "08/142,559" should read —08/142,552—;
at column 1, line 51, "08/142,559" should read —08/142,552—;
at column 1, line 60, insert —one— between "at least" and "member";
at column 5, line 32, delete "Clozel et al." after "Clozel et al.";
at column 6, line 8, delete "should" before "may aid in the design";
at column 6, line 47, replace "particuarl" with —particular—;
at column 7, line 38, insert —,— in between "alkyl" and "alkylcarbonyl";
at column 8, line 3, delete "." after "including";
at column 8, line 7, replace "admantyl" with —adamantyl—;
at column 8, line 9, replace "imidazole" with —imidazolyl—;
at column 8, lines 10-11, replace "thianaphthalene" with —thianaphthyl—;
at column 8, line 12, delete "imidazolyl";
at column 8, line 12, delete "oxazolyl";
at column 8, line 14, replace "pyradazinyl" with —pyridazinyl—;
at column 8, line 14, replace "quiniolzoliny" with —quinazolinyl—;
at column 8, line 15, replace "quniolxazinyl" with —quinoxalinyl—;
at column 8, lines 15 and 16, replace "phenoxzainyl" with —phenoxazinyl—;
at column 8, line 19, replace "thiadazolyl" with —thiadiazolyl—;
at column 9, line 51, delete "are" after "are";
at column 10, line 35, insert —,— between "halide" and "pseudohalide";
at column 10, line 48, delete "is" after "is";
at column 10, line 49, replace "pseudoahlide" with —pseudohalide—;
at column 11, line 10, replace "retains" with —retain—;
at column 11, line 19, replace "thianaphthalyl" with —thianaphthyl—;
at column 11, line 19, replace "dibenzofuranyl" with —dibenzofuryl—;
at column 11, line 21, replace "anthacenyl" with —anthracenyl—;

UNITED STATES PATENT AND TRADEMARK OFFICE
CERTIFICATE OF CORRECTION

PATENT NO.:        5,571,821

DATED:             November 5, 1996

INVENTOR(S):       Chan et al.

It is certified that error appears in the above-identified patent and that said Letters Patent is hereby corrected as shown below:

at column 11, line 38, delete "of" after "competitive";
at column 11, line 40, delete "to";
at column 12, line 15, replace "preferablly" with —preferably—;
at column 18, line 22, replace "sulfonmides" with —sulfonamides—;
at column 19, line 54, replace "naphthalenesulfonamdies" with —naphthalenesulfonamides—;
at column 20, line 9, delete "an";
at column 20, line 15, replace "than" with —then—;
at column 20, line 20, replace "if" with —is—;
at column 22, line 33, replace "$R^{32}$" with —$R^{31}$—;
at column 24, line 59, delete "d" after "$C_{13}H_{27}$;";
at column 25, line 2, replace "whcih" with —which—;
at column 25, line 3, replace "from" with —form—;
at column 26, line 9, replace "particular" with —particularly—;
at column 26, line 11, replace "the following Table" with —Table 1—;
at column 26, line 15, replace "generlly" with —generally—;
at column 31, lines 48-60, delete

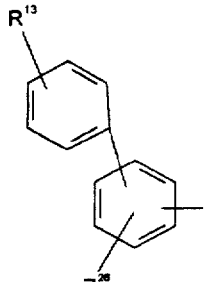

and insert

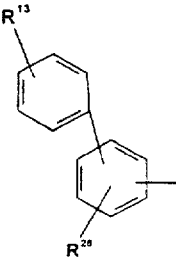

in place thereof;

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

at column 34, line 67, replace "heterolaryl" with —heteroaryl—;
at column 37, line 28, insert —in— before "which";
at column 38, line 16, insert —as follows— after "independently";
at column 41, line 20, replace "substiuted" with —substituted—;
at column 42, line 23, delete "which" after "which";
at column 42, line 27, delete "is a" after "is a";
at column 42, line 37, replace "isoxoxaolyl" with —isoxazolyl—;
at column 42, line 42 replace "pyridinly" with —pyridyl—;
at column 42, line 43, replace "isoquinolynl" with —isoquinolyl—;
at column 42, line 49, delete "pterdinyl";
at column 42, line 50, delete "morpholinyl";
at column 42, line 51, delete "quniazolinyl";
at column 42, line 51, delete "quinoxalinyl";
at column 45, line 32, delete "each" after "each";
at column 45, line 44, replace "exhibits" with —exhibit—;
at column 45, line 58, delete "from" after "from";
at column 49, Table 6, delete "822" from the beginning of the line reading "822N-(4-bromo-3-methyl-5-isoxazolyl)-4-(4'-isopropylphenyl))thiophene-2-sulfonamide;
at column 52, line 62, replace "R6" with —$R^{26}$—;
at column 54, Table 9, replace "N-(4-bromo-3-methyl-5-isoxazolyl)benzo-O 2,1,3-thiadiazole-4-sulfonamide" with —N-(4-bromo-3-methyl-5-isoxazolyl)benzo-2,1,3-thiadiazole-4-sulfonamide—;
at column 65, line 42, replace "Parental" with —Parenteral—;
at column 93, line 49, replace "ws" with —was—;
at column 99, line 67, replace "needed" with —needles—; and
at column 102, line 9, replace "prepard" with —prepared—.

UNITED STATES PATENT AND TRADEMARK OFFICE
CERTIFICATE OF CORRECTION

PATENT NO.: 5,571,821  Page 4 of 9

DATED: November 5, 1996

INVENTOR(S): Chan *et al.*

It is certified that error appears in the above-identified patent and that said Letters Patent is hereby corrected as shown below:

IN THE CLAIMS:

Replace claims 1, 2, 3, 5, 6, 7, 13, 16, 17, 23, 25, 27, 29, 30, and 34-48 with the following claims:

1. A compound of formula I:

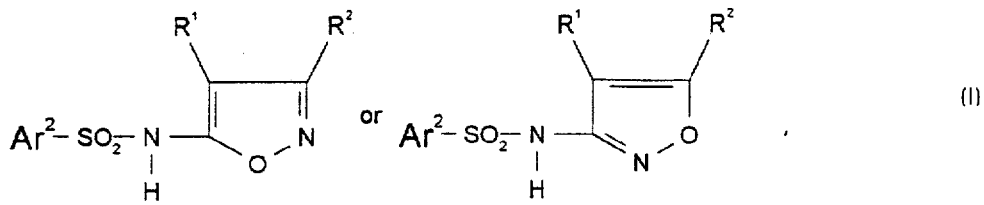

wherein:
$R^1$ and $R^2$ are either (i), (ii) or (iii) as follows:
  (i) $R^1$ and $R^2$ are independently selected from H, $NH_2$, $NO_2$, halide, pseudohalide, alkyl, alkenyl, alkynyl, aryl, arylalkyl, heteroaryl, alkoxy, alkylamino, hydroxyalkyl, alkoxyalkyl, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, with the proviso that $R^2$ is not halide or pseudohalide; or,
  (ii) $R^1$ and $R^2$ together form $-(CH_2)_n-$, where n is 3 to 6; or,
  (iii) $R^1$ and $R^2$ together form 1,3-butadienyl; and
$Ar^2$ is a heterocycle containing up to about 16 carbons in the ring, except that $Ar^2$ is not naphthyl unless the compound is an N-isoxazolylsulfonamide substituted at the 4-position on the isoxazolyl group with halide or higher alkyl that contains from 8 to 15 carbon atoms and is a straight or branched chain.

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

2. The compounds of claim 1, wherein:
$Ar^2$ is selected from:

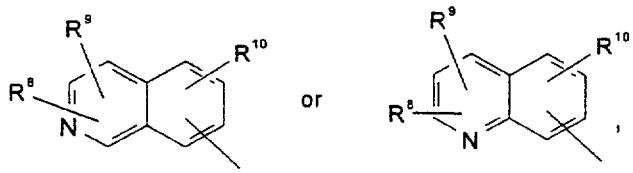

$R^8$, $R^9$, $R^{10}$ are each independently selected as follows from (i) or (ii):

(i) $R^8$, $R^9$ and $R^{10}$, which each contain hydrogen or up to about 50 carbon atoms, generally up to about 30, more generally 20 or fewer, are each independently selected from hydrogen, halide, pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{18}$, $CO_2R^{18}$, SH, $S(O)_nR^{18}$ in which n is 0-2, HNOH, $NR^{18}R^{19}$, $NO_2$, $N_3$, $OR^{18}$, $R^{19}NCOR^{18}$ and $CONR^{19}R^{18}$, in which $R^{19}$ is selected from hydrogen, alkyl, alkenyl, alkynyl, aryl, alkylaryl, alkoxy, aryloxy, heterocycle, aralkyl, aralkoxy, cycloalkyl, cycloalkenyl, cycloalkynyl, $C(O)R^{20}$, $S(O)_nR^{20}$ in which n is 0-2; and $R^{18}$ and $R^{20}$ are independently selected from hydrogen, alkyl, alkenyl, alkynyl, aryl, alkylaryl, heterocycle, alkoxy, aryloxy, aralkyl, aralkoxy, cycloalkyl, cycloalkenyl or cycloalkynyl; and any of the groups set forth for $R^8$, $R^9$ and $R^{10}$ are unsubstituted or substituted with any substituents set forth for Z Z is selected from among halide pseudohalide, alkyl, alkoxy, alkenyl, alkynyl, aryl, aryloxy, heterocycle, aralkyl, aralkoxy, cycloalkyl, cycloalkenyl, cycloalkynyl, OH, CN, $C(O)R^{21}$, $CO_2R^{21}$, SH, $S(O)_nR^{21}$ in which n is 0-2, NHOH, $NR^{22}R^{21}$, $NO_2$, $N_3$, $OR^{21}$, $R^{22}NCOR^{21}$ and $CONR^{22}R^{21}$; $R^{22}$ is selected from hydrogen, alkyl, alkenyl, alkynyl, aryl, alkylaryl, heterocycle, aralkyl, alkoxy, aralkoxy, cycloalkyl, cycloalkenyl, cycloalkynyl, $C(O)R^{23}$ and $S(O)_nR^{23}$ in which n is 0-2; and $R^{21}$ and $R^{23}$ are independently selected from hydrogen, alkyl, alkenyl, alkynyl, aryl, alkylaryl, heterocycle, aralkyl, aralkoxy, cycloalkyl, cycloalkenyl or cycloalkynyl; or (ii) any two of $R^8$, $R^9$ and $R^{10}$ form an aryl, aromatic ring, heteroaromatic ring, alicyclic or heterocyclic ring, which is saturated or unsaturated, containing from about 3 to about 16 members, that is unsubstituted or substituted with one or more substituents in each substituent is independently selected from Z; and the other of $R^8$, $R^9$ and $R^{10}$ is selected as in (i).

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

3. The compounds of claim 1 in which $Ar^2$ is selected from among isoxazolyl, thiadiazolyl, thiazolyl, quinolinyl, and pyridyl.

5. The compounds of claim 1 in which $Ar^2$ is selected from thiazolyl, isoxazolyl, isothiazolyl, and 1,3,4-thiadiazolyl.

6. The compounds of claim 1 in which $Ar^2$ is selected from pyridinyl, quinolinyl or isoquinolinyl.

7. The compound of claim 1, wherein $Ar^2$ is pyridyl.

13. The compounds of claim 1 that are selected from the group consisting of N-(4-bromo-3-methyl-5-isoxazolyl)-1-naphthalenesulfonamide; N-(4-bromo-5-methyl-3-isoxazolyl)-1-naphthalenesulfonamide; N-(4-bromo-3-ethyl-5-isoxazolyl)-1-naphthalenesulfonamide; N-(4-bromo-3-methyl-5-isoxazolyl)-1-naphthalenesulfonamide; 5-dimethylamino-N-(4-bromo-3-methyl-5-isoxazoyl)-1-napthalenesulfonamide or 5-dimethylamino-N-(4-bromo-5-methyl-3-isoxazoyl)-1-napthalenesulfonamide.

16. A compound of claim 1, wherein:

$Ar^2$ is a heterocycle with one heteroatom and two or more fused rings in which the heteroatom is O, S, N or $NR^{11}$ and the rings may be substituted with one or more substituents each independently selected from $R^{26}$, which is H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or cyclic, and the aryl portions contain from about 4 to about 16 carbons; and $R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0-2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z which is halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0-2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0-2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl.

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

17. The compounds of claim 16 in which $R^{26}$ is H, alkyl, haloalkyl and halide and $NH_2$.

23. A compound of claim 1, wherein:

$Ar^2$ is a six-membered heterocycle with one heteroatom X selected from S, O, N or $NR^{11}$;

$R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0-2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z which is halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2R^{16}$, SH, $S(O)_nR^{16}$ in which n is 0-2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0-2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl; and $Ar^2$ is unsubstituted or substituted with one or more substituents each independently selected from $R^{26}$, which is H, OH, OHNH, $NH_2$, $NO_2$, halide, pseudohalide, alkyl, alkenyl, alkynyl, aryl, arylalkyl, heterolaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloalkyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or cyclic, and the aryl portions contain from about 4 to about 16 carbons.

25. A compound of claim 24, wherein $R^{26}$ is H, alkyl, haloalkyl, halide or amino.

27. A compound of claim 26 in which $Ar^2$ is pyridyl.

29. A compound of claim 1, wherein:

$Ar^2$ is a heterocycle that contains two or more heteroatoms selected from O, S, N, and $NR^{11}$, in which the heterocycle is unsubstituted or substituted with one or more substituents selected from $R^{26}$, which is selected from H, OH, OHNH, $NH_2$, $NO_2$, halide, pseudohalide, alkyl, alkenyl, alkynyl, aryl, arylalkyl, heteroaryl, alkoxy, alkylamino, dialkylamino, alkylthio, haloalkoxy, haloalkyl, alkylsufinyl, alkylsulfonyl, aryloxy, arylamino, arylthio, arylsufinyl, arylsulfonyl, haloaryl, alkoxycarbonyl, carbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms, and are either straight or branched chains or

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

cyclic, and the aryl portions contain from about 4 to about 16 carbons; and $R^{11}$, which is hydrogen or contains up to about 30 carbon atoms, and is selected from the group consisting of hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_n R^{15}$ in which n is 0-2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z which is halide, pseudohalide, alkyl, alkoxy, alkenyl, alkynyl, aryl, heterocycle, aralkyl, aralkoxy, cycloalkyl, cycloalkenyl, cycloalkynyl, OH, CN, $C(O)R^{16}$, $CO_2 R^{16}$, SH, $S(O)_n R^{16}$ in which n is 0-2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$, which is selected independently from $R^{11}$, which is selected independently from $R^{11}$ and Z is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_n R^{17}$ in which n is 0-2; and $R^{17}$ is hydrogen, alkyl, alkenyl, alkynyl, aryl, alkylaryl, heterocycle, aralkyl, aralkoxy, cycloalkyl, cycloalkenyl or cycloalkynyl.

30. The compounds of claim 29 in which $Ar^2$ is thiazolyl, oxazolyl, and pyrazolyl.

34. A method for the treatment of endothelin-mediated diseases, comprising administering an effective amount of a compound of claim 1, wherein the effective amount is sufficient to ameliorate one or more of the symptoms of the disease.

35. A method for the treatment of endothelin-mediated diseases, comprising administering an effective amount of a compound of claim 3, wherein the effective amount is sufficient to ameliorate one or more of the symptoms of the disease.

36. A method for the treatment of endothelin-mediated diseases, comprising administering an effective amount of a compound of claim 4, wherein the effective amount is sufficient to ameliorate one or more of the symptoms of the disease.

37. A method for the treatment of endothelin-mediated diseases, comprising administering an effective amount of a compound of claim 5, wherein the effective amount is sufficient to ameliorate one or more of the symptoms of the disease.

38. A method for the treatment of endothelin-mediated diseases, comprising administering an effective amount of a compound of claim 8, wherein the effective amount is sufficient to ameliorate one or more of the symptoms of the disease.

39. A method for the treatment of endothelin-mediated diseases, comprising administering an effective amount of a compound of claim 13, wherein the effective amount is sufficient to ameliorate one or more of the symptoms of the disease.

40. A method for the treatment of endothelin-mediated diseases, comprising administering an effective amount of a compound of claim 14, wherein the effective amount is sufficient to ameliorate one or more of the symptoms of the disease.

UNITED STATES PATENT AND TRADEMARK OFFICE
CERTIFICATE OF CORRECTION

PATENT NO.: 5,571,821

DATED: November 5, 1996

INVENTOR(S): Chan et al.

It is certified that error appears in the above-identified patent and that said Letters Patent is hereby corrected as shown below:

41. A method for the treatment of endothelin-mediated diseases, comprising administering an effective amount of a compound of claim 16, wherein the effective amount is sufficient to ameliorate one or more of the symptoms of the disease.

42. A method for the treatment of endothelin-mediated diseases, comprising administering an effective amount of a compound of claim 18, wherein the effective amount is sufficient to ameliorate one or more of the symptoms of the disease.

43. A method for the treatment of endothelin-mediated diseases, comprising administering an effective amount of a compound of claim 22, wherein the effective amount is sufficient to ameliorate one or more of the symptoms of the disease.

44. A method for the treatment of endothelin-mediated diseases, comprising administering an effective amount of a compound of claim 23, wherein the effective amount is sufficient to ameliorate one or more of the symptoms of the disease.

45. A method for the treatment of endothelin-mediated diseases, comprising administering an effective amount of a compound of claim 24, wherein the effective amount is sufficient to ameliorate one or more of the symptoms of the disease.

46. A method for the treatment of endothelin-mediated diseases, comprising administering an effective amount of a compound of claim 26, wherein the effective amount is sufficient to ameliorate one or more of the symptoms of the disease.

47. A method for the treatment of endothelin-mediated diseases, comprising administering an effective amount of a compound of claim 28, wherein the effective amount is sufficient to ameliorate one or more of the symptoms of the disease.

48. A method for the treatment of endothelin-mediated diseases, comprising administering an effective amount of a compound of claim 29, wherein the effective amount is sufficient to ameliorate one or more of the symptoms of the disease.

Signed and Sealed this

Twenty-sixth Day of December, 2000

Q. TODD DICKINSON

*Attest:*

*Attesting Officer*            *Director of Patents and Trademarks*